(12) United States Patent
Horne et al.

(10) Patent No.: US 6,579,890 B1
(45) Date of Patent: *Jun. 17, 2003

(54) MATRIX METALLOPROTEASE INHIBITORS

(75) Inventors: Stephen Horne, Burlington (CA); Teng J. Liak, Mississauga (CA)

(73) Assignee: Syntex (U.S.A.) Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/468,762

(22) Filed: Dec. 21, 1999

Related U.S. Application Data

(60) Division of application No. 08/343,158, filed on Nov. 22, 1994, now Pat. No. 6,037,472, which is a continuation-in-part of application No. 08/147,811, filed on Nov. 4, 1993, now abandoned.

(51) Int. Cl.[7] ............... A61K 31/4409; C07D 213/72
(52) U.S. Cl. ............... 514/342; 514/352; 546/270.4; 546/309
(58) Field of Search ............... 546/309, 270.4; 514/352, 342

(56) References Cited

U.S. PATENT DOCUMENTS

| | | | |
|---|---|---|---|
| 4,558,034 A | 12/1985 | Galardy et al. | 514/7 |
| 4,576,941 A | 3/1986 | Suh et al. | 514/222 |
| 4,696,939 A | 9/1987 | Suh et al. | 514/361 |
| 4,801,609 A | 1/1989 | Haslanger et al. | 514/506 |
| 4,885,283 A | 12/1989 | Broadhurst et al. | 514/78 |
| 4,996,358 A | 2/1991 | Handa et al. | 562/621 |
| 5,006,651 A | 4/1991 | Broadhurst et al. | 540/463 |
| 5,017,589 A * | 5/1991 | Kawamura et al. | 514/352 |
| 5,061,710 A * | 10/1991 | Haslanger et al. | 514/266 |
| 5,114,953 A * | 5/1992 | Galardy et al. | 514/323 |
| 5,124,322 A | 6/1992 | Hughes | 514/183 |
| 5,183,900 A | 2/1993 | Galardy et al. | 548/495 |
| 5,189,178 A | 2/1993 | Galardy et al. | 548/495 |
| 5,190,937 A | 3/1993 | Markwell et al. | 514/183 |
| 5,268,384 A | 12/1993 | Galardy | 514/419 |
| 5,304,604 A | 4/1994 | Davidson et al. | 514/238.2 |
| 5,696,147 A | 12/1997 | Galardy | 514/419 |
| 5,773,438 A | 6/1998 | Levy et al. | 514/237.8 |
| 6,037,472 A * | 3/2000 | Castelhano et al. | 549/269.7 |

FOREIGN PATENT DOCUMENTS

| | | | |
|---|---|---|---|
| EP | 0 046 707 | 3/1982 | |
| EP | 0 210 545 | 2/1987 | |
| EP | 0 276 436 | 8/1988 | |
| EP | 0341 081 A2 | 11/1989 | |
| EP | 0 386 611 | 12/1990 | |
| EP | 0 438 223 | 7/1991 | |
| EP | 0 489 577 | 6/1992 | |
| EP | 0 489 579 | 6/1992 | ......... C07C/259/06 |
| EP | 0 497 192 | 8/1992 | |
| EP | 0 498 665 | 8/1992 | |
| WO | WO 91/02716 | 3/1991 | |
| WO | WO 91/15507 | 10/1991 | |
| WO | WO 92/06966 | 4/1992 | |
| WO | WO 92/09556 | 6/1992 | |
| WO | WO 92/09563 | 6/1992 | |
| WO | WO92/09564 | 6/1992 | ......... C07C/259/06 |
| WO | WO92/09565 | 6/1992 | ......... C07C/259/06 |
| WO | WO 92/21360 | 12/1992 | |
| WO | WO93/13741 | 7/1993 | |
| WO | WO 93/14112 | 7/1993 | |
| WO | WO93/24449 | 12/1993 | ......... C07C/237/22 |
| WO | WO93/24475 | 12/1993 | ......... C07D/295/22 |
| WO | WO 94/07481 | 4/1994 | |
| WO | WO94/07481 | 4/1994 | ......... A61K/31/16 |
| WO | WO 94/25434 | 11/1994 | ......... C07C/323/60 |
| WO | WO 94/25435 | 11/1994 | ......... C07C/323/60 |
| WO | WO 95/19956 | 7/1995 | |

OTHER PUBLICATIONS

Chapman, et al., *J. Med. Chem* (1993), "Inhibition of Matrix Metalloproteinases by N–Carboxyalkyl Peptides", vol. 36, pp. 4293–4301.

Lohmander, L.S., et al., *Arthritis and Rheumatism* (1993), "Metalloproteinases, Tissue Inhibitor, and Proteoglycan Fragments in Knee Synovial Fluid in Human Osteoarthritis", vol. 36, No. 2, pp. 181–189.

Rodgers, W.H., et al., *Am J Obstet Gynecol* (*1993*), "Expression and Localization of Matrilysin, a Matrix Metalloproteinase, in Human Endometrium During the Reproductive Cycle", vol. 168, pp. 253–260.

Sires, U.I., et al., *The Journal of Biological Chemistry* (1993), "Degradation of Entactin by Matrix Metalloproteinases", vol. 268, No. 3, pp. 2069–2074.

Busiek, D.F., et al., *The Journal of Biological Chemistry* (1992), The Matrix Metalloprotease Matrilysin (PUMP) Is Expressed in Developing Human Mononuclear Phagocytes, vol. 267, No. 13, pp. 9087–9092.

(List continued on next page.)

*Primary Examiner*—Laura L. Stockton
(74) *Attorney, Agent, or Firm*—Heller Erhman White & McAliffe LLP

(57) ABSTRACT

Compounds of formula (I)

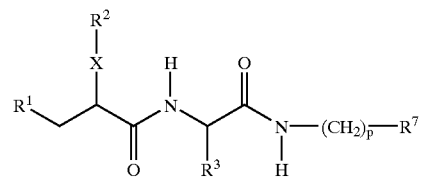

formula (I)

and their pharmaceutically acceptable salts inhibit matrix metalloproteases, such as stromelysin, gelatinase, matrilysin and collagenase, and are useful in the treatment of mammals having disease-states alleviated by the inhibition of such matrix metalloproteases.

7 Claims, No Drawings

OTHER PUBLICATIONS

Crabbe, T., et al., *Biochemistry* (1992), "Biochemical Characterization of Matrilysin. Activation Conforms to the Stepwise Mechanisms Proposed for Other Matrix Metalloproteinases", vol. 31, No. 36, pp. 8500–8507.

Murphy, G., et al., *The Journal of Biological Chemistry* (1992), "The Role of the C–terminal Domain in Collagenase and Stromelysin Specificity", vol. 267, No. 14, pp. 9612–9618.

Niedzwiecki, L., et al., *Biochemistry* (1992), "Substrate Specificity of the Human Matrix Metalloproteinase Stromelysin and the Development of Continuous Fluorometric Assays", vol. 31, No. 50, pp. 12618–12623.

Flannery, C.R., et al., *The Journal of Biological Chemistry* (1992), "Identification of a Stromelysin Cleavage Site within the Interglobular Domain of Human Aggrecan", vol. 267, No. 2, pp. 1008–1014.

Harrison, R.K, et al., *Biochemistry* (1992), "Mechanistic Studies on the Human Matrix Metalloproteinase Stromelysin", vol. 31, No. 44, pp. 10757–10762.

Salowe, S.P., et al., *Biochemistry* (1992), "Characterization of Zinc–Binding Sites in Human Stromelysin–1: Stoichiometry of the Catalytic Domain and Identification of a Cysteine Ligand in the Proenzyme", vol. 31, No. 19, pp. 4535–4540.

Ye, Q. et al., *Biochemistry* (1992), "Purification and Characterization of the Human Stromelysin Catalytic Domain Expressed in *Escherichia coli*", vol. 31, No. 45, pp. 11231–11235.

Wu, J–J., et al., *The Journal of Biological Chemistry* (1991), "Sites of Stromelysin Cleavage in Collagen Types II, IX, X, and XI of Cartilage", vol. 266, No. 9, pp. 5625–5628.

Nixon, J.S., et al., *Int. J. Tiss. Reac.* (1991), "Potent Collagenase Inhibitors Prevent Interleukin–1–Induced Cartilage Degradation In Vitro", vol. 13, No. 5, pp. 237–243.

Marcy, A.I., et al., Biochemistry (1991), "Human Fibroblast Stromelysin Catalytic Domain: Expression, Purification, and Characterization of a C–Terminally Truncated Form", vol. 30, No. 26, pp. 6476–6483.

Brinckerhoff, C.E., *Arthritis and Rheumatism* (1991), "Joint Destruction in Arthritis: Metalloproteinases in the Spotlight", vol. 34, No. 9, pp. 1073–1075.

Basset, P., et al., Nature (1990), "A Novel Metalloproteinase Gene Specifically Expressed in Stromal Cells of Breast Carcinomas", vol. 348, No. 20/27, pp. 699–703.

Johnson, W.H., *Drug News & Perspectives* (1990), "Collagenase Inhibitors", vol. 3, No. 8, pp. 453–458.

Shinmei, M., *Seminars in Arthritis and Rheumatism* (1990), "The Mechanism of Cartilage Degradation in Osteoarthritic Joints", vol. 19, No. 4, pp. 16–20.

Rosenberg, G.A., *Stroke* (1990), "Collagenase–Induced Intracerebral Hemorrhage in Rats", vol. 21, No. 5, pp. 801–807.

Henderson, B., et al., *Drugs of the Future* (1990), "Design of Inhibitors of Articular Cartilage Destruction", vol. 15, No. 5, pp. 495–508.

Dieppe, P.A., et al., *Arthritis and Rheumatism* (1988), "Synovial Fluid Collagenase in Patients with Destructive Arthritis of the Shoulder Joint", vol. 31, No. 7, pp. 882–890.

Johnson, W.H., et al., *J. Enzyme Inhibition* (1987), "Collagenase Inhibitors: Their Design and Potential Therapeutic Use", vol. 2, pp. 1–22.

Liotta, L.A., et al., *Ann. Rev. Biochem.* (1986), "Biochemical Interactions of Tumor Cells with the Basement Membrane", vol. 55, pp. 1037–1057.

Kerwar, S.S., et al., *Advances in Inflammation Research* (1986), "Inhibitors of Connective–Tissue Breakdown and their Use in Inflammatory Disease", vol. 11, pp. 159–171.

Mainardi, C.L., et al., *Advances in Inflammation Research* (1986), "Type–Specific Collagenolysis", vol. 11, pp. 135–144.

Turpeenniemi–Hujanen, T., et al., *Annual Reports in Medicinal Chemistry* (1984), "Collagenases in Tumor Cell Extravasation", Chapter 23, pp. 231–239.

Liotta, L.A., et al., *Cancer Metastasis Reviews 1* (1982), "Role of Collagenases in Tumor Cell Invasion", pp. 277–288.

Manabe, R., et al., *Int. Congr. Ser.—Excerpta Med.* (1982), "Collagenase in Eye Diseases", vol. 61, pp. 231–240.

Harper, E., et al., *Ann. Rev. Biochem.* (1980), "Collagenases", vol. 49, pp. 1063–1078.

* cited by examiner

MATRIX METALLOPROTEASE INHIBITORS

CROSS-REFERENCE TO RELATED APPLICATIONS

This application is a divisional of 08/343,158 filed Nov. 22, 1994, now U.S. Pat. No. 6,037,472, which is a continuation-in-part of Ser. No. 08/147,811, filed Nov. 4, 1993, now abandoned incorporated herein by reference.

FIELD OF THE INVENTION

The present invention is directed to compounds and their pharmaceutically acceptable salts, which inhibit matrix metalloproteases, and are therefore useful in the treatment of mammals having disease-states alleviated by the inhibition of such matrix metalloproteases.

BACKGROUND OF THE INVENTION

Matrix metalloproteases ("MMPs)" are a family of proteases (enzymes) involved in the degradation and remodeling of connective tissues. Members of this family of endopeptidase enzymes are present in various cell types that reside in or are associated with connective tissue, such as fibroblasts, monocytes, macrophages, endothelial cells, and invasive or metastatic tumor cells. MMP expression is stimulated by growth factors and cytokines in the local tissue environment, where these enzymes act to specifically degrade protein components of the extracellular matrix, such as collagen, proteoglycans (protein core), fibronectin and laminin. These ubiquitous extracellular matrix components are present in the linings of joints, interstitial connective tissues, basement membranes, and cartilage. Excessive degradation of extracellular matrix by MMPs is implicated in the pathogenesis of many diseases, including rheumatoid arthritis, osteoarthritis, periodontal disease, aberrant angiogenesis, tumor invasion and metastasis, corneal ulceration, and in complications of diabetes. MMP inhibition is, therefore, recognized as a good target for therapeutic intervention.

The MMPs share a number of properties, including zinc and calcium dependence, secretion as zymogens, and 40–50% amino acid sequence homology. The MMP family includes collagenases, stromelysins, gelatinases, and matrilysin, as discussed in greater detail below.

Interstitial collagenases catalyze the initial and rate-limiting cleavage of native collagen types I, II, III and X. Collagen, the major structural protein of mammals, is an essential component of the matrix of many tissues, for example, cartilage, bone, tendon a skin. Interstitial collagenases are very specific matrix metalloproteases which cleave collagen to give two fragments which spontaneously denature at physiological temperatures and therefore become susceptible to cleavage by less specific enzymes. Cleavage by the collagenase results in the loss of structural integrity of the target tissue, essentially an irreversible process.

The gelatinases include two distinct, but highly related, enzymes: a 72-kD enzyme secreted by fibroblasts and a wide variety of other cell types, and a 92-kD enzyme released by mononuclear phagocytes, neutrophils, corneal epithelial cells, tumor cells, cytotrophoblasts and keratinocytes. These gelatinases have been shown to degrade gelatins (denatured collagens), collagen types IV (basement membrane) and V, fibronectin and insoluble elastin.

The stromelysins (1 and 2) have been shown to cleave a broad range of matrix substrates, including laminin, fibronectin, proteoglycans, and collagen types IV and IX in their non-helical domains.

Matrilysin (putative metalloprotease or PUMP) is a recently described member of the matrix metalloprotease family. Matrilysin has been shown to degrade a wide range of matrix substrates including proteoglycans, gelatins, fibronectin, elastin, and laminin. Its expression has been documented in mononuclear phagocytes, rat uterine explants and sporadically in tumors.

Inhibitors of MMPs provide useful treatments for diseases associated with the excessive degradation of extracellular matrix, such as arthritic diseases (rheumatoid arthritis and osteoarthritis), bone resorptive diseases (such as osteoporosis), the enhanced collagen destruction associated with diabetes, periodontal disease, corneal ulceration, ulceration of the skin, tumor invasion and metastasis, and aberrant angiogenesis.

The design and uses of MMP inhibitors is described, for example, in *J. Enzyme Inhibition* (1987), Vol. 2, pp. 1–22; *Drug News & Prospectives* (1990), Vol. 3, No. 8, pp. 453–458; *Arthritis and Rheumatism* (1993), Vol. 36, No. 2, pp. 181–189; *Arthritis and Rheumatism* (1991), Vol. 34, No. 9, pp. 1073–1075; *Seminars in Arthritis and Rheumatism* (1990), Vol. 19, No. 4, Supplement 1 (February), pp. 16–20; *Drugs of the Future* (1990), Vol. 15, No. 5, pp. 495–508; and *J. Enzyme Inhibition* (1987), Vol. 2, pp. 1–22. MMP inhibitors are also the subject of various patents and patent applications, for example, U.S. Pat. No. 5,189,178 (Galardy) and U.S. Pat. No. 5,183,900 (Galardy), European Published Patent Applications 0 438 223 (Beecham) and 0 276 436 (F. Hoffmann-La Roche), and Patent Cooperation Treaty International Applications 92/21360 (Merck), 92/06966 (Beecham) and 92/09563 (Glycomed).

SUMMARY OF THE INVENTION

The invention provides new compounds which are useful as inhibitors of matrix metalloproteases and which are effective in treating disease-states characterized by excessive activity of matrix metalloproteases.

Accordingly, one aspect of the invention is directed to compounds of formula (I):

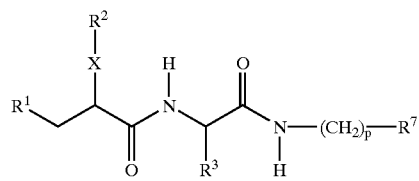

wherein:

$R^1$ is mercapto, acetylthio, carboxy, hydroxycarbamoyl, N-hydroxyformamide, alkoxycarbonyl, aryloxycarbonyl, aralkoxycarbonyl, benzyloxycarbamoyl or a group of the formula

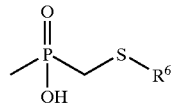

where $R^6$ is aryl or heteroaryl;

$R^2$ is alkyl, cycloalkyl, aryl, heterocycloalkyl, or heteroaryl;

$R^3$ is alkyl, cycloalkyl, aralkyl, or heteroaralkyl;

$R^7$ is aryl, heteroaryl or heterocycloalkyl;

X is a group of the formula —$(CH_2)_m$—Y—$(CH_2)_n$—, where:

Y is O, S, or a single bond,
m is an integer from 0 to 4,
n is an integer from 0 to 4, and
m+n is an integer from 0 to 4;
p is an integer from 0 to 4, provided that $R^2$—X is biphenylalkyl when
p is not 0;
and the pharmaceutically acceptable salts thereof.

Another aspect of the invention provides processes for synthesizing the compounds and salts of formula (I).

In another aspect, the invention is directed to a sub-genus of formula (I), i.e., the compounds of formula (II), as follows:

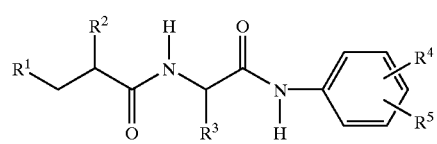

formula (II)

wherein:
$R^1$ is mercapto, acetylthio, carboxy, hydroxycarbamoyl, alkoxycarbonyl, aryloxycarbonyl, aralkoxycarbonyl, benzyloxyaminocarbonyl or a group of the formula

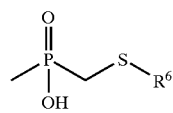

where $R^6$ is aryl or heteroaryl;
$R^2$ is alkyl, aralkyl or cycloalkylalkyl;
$R^3$ is cycloalkyl, alkyl (optionally substituted by cycloalkyl, hydroxy, mercapto, alkylthio, aralkoxy, carboxy, amino, alkylamino, guanidino, carbamoyl, pyridinyl or indolyl), or aralkyl (optionally substituted by hydroxy, carboxy, alkyl or alkoxy);
$R^4$ is nitro, amino, cyano, hydroxy, alkoxy, carboxy, alkoxycarbonyl, alkylsulfonyl, haloalkyl, alkoxycarbonylalkyl, tetrazolyl, carbamoyl (optionally substituted by alkyl or dialkylaminoalkyl), or aminosulfonyl (optionally substituted by alkyl); and
$R^5$ is hydrogen, halo or hydroxy,
as a single stereoisomer or as a mixture thereof; and the pharmaceutically acceptable salts thereof.

Another aspect of the invention is directed to compounds of the formula

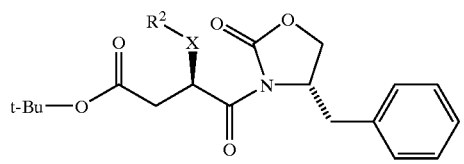

wherein:
$R^2$ is alkyl, aryl or heteroaryl; and
X is a group of the formula —$(CH_2)_m$—Y—$(CH_2)_n$—, where:
Y is O, S, or a single bond,
m is an integer from 0 to 4,
n is an integer from 0 to 4, and
m+n is an integer from 0 to 4;

or $R^2$ and X together are lower alkenyl.

Another aspect of the invention is directed to processes for synthesizing a compound of the formula

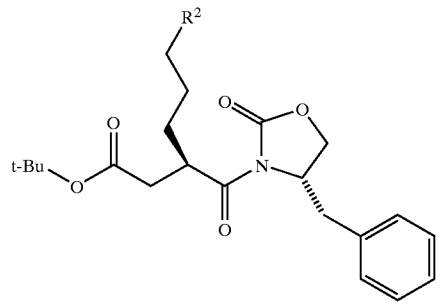

wherein $R^2$ is aryl or heteroaryl, by
(a) hydrogenating a compound of the formula:

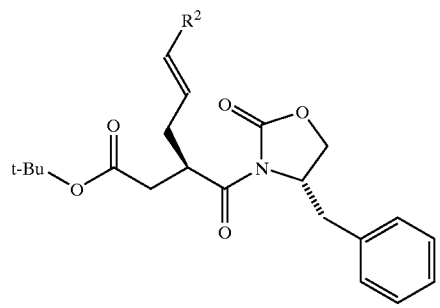

in the presence of a palladium/carbon catalyst; or
(b) contacting a compound of the formula

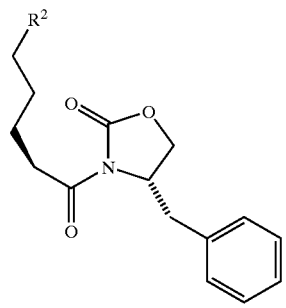

with sodium hexamethyldisilazide and t-butylbromoacetate.

Other aspects of the invention are directed to compounds of the formula

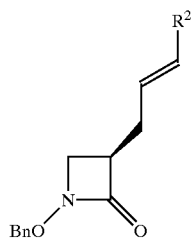

wherein $R^2$ is aryl or heteroaryl, and a process for synthesizing these compounds by (a) contacting a compound of the formula:

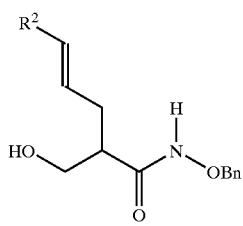

where R² is hydrogen, aryl or heteroaryl, with an excess of mesyl chloride in pyridine followed by refluxing under basic conditions, and (b) where R² is hydrogen in step (a), reacting the product of step (a) with an aryl halide or a heteroaryl halide in the presence of a base and a palladium catalyst.

Another aspect of the invention is directed to methods of inhibiting matrix metalloprotease activity in a mammal, which methods comprise administering to the mammal in need thereof a therapeutically effective amount of a compound of formula (I) as defined above, as a single stereoisomer, or as a mixture thereof, or a pharmaceutically acceptable salt thereof.

Another aspect of the invention is directed to a pharmaceutical composition useful in inhibiting matrix metalloprotease activity in a mammal, which composition comprises a therapeutically effective amount of a compound of formula (I) as defined above, as a single stereoisomer or as a mixture thereof; or a pharmaceutically acceptable salt thereof; and a pharmaceutically acceptable excipient.

DETAILED DESCRIPTION OF THE INVENTION

Definitions

As used in the specification and appended claims, unless specified to the contrary, the following terms have the meaning indicated:

"BOC" refers to t-butoxycarbonyl.

"CBZ" refers to benzyloxycarbonyl (carbobenzyloxy).

"DCC" refers to N,N-dicyclohexylcarbodiimide.

"DMAP" refers to N,N-dimethylaminopyridine.

"DMF" refers to N,N-dimethylformamide.

"EDCI" refers to N-ethyl-N'-(3-dimethylaminopropyl)-carbodiimide.

"HOBT" refers to 1-hydroxybenzotriazole.

"Hydroxy" refers to the radical —OH.

"Amino" refers to the radical —NH₂.

"Acetylthio" refers to the radical —SC(O)CH₃.

"Halo" refers to bromo, chloro or fluoro.

"Carbamoyl" refers to the radical —C(O)NH₂.

"Carboxy" refers to the radical —C(O)OH.

"Hydroxyamino" refers to the radical —NHOH.

"Hydroxycarbamoyl" refers to the radical —C(O)NHOH.

"N-Hydroxyformamide" refers to the radical —N(OH)C(O)H

"Benzyloxycarbamoyl" refers to —C(O)N(H)OCH₂C₆H₅.

"Acylamide" refers to —NHC(O)R$_a$ where R$_a$ is alkyl.

"Mercapto" refers to the radical —SH.

"Alkyl" refers to a straight or branched chain monovalent radical consisting solely of carbon and hydrogen, containing no unsaturation and having from one to ten carbon atoms, e.g., methyl, ethyl, n-propyl, 2-methylpropyl (iso-butyl), 1-methylethyl (iso-propyl), n-butyl, and 1,1-dimethylethyl (t-butyl), heptyl and the like, which can be optionally substituted by cycloalkyl, hydroxy, mercapto, alkylthio, aralkoxy, carboxy, amino, mono- and di-alkylamino, guanidino, N,N-dialkylguanidino, carbamoyl, aryl, and heteroaryl.

"Alkanyl" or "alkylene" refers to a straight chain divalent radical consisting solely of carbon and hydrogen, containing no unsaturation and having from one to five carbon atoms, e.g., methylene, ethylene, propylene (or propanyl) and the like.

"Lower alkenyl" refers to a straight chain univalent hydrocarbon radical having from two to six carbon atoms and containing at least one unsaturated bond, e.g., prop-2-enyl, pent-4-enyl and the like.

"Alkylamino" refers to a radical of the formula —NHR$_a$ where R$_a$ is alkyl as defined above, e.g., methylamino, ethylamino, iso-propylamino, n-butylamino, and the like.

"Haloalkyl" refers to a radical of the formula —R$_a$R$_d$ where R$_a$ is alkyl as defined above substituted by one or more halo groups (R$_d$) as defined above, e.g., 2-chloroethyl, 2-bromoethyl, trifluoromethyl, and the like.

"Dialkylaminoalkyl" refers to a radical of the formula —R$_a$N(R$_a$)$_2$ where each R$_a$ is independently an alkyl radical as defined above, e.g., dimethyl-aminoethyl, diethylamino-n-propyl, dimethylamino-n-propyl, and the like.

"Aminosulfonyl" refers to —S(O)₂NH₂.

"Alkylsulfonyl" refers to a radical of the formula —S(O)₂R$_a$ where R$_a$ is alkyl as defined above, e.g., methylsulfonyl, ethylsulfonyl, iso-propylsulfonyl, and the like.

"Alkylsulfinyl" refers to a radical of the formula —S(O)R$_a$ where R$_a$ is alkyl as defined above.

"Alkylthio" refers to a radical of the formula —SR$_a$ where R$_a$ is optionally-substituted alkyl as defined above, e.g., methylthio, ethylthio, iso-propylthio, n-butylthio, and the like.

"Alkoxy" refers to a radical of the formula —OR$_a$ wherein R$_a$ is alkyl as defined above, e.g., methoxy, ethoxy, n-propoxy, 1-methylethoxy, n-butoxy, t-butoxy, and the like.

"Alkoxycarbonylalkyl" refers to a radical of the formula —R$_a$C(O)R$_b$ where R$_a$ is alkyl as defined above and R$_b$ is alkoxy as defined above, e g., methoxycarbonylethyl, ethoxycarbonylethyl, methoxycarbonyl-iso-propyl, and the like.

"Aryl" refers to a monovalent unsaturated aromatic carbocyclic radical having a single ring (e.g., phenyl), two condensed rings (e.g., naphthyl) or three condensed rings (e.g., phenanthrenyl or fluorenyl) which can be optionally substituted by one or more substituents independently selected from: alkyl, hydroxy, carboxy, halo, cyano, amino, nitro, tetrazolyl, heteroaryl, aminoalkoxy, alkylthio, haloalkyl, alkoxy, alkoxycarbonyl, alkoxycarbonylalkyl, alkyl sulfonyl, alkyl sulfinyl, aminosulfonyl optionally substituted by alkyl, carbamoyl optionally substituted by alkyl or dialkylaminoalkyl, or the substituent can be another aryl group as defined herein (e.g., to form an optionally substituted biphenyl radical).

"Aryloxy" refers to a radical of the formula —OR$_b$ wherein R$_b$ is aryl as defined above, e.g., phenoxy, quinol-2-yloxy, naphth-1-yloxy, or naphth-2-yloxy.

"Aralkyl" refers to a radical of the formula —R$_a$R$_b$ wherein R$_a$ is alkyl as defined above and R$_b$ is aryl as defined above, e.g., benzyl, phenylethylene, 3-phenylpropyl, and the like.

"Aralkoxy" refers to a radical of the formula —OR$_a$R$_b$ wherein R$_a$ is alkyl as defined above and R$_b$ is aryl as defined above, e.g., benzyloxy, 3-naphth-2-ylpropoxy, and the like.

"Alkoxycarbonyl" refers to a radical of the formula —C(O)$R_b$ wherein $R_b$ is alkoxy as defined above, e.g., methoxycarbonyl, ethoxycarbonyl, t-butoxycarbonyl, and the like.

"Aralkoxycarbonyl" refers to a radical of the formula —C(O)$R_c$ wherein $R_c$ is aralkoxy as defined above, e.g., benzyloxycarbonyl, and the like.

"Cycloalkyl" refers to a monovalent ring radical consisting solely of carbon and hydrogen atoms, containing no unsaturation and having from five to seven carbon atoms, e.g., cyclopentyl, cyclohexyl and cycloheptyl.

"Cycloalkylalkyl" refers to a radical of the formula —$R_c R_a$ where $R_a$ is alkyl as defined above and $R_c$ is cycloalkyl as defined above, e.g., cyclohexylmethyl, cyclohexylethyl, cyclopentylmethyl, and the like.

"Heteroaryl" refers to a monovalent unsaturated aromatic carbocyclic radical having a single ring or multiple condensed rings with at least one heteroatom such as N,O,S, (e.g., pyridyl, quinolyl, indolyl, carbazolyl, dibenzofuranyl, dibenzothiophenyl, phenanthridinyl), which can be optionally substituted by one or more substituents independently selected from: alkyl, hydroxy, carboxy, halo, cyano, amino, nitro, tetrazolyl, aryl, aminoalkoxy, alkylthio, haloalkyl, alkoxy, alkoxycarbonyl, alkoxycarbonylalkyl, alkyl sulfonyl, alkyl sulfinyl, aminosulfonyl optionally substituted by alkyl, and carbamoyl optionally substituted by alkyl or dialkylaminoalkyl.

"Heteroaralkyl" refers to a radical of the formula —$R_a R_b$ where $R_a$ is alkyl as defined above and $R_b$ is heteroaryl as defined above.

"Heterocycloalkyl" refers to a monovalent saturated carbocyclic radical having a single ring or multiple condensed rings with at least one heteroatom such as N,O,S (e.g., morpholino, piperazinyl, piperidinyl, pyrrolidinyl).

"Optional" or "optionally" means that the subsequently described event of circumstances may or may not occur, and that the description includes instances where said event or circumstance occurs and instances in which it does not. For example, "optionally substituted quinol-2-yl" means that the quinol-2-yl radical may or may not be substituted and that the description includes both substituted quinol-2-yl radicals and quinol-2-yl radicals having no substitution.

"Amino-protecting group" as used herein refers to those organic groups intended to protect nitrogen atoms against undesirable reactions during synthetic procedures, and includes, but is not limited to, benzyl, acyl, acetyl, benzyloxycarbonyl (carbobenzyloxy), p-methoxybenzyloxycarbonyl, p-nitrobenzyloxycarbonyl, t-butoxycarbonyl, trifluoroacetyl, and the like.

"Base" as used here includes both strong bases such as sodium hydroxide, lithium hydroxide, ammonium hydroxide, potassium carbonate and the like, and organic bases such as pyridine, diisopropylethylamine, N-methylmorpholine, triethylamine, dimethylaminopyridine and the like.

"Pharmaceutically acceptable salt" refers to those salts which retain the biological effectiveness and properties of the free bases or free acids and which are not biologically or otherwise undesirable. If the compound exists as a free base, the desired salt may be prepared by methods known to those of ordinary skill in the art, such as treatment of the compound with an inorganic acids such as hydrochloric acid, hydrobromic acid, sulfuric acid, nitric acid, phosphoric acid and the like; or with an organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. If the compound exists as a free acid, the desired salt may also be prepared by methods known to those of ordinary skill in the art, such as the treatment of the compound with an inorganic base or an organic base. Salts derived from inorganic bases include, but are not limited to, the sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like.

"Mammal" includes humans and all domestic and wild animals, including, without limitation, cattle, horses, swine, sheep, goats, dogs, cats, and the like.

"Therapeutically effective amount" refers to that amount of a compound of formula (I) which, when administered to a mammal in need thereof, is sufficient to effect treatment, as defined below, for disease-states alleviated by the inhibition of matrix metalloprotease activity, such as the activity of stromelysin, gelatinase, matrilysin and/or collagenase. The amount of a compound of formula (I) which constitutes a "therapeutically effective amount" will vary depending on the compound, the disease-state and its severity, and the mammal to be treated, but can be determined routinely by one of ordinary skill in the art having regard to his own knowledge and to this disclosure.

"Treating" or "treatment" as used herein cover the treatment of a disease-state in a mammal, particularly in a human, which disease-state is alleviated by the inhibition of matrix metalloprotease activity, such as the activity of stromelysin, gelatinase, matrilysin and/or collagenase, and include:

(i) preventing the disease-state from occurring in a mammal, in particular, when such mammal is predisposed to the disease-state but has not yet been diagnosed as having it;

(ii) inhibiting the disease-state, i.e., arresting its development; or (iii) relieving the disease-state, i.e., causing regression of the disease-state.

"Stereoisomers" refers to compounds having identical molecular formulae and nature or sequence of bonding but differing in the arrangement of their atoms in space.

The compounds of formula (I), or their pharmaceutically acceptable salts, have at least two asymmetric carbon atoms in their structure, and may therefore exist as single stereoisomers, racemates, and as mixtures of enantiomers and diastereomers. All such single stereoisomers, racemates and mixtures thereof are intended to be within the scope of this invention.

When naming the single stereoisomers of compounds of formula (I) an absolute descriptor, R or S, may be assigned to the chiral carbon atoms therein according to the "Sequence Rule" procedure of Cahn, Ingold and Prelog.

Nomenclature

The nomenclature used herein is a modified form of I.U.P.A.C. nomenclature wherein the compounds of the invention are named as peptide derivatives. Where $R^3$ of Formula (I) comprises the side chain of an amino acid residue, that portion of the chemical structure which includes $R^3$ together with the adjacent nitrogen atom (illustrated below and named as the N nitrogen, as opposed to the N' nitrogen) and carbonyl group is given the name of the corresponding amino acid. The naming and numbering of the compounds of the present invention is illustrated below for representative compounds of formula (I).

For example, the following compound of formula (I)

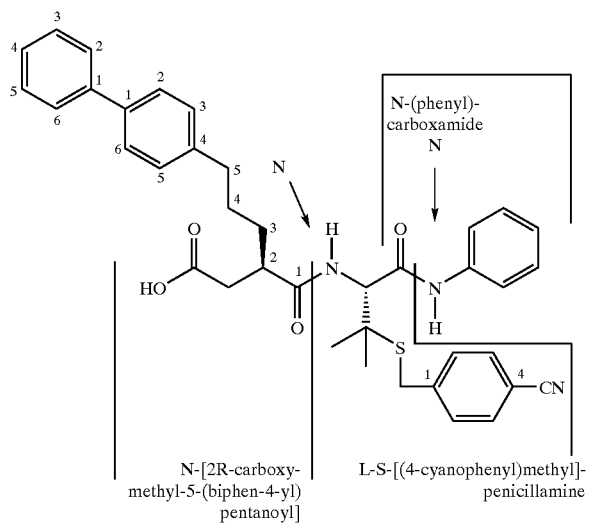

wherein $R^1$ is carboxy; $R^2$ is biphenyl; $R^3$ is 4-(cyano)benzylthioisopropyl; $R^7$ is phenyl; X is propanyl; and p is 0, is named N-(2R-carboxymethyl-5-(biphen-4-yl)pentanoyl)-L-S-((4-cyanophenyl)methyl)-penicillamine-N'-(phenyl)carboxamide. Another name for this compound is N-(5-(biphen-4-yl)-2R-carboxymethylpentanoyl)-L-S-((4-cyanophenyl)methyl)-penicillamine-N'-(phenyl)carboxamide. For ease of reference, the portions of the structure are associated with their corresponding nomenclature.

The structures and names of several other representative compounds of formula (I) follow.

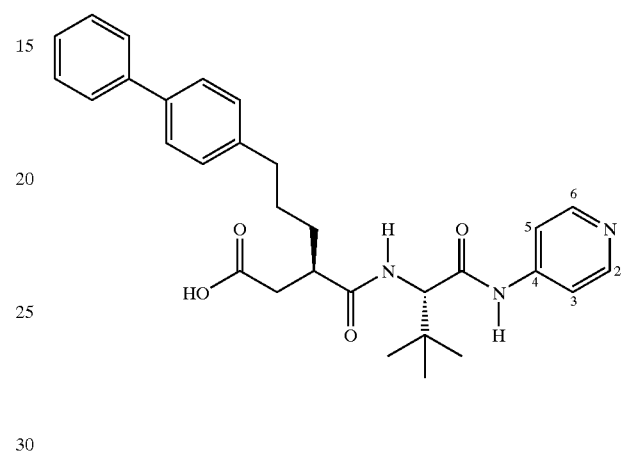

The above compound is named N-(2R-carboxymethyl-5-(biphen-4-yl)pentanoyl)-L-t-butylglycine-N'-(pyrid-4-yl)carboxamide. The term t-leucine can be interchanged with t-butylglycine, and the term pyridinyl can be interchanged with pyridyl. Another name for the above compound is: N-(5-biphen-4-yl-2R-carboxymethylpentanoyl)-L-t-leucine-N'-(pyridin-4-yl)carboxamide.

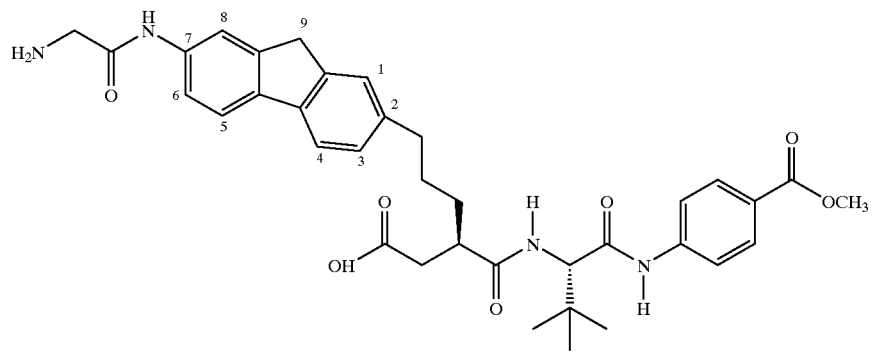

The above compound is named N-(2R-carboxymethyl-5-(7-(glycyl)aminofluoren-2-yl)pentanoyl)-L-leucine-N'-(4-(methoxycarbonyl)phenyl)carboxamide. Another name for this compound is N-(5-(7-(glycyl)aminofluoren-2-yl)-2R-carboxymethylpentanoyl)-L-leucine-N'-(4-methoxycarbonylphenyl)carboxamide.

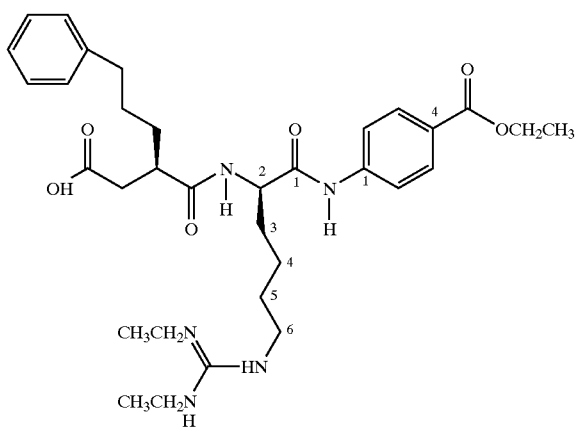

The above compound is named N-(2R-carboxymethyl-5-(phenyl)pentanoyl-L-6-(N,N'-diethylguanido)lysyl-N'-(4-(ethoxycarbonyl)phenyl)carboxamide. The term guanidino can be used interchangeably with guanido. Another name for this compound is N-(5-phenyl-2R-carboxymethyl-pentanoyl)-L-6-(N,N'-diethylguanidino)-lysyl-N'-(4-ethoxycarbonylphenyl)carboxamide.

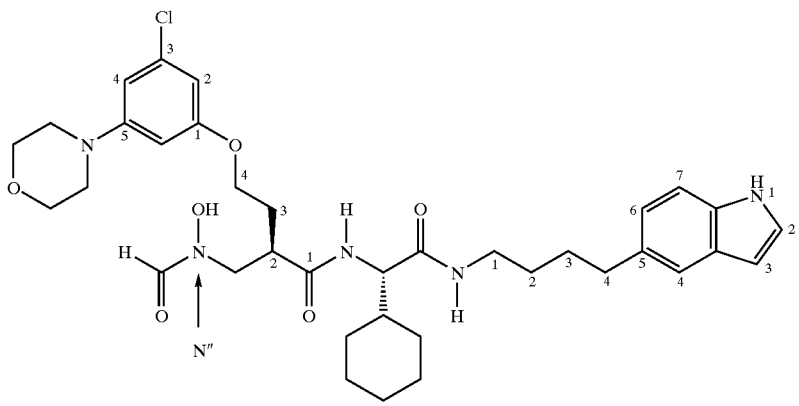

The above compound is named N-(2R-(N''-formyl-N''-hydroxyamino)methyl-4-((3-chloro,5-morpholino)phen-1-yl)oxybutanoyl)-L-cyclohexylglycine-N'-(4-(indol-5-yl)butyl)carboxamide. Another name for this compound is N-(4-((3-chloro,5-morpholino)phen-1-yl)-2R-(N''-formyl-N''-hydroxyamino)methyloxybutanoyl)-L-cyclohexylglycine-N'-(4-(indol-5-yl)butyl)carboxamide.

Utility, Testing and Administration

Utility

The compounds of formula (I) inhibit mammalian matrix metalloproteases, such as the stromelysins, gelatinases, matrilysin and collagenases, and are therefore useful for treating diseases associated with the MMP-induced excessive degradation of matrix and connective tissue within the mammal, for example, arthritic diseases (rheumatoid arthritis and osteoarthritis), bone resorptive diseases (such as osteoporosis), the enhanced collagen destruction associated with diabetes, periodontal disease, corneas ulceration, ulceration of the skin, tumor invasion and metastasis, and aberrant angiogenesis.

Testing

The ability of the compounds of formula (I) to inhibit matrix metalloprotease activity, such as the activity of stromelysin, gelatinase, matrilysin and/or collagenase may be demonstrated by a variety of in vitro and in vivo assays known to those of ordinary skill in the art, such as the assay described in *Anal. Biochem.* (1985), Vol. 147, p. 437, and the MMP Enzymatic Assay described in *FEBS* (1992), Vol. 296(3), p. 263, or modifications thereof.

Administration

Administration of the compounds of formula (I), or their pharmaceutically acceptable salts, in pure form or in an appropriate pharmaceutical composition, can be carried out via any of the accepted modes of administration or agents for serving similar utilities. Thus, administration can be, for example, orally, nasally, parenterally, topically, transdermally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of formula (I) as the/an active agent, and, in addition, may include other medicinal agents, pharmaceutical agents, carriers, adjuvants, etc.

Generally, depending on the intended mode of administration, the pharmaceutically acceptable compositions will contain about 1% to about 99% by weight of a compound(s) of formula (I), or a pharmaceutically acceptable salt thereof, and 99% to 1% by weight of a suitable pharmaceutical excipient. Preferably, the composition will be about 5% to 75% by weight of a compound(s) of formula (I), or a pharmaceutically acceptable salt thereof, with the rest being suitable pharmaceutical excipients.

The preferred route of administration is oral, using a convenient daily dosage regimen which can be adjusted according to the degree of severity of the disease-state to be treated. For such oral administration, a pharmaceutically acceptable composition containing a compound(s) of formula (I), or a pharmaceutically acceptable salt thereof, is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such compositions take the form of solutions, suspensions, tablets, pills, capsules, powders, sustained release formulations and the like.

Preferably such compositions will take the form of capsule, caplet or tablet and therefore will also contain a diluent such as lactose, sucrose, dicalcium phosphate, and the like; a disintegrant such as croscarmellose sodium or derivatives thereof; a lubricant such as magnesium stearate and the like; and a binder such as a starch, gum acacia, polyvinylpyrrolidone, gelatin; cellulose ether derivatives, and the like.

The compounds of formula (I), or their pharmaceutically acceptable salts, may also be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%).

Liquid pharmaceutically administrable compositions can, for example, be prepared by dissolving, dispersing, etc., a compound(s) of formula (I) (about 0.5% to about 20%), or a pharmaceutically acceptable salt thereof, and optional pharmaceutical adjuvants in a carrier, such as, for example, water, saline, aqueous dextrose, glycerol, ethanol and the like, to thereby form a solution or suspension.

If desired, a pharmaceutical composition of the invention may also contain minor amounts of auxiliary substances such as wetting or emulsifying agents, Ph buffering agents, antioxidants, and the like, such as, for example, citric acid, sorbitan monolaurate, triethanolamine oleate, butylated hydroxytoluene, etc.

Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of formula (I), or a pharmaceutically acceptable salt thereof, for treatment of a disease-state alleviated by the inhibition of matrix metalloprotease activity in accordance with the teachings of this invention.

The compounds of formula (I), or their pharmaceutically acceptable salts, are administered in a therapeutically effective amount which will vary depending upon a variety of factors including the activity of the specific compound employed, the metabolic stability and length of action of the compound, the age, body weight, general health, sex, diet, mode and time of administration, rate of excretion, drug combination, the severity of the particular disease-state, and the host undergoing therapy.

Generally, a therapeutically effective daily dose is from about 0.14 mg to about 14.3 mg/kg of body weight per day of a compound of formula (I), or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of formula (I), or a pharmaceutically acceptable salt thereof, preferably from about 50 mg to about 700 mg per day, and most preferably from about 100 mg to about 500 mg per day.

Preferred Embodiments

Preferred are the compounds of formula (I) where X is alkanyl and where p is zero, 2 or 3.

Of the compounds where p is 2 or 3, particularly preferred are those compounds where $R^1$ is carboxy, $R^2$ is biphenyl, $R^3$ is cyclohexyl, and $R^7$ is optionally substituted phenyl [especially 4-(aminosulfonyl)phenyl] or N-morpholino.

Of the compounds where p is zero, particularly preferred are the group of compounds where $R^2$ is alkyl, optionally substituted phenyl, or a group of the formula:

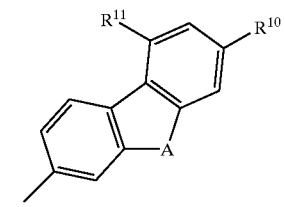

and $R^7$ is 4-pyridyl or optionally substituted phenyl.

Within this group, a preferred subgroup of compounds are those where $R^1$ is carboxy, hydroxycarbamoyl, or N-hydroxyformamide; $R^2$ is phenyl, biphenyl, 4-(pyridyl) phenyl, or 2-methylpropyl; $R^3$ is t-butyl, 4-aminobutyl, alkylaminobutyl, dialkylaminobutyl, 4-(N, N'diethylguanidino)butyl, propyl, 2-methylpropyl, 1-hydroxyisopropyl, 1-hydroxyethyl, or cyclohexyl; and X is a single bond, ethylene or propanyl.

Within this subgroup, a preferred class of compounds are those where $R^2$ is biphenyl, $R^3$ is t-butyl and $R^7$ is 4-pyridyl, particularly where $R^1$ is carboxy, N-hydroxyformamide, or hydroxycarbamoyl.

Also preferred is the subgroup of compounds where $R^2$ is a group of the formula:

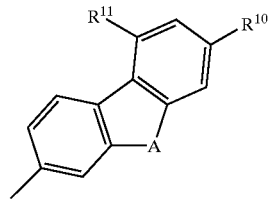

where A is $CH_2$; $R^{10}$ is H or acylamide; $R^{11}$ is H; $R^7$ is optionally substituted phenyl; and X is propanyl.

Within this subgroup, preferred are the compounds where $R^1$ is carboxy, hydroxycarbamoyl, or N-hydroxyformamide; $R^3$ is alkyl (especially 2-methylpropyl); and $R^7$ is alkoxycarbonylphenyl [especially 4-(methoxycarbonyl)phenyl].

Also within this group, preferred are the subgroup of compounds where $R^1$ is carboxy; $R^2$ is phenyl; $R^3$ is alkyl [especially 4-(amino)butyl and 4-(diethylguanidino)N-butyl] or cycloalkyl (especially cyclohexyl); and $R^7$ is optionally substituted phenyl [especially 4-(ethoxycarbonyl) phenyl or 4-(dialkylaminoethylaminosulfonyl)phenyl]; and X is ethylene or propanyl.

Also within this group, preferred are the subgroup of compounds where $R^1$ is mercapto, carboxy, hydroxycarbamoyl, or N-hydroxyformamide; $R^2$ is 2-methylpropyl; $R^3$ is alkyl [especially propyl, 2-methylpropyl], cycloalkyl [especially cyclohexyl] or heteroaralkyl [especially 3-methylindolyl]; $R^7$ is optionally substituted phenyl [especially 4-(methoxy)phenyl, 4-(carboxy)phenyl, 4-(methoxycarbonyl)phenyl or 4-(dimethylaminoethylcarbamoyl)phenyl]; and X is a single bond.

Also within this group, preferred are the subgroup of compounds where $R^1$ is carboxy; $R^2$ is 4-(2-hydroxyethyl) phenyl, 4-(2-hydroxypropyl)-phenyl, 4-(2-hydroxybutyl) phenyl, 4-(pyridyl)phenyl, biphenyl, 4'-(aminoethoxy) biphenyl, 4'-(cyano)biphenyl, or 4'-(hydroxy)biphenyl; $R^3$ is 2-methylpropyl; $R^7$ is 4-(methoxycarbonyl)phenyl; and X is propanyl.

Particularly preferred is the subgroup of compounds where $R^2$ is biphenyl, especially where $R^7$ is optionally substituted phenyl.

Within this particularly preferred subgroup, preferred are the compounds where $R^1$ is carboxy; $R^3$ is alkyl or cycloalkyl [especially cyclohexyl, 4-(amino)butyl, 4-(isopropylamino)butyl, 1-hydroxyisopropyl or t-butyl]; X is propanyl, and $R^7$ is phenyl, 4-(hydroxyethylaminosulfonyl)phenyl, 4-(dimethylaminoethyl-aminosulfonyl) phenyl, 4-(ethoxycarbonyl)phenyl, 4-(N-morpholinopropyl-aminosulfonyl)phenyl, 4-(methylaminosulfonyl)phenyl, 4-(hydroxyethylaminosulfonyl)phenyl, or 4-(methylsulfinyl)phenyl.

Another preferred group, particularly for matrilysin inhibition, are the compounds of formula (II), particularly those compounds wherein $R^1$ is mercapto or acetylthio.

Within this second group, a preferred subgroup of compounds are those compounds wherein $R^2$ is alkyl, aralkyl, cycloalkylalkyl; $R^3$ is cycloalkyl or alkyl (optionally substituted by cycloalkyl, hydroxy, aralkoxy, alkylthio, pyridinyl or indolyl); $R^4$ is cyano, carboxy, hydroxy, alkoxy, alkoxycarbonyl, alkoxycarbonylalkyl, carbamoyl (optionally substituted by aralkylaminoalkyl), or aminosulfonyl (optionally substituted by alkyl); and $R^5$ is hydrogen.

Within this subgroup, a preferred class of compounds are those compounds wherein $R^2$ is alkyl; $R^3$ is cyclohexyl, alkyl (optionally substituted by cyclohexyl, hydroxy, benzyloxy, methylthio, pyridinyl or indolyl); and $R^4$ is carboxy, alkoxycarbonyl and aminosulfonyl.

Within this class of compounds, compounds wherein $R^2$ is 2-methylpropyl are preferred. Particularly preferred are those compounds wherein $R^3$ is 2-methylpropyl.

A third group preferred for matrilysin inhibition, are the compounds of formula (II) wherein $R^1$ is carboxy.

Within this third group, a preferred subgroup of compounds are those compounds wherein $R^2$ is alkyl, aralkyl, cycloalkylalkyl; $R^3$ is cycloalkyl or alkyl (optionally substituted by cycloalkyl, hydroxy, aralkoxy, alkylthio, pyridinyl or indolyl); $R^4$ is cyano, hydroxy, alkoxy, carboxy, alkoxycarbonyl, alkoxycarbonylalkyl, carbamoyl (optionally substituted by aralkylaminoalkyl), or aminosulfonyl (optionally substituted by alkyl); and $R^5$ is hydrogen.

Within this subgroup, a preferred class of compounds are those compounds wherein $R^2$ is alkyl; $R^3$ is cyclohexyl, alkyl (optionally substituted by cyclohexyl, hydroxy, benzyloxy, methylthio, pyridinyl or indolyl); and $R^4$ is carboxy, alkoxycarbonyl and aminosulfonyl.

Within this class of compounds, preferred compounds are those compounds wherein $R^2$ is 2-methylpropyl. Particularly preferred are those compounds wherein $R^3$ is cyclohexyl, 2-methylpropyl, pyridin-3-ylmethyl, 1-benzyloxyethyl, 1-methylpropyl, 1,1-dimethylethyl, 1-hydroxyethyl, and indol-2-ylmethyl; and $R^1$ is methoxycarbonyl.

A fourth group preferred for matrilysin inhibition, are the compounds of formula (II) wherein $R^1$ is hydroxycarbamoyl.

Within this fourth group, a preferred subgroup of compounds are those compounds wherein $R^2$ is alkyl, aralkyl, cycloalkylalkyl; $R^3$ is cycloalkyl or alkyl (optionally substituted by cycloalkyl, hydroxy, aralkoxy, alkylthio, pyridinyl or indolyl); $R^4$ is cyano, hydroxy, alkoxy, carboxy, alkoxycarbonyl, alkoxycarbonylalkyl, carbamoyl (optionally substituted by aralkylaminoalkyl), or aminosulfonyl (optionally substituted by alkyl); and $R^5$ is hydrogen.

Within this subgroup, a preferred class of compounds are those compounds wherein $R^2$ is alkyl; $R^3$ is cyclohexyl, alkyl (optionally substituted by cyclohexyl, hydroxy, benzyloxy, methylthio, pyridinyl or indolyl); and $R^4$ is carboxy, alkoxycarbonyl and aminosulfonyl.

Within this class, preferred compounds are those compounds wherein $R^2$ is 2-methylpropyl. Particularly preferred are those compounds wherein $R^3$ is cyclohexyl, 2-methylpropyl, pyridin-3-ylmethyl, 1-benzyloxyethyl, 1-methylpropyl, 1,1-dimethylethyl, 1-hydroxyethyl, and indol-2-ylmethyl. Presently, the most preferred compounds of formula (I) are the following:

N-(2R-(N"-hydroxycarbamoyl)methyl-4-(methyl)pentanoyl)-L-tryptophan-N'-(4-(carboxy)phenyl)carboxamide, N-(2R-(N"-hydroxycarbamoyl)methyl-4-(methyl)pentanoyl)-L-leucine-N'-(4-(methoxycarbonyl)phenyl)carboxamide;

N-(2R-(N"-hydroxycarbamoyl)methyl-4-(methyl)pentanoyl)-L-leucine-N'-(4-(carboxy)phenyl)carboxamide;

N-(2R-mercaptomethyl-4-(methyl)pentanoyl)-L-leucine-N'-(4-(methoxycarbonyl)phenyl)carboxamide;

N-(2R-acetylthiomethyl-4-(methyl)pentanoyl)-L-leucine-N'-(4-methoxycarbonylphenyl)carboxamide;

N-(2R-carboxymethyl-4-(methyl)pentanoyl)-L-leucine-N'-(4-(methoxycarbonyl)phenyl)carboxamide;

N-(2R-(N"-hydroxycarbamoyl)methyl-4-(methyl)pentanoyl)-L-cyclohexylglycine-N'-(4-(methoxycarbonyl)phenyl)carboxamide;

N-(2R-(N"-hydroxycarbamoyl)methyl-4-(methyl)pentanoyl)-L-t-leucine-N'-(4-(methoxycarbonyl)phenyl)carboxamide;

N-(2R-(N-hydroxycarbamoyl)methyl-5-(biphen-4-yl)pentanoyl-L-t-leucine-N'-(pyrid-4-yl)carboxamide;

N-(2R-carboxymethyl-5-(biphen-4-yl)pentanoyl)-L-t-leucine-N'-(pyridin-4-yl)carboxamide;

N-(2R-carboxymethyl-5-(biphen-4-yl)pentanoyl)-L-t-leucine-N'-(4-((2-hydroxyethyl)aminosulfonyl)phenyl)carboxamide;

N-(2R-carboxymethyl-5-(4-(pyrid-4-yl)phenyl)pentanoyl)-L-leucine-N'-(4-(methoxycarbonyl)phenyl)carboxamide;

N-(2R-carboxymethyl-5-(biphen-4-yl)pentanoyl)-L-β-hydroxyvaline-N'-(phenyl)carboxamide;

N-(N"-formyl-N"-hydroxyamino)methyl-5-(biphen-4-yl)pentanoyl)-L-t-leucine-N'-(pyridin-4-yl)carboxamide;

N-(2R,S)-(N"-formyl-N"-hydroxyamino)methyl-4-(methyl)pentanoyl)-L-leucine-N'-(4-(methoxycarbonyl)phenyl)carboxyamide;

N-(2R-carboxymethyl-5-(biphen-4-yl)pentanoyl)-L-t-leucine-N'-(4R,S-(methylsulfinyl)phenyl)carboxamide;

N-(2R-carboxymethyl-5-(biphen-4-yl)pentanoyl)-L-t-leucine-N'-(4-(methylaminosulfonyl)phenyl)carboxamide;

N-(2R-carboxymethyl-5-(biphen-4-yl)pentanoyl)-L-t-leucine-N'-(4-(3-(morpholin-4-yl)propylaminosulfonyl)phenyl)carboxamide;

N-(2R-carboxymethyl-5-(biphen-4-yl)pentanoyl)-L-cyclohexylglycine-N'-(4-((2-hydroxyethyl)aminosulfonyl)phenyl)carboxamide;

N-(2R-carboxymethyl-5-(biphen-4-yl)pentanoyl)-L-cyclohexylglycine-N'-(4((2-(dimethylamino)ethyl)aminosulfonyl)phenyl)carboxamide;

N-(2R-(N"-hydroxycarbamoyl)methyl-4-(methyl)pentanoyl) D,L-norvaline-N'-(4-(dimethylaminoethyl-carbamoyl)phenyl)carboxamide;

N-(2R-carboxymethyl-5-(biphen-4-yl)pentanoyl)-L-lysine-N'-(4-(ethoxycarbonyl)phenyl)carboxamide;

N-(2R-carboxymethyl-5-(phenyl)pentanoyl)-L-lysine-N'-(4-(ethoxycarbonyl)phenyl)carboxamide;

N-(2R-carboxymethyl-5-(biphen-4-yl)pentanoyl)-L-(Nε-isopropyl)lysine-N'-(4-(ethoxycarbonyl)phenyl)carboxamide;

N-(2R-carboxymethyl)-4-(phenyl)butanoyl)-L-cyclohexylglycine-N'-(4-(N",N"-dimethylaminoethylaminosulfonyl)-phenyl)carboxamide; and N-(2R-carboxymethyl-5-(phenyl)pentanoyl)-L-(N,N'-diethylguanido)lysine-N'-(4-(ethoxycarbonyl)phenyl)carboxamide.

SYNTHESIS OF COMPOUNDS OF FORMULA (I)

The compounds of formula (I) are prepared as described below, for example with reference to Reaction Schemes 1–7, in which the substituent groups illustrated (e.g., $R^1$, $R^2$, etc.) have the same meanings as described in the Summary of the Invention, unless otherwise specified. Certain of the reaction schemes illustrate structures of formula (I) where p is zero and $R^7$ is an optionally substituted phenyl group [the substituents $R^4$ and $R^5$ having been described in connection with formula (II) in the Summary of the Invention). As those skilled in the art will appreciate, while the corresponding compounds where p is 1–4 and where $R^7$ is as otherwise defined can be analogously prepared, combinations of substituents and/or variables in compounds of formula (I) and intermediates thereof are permissible only when such combinations result in stable compounds.

Compounds of formula. (I) and their pharmaceutically acceptable salts, as single stereoisomers or as mixtures thereof, are peptide derivatives all or portions of which can be prepared from the constituent α-amino acid derivative(s). Standard methods for the formation of peptide bonds are illustrated by M. Bodanszky et al., *The Practice of Peptide Synthesis* (1984), Springer-Verlag; M. Bodanszky, *Principles of Peptide Synthesis* (1984), Springer-Verlag; J. P. Greenstein et al., *Chemistry of the Amino Acids* (1961), Vol. 1–3, John Wiley and Sons Inc.; G. R. Pettit, *Synthetic Peptides* (1970), Vol. 1–2, Van Nostrand Reinhold Company.

Synthetic Reaction Parameters

The terms "solvent", "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform, methylene chloride (or dichloromethane), diethyl ether, methanol, pyridine and the like]. Unless specified to the contrary, the solvents used in the reactions of the present invention are inert organic solvents.

The term "q.s." means adding a quantity sufficient to achieve a stated function, such as to bring a solution to a desired volume.

Unless specified to the contrary, the reactions described herein take place at atmospheric pressure within a temperature range from 5° C. to 100° C. (preferably from 10° C. to 50° C.; most preferably at "room" or "ambient" temperature, e.g., 20° C.). Further, unless otherwise specified, the reaction times and conditions are intended to be approximate, e.g., taking place at about atmospheric pressure within a temperature range of about 5° C. to about 100° C. (preferably from about 10° C. to about 50° C.; most preferably about 20° C.) over a period of about 1 to about 10 hours (preferably about 5 hours). Parameters given in the Examples are intended to be specific, not approximate.

Amide couplings used to form the compounds of formula (I) are generally performed by the carbodiimide method with reagents such as dicyclohexylcarbodiimide or N'-ethyl-N'-(3-dimethylaminopropyl)-carbodiimide (EDCI) in the presence of 1-hydroxybenzotriazole (HOBT) in an inert solvent such as dimethylformamide (DMF). Other methods of forming the amide or peptide bond include, but are not limited to synthetic routes via an acid chloride, acyl azide, mixed anhydride or activated ester such as nitrophenyl ester. Typically, solution phase amide couplings with or. without peptide fragments are performed.

The selection of protecting groups for the terminal amino or carboxy groups of compounds used in the preparation of the compounds of formula (I) is dictated in part by the particular amide or peptide coupling conditions, and in part by the amino acid and/or peptide components involved in the coupling. Amino-protecting groups commonly used include those which are well known in the art, e.g., p-methoxybenzyloxycarbonyl, benzyloxycarbonyl (also referred to as carbobenzyloxy or CBZ), p-nitrobenzyloxycarbonyl, t-butoxycarbonyl (BOC), and the like. It is preferred to use either BOC or CBZ as the protecting group for the α-amino group because of the relative ease of its removal by mild acids [e.g., by trifluoroacetic acid (TFA) or hydrochloric acid in ethyl acetate] or by catalytic hydrogenation.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

The individual stereoisomers of compounds of formula (I) may be separated from each other by methods known to those of ordinary skill in the art, e.g., by selective crystallization or by chromatography, and/or by the methods disclosed herein.

Preparation of Formula (E)

Compounds of formula (E) are intermediates used in the preparation of compounds of formula (I), and are prepared as shown in Reaction Scheme 1 wherein $R^{12}$ is mesyl or tosyl:

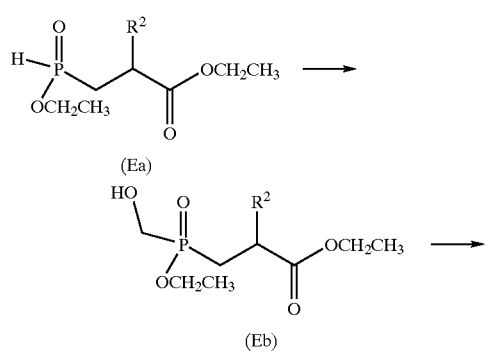

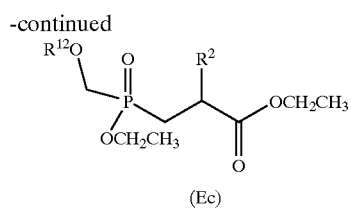

(Ec)

(Ec) + R⁶—SH ⟶
(Ed)

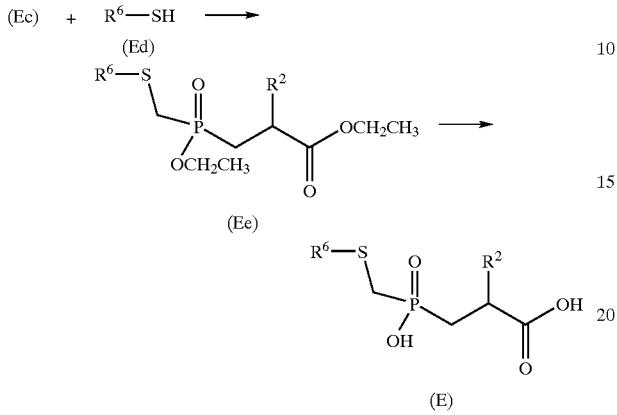

Starting Materials—Compounds of formula (Ea) may be prepared according to methods known to those of ordinary skill in the art (e.g., see European Published Patent Application 0 276 436) or may be prepared according to the method described in Example 1 below. Compounds of formula (Ed) are commercially available or may be prepared according to methods known to those of ordinary skill in the art.

Formula (Eb)—In general, compounds of formula (E) are prepared by first treating a compound of formula (Ea) in an aprotic solvent, preferably tetrahydrofuran and methylene chloride, at 0–15° C., preferably at 0° C., in the presence of a base, preferably diisopropylethylamine and bis-(trimethylsilyl)-acetamide, with paraformaldehyde. The resulting solution is brought to 25–37° C., preferably to 37° C., for 18 hours. The alcohol of formula (Eb) is then isolated by standard methods, preferably by evaporation of solvent, extraction and filtration.

Formula (Ec)—An alcohol of formula (Eb) in an aprotic solvent, preferably methylene chloride, is then cooled to −20° C. to about 0° C., preferably to about −20° C., and is then esterified by the standard procedure of treating the alcohol with at least a stoichiometric amount to about a 100% excess of either mesyl chloride or tosyl chloride. The esterification takes place over an initial period of time (preferably 15 minutes) at −20° C., followed by second period of time (preferably 3.5 hours) at room temperature. The ester of formula (Ec) is then isolated from the reaction mixture by standard isolation procedures, preferably by extraction, filtration and evaporation.

Formula (Ed)—An ester of formula (Ec) in an aprotic solvent, preferably DMF, is then reacted with a salt of a compound of formula (Ed) (preferably the sodium salt formed from the reaction of the compound of formula (Ed) with sodium hydride in an aprotic solvent, preferably DMF), for about 16–20 hours, preferably for about 18 hours, at temperatures beginning at about 0° C. and slowly warming to room temperature. The resulting mercapto compound of formula (Ee) is isolated from the reaction mixture by standard isolation techniques, such as by extraction, evaporation, and flash chromatography.

Formula (E)—A compound of formula (Ee) is then hydrolyzed under basic conditions, preferably in the presence of sodium hydroxide, to form a compound of formula (E), which is isolated from the reaction mixture by standard isolation techniques.

Preparation of Formula (Ia)

Compounds of formula (Ia) are compounds of formula (I) wherein $R^1$ is a group of the formula

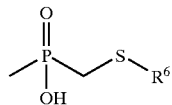

(where, when $R^6$ is aryl it is preferably naphth-1-yl, naphth-2-yl or phenyl, and when $R^6$ is heteroaryl it is preferably pyridyl or quinol-2-yl; $R^2$ is preferably alkyl; and $R^3$ is preferably hydrogen) are prepared as described in Reaction Scheme 2.

Reaction Scheme 2

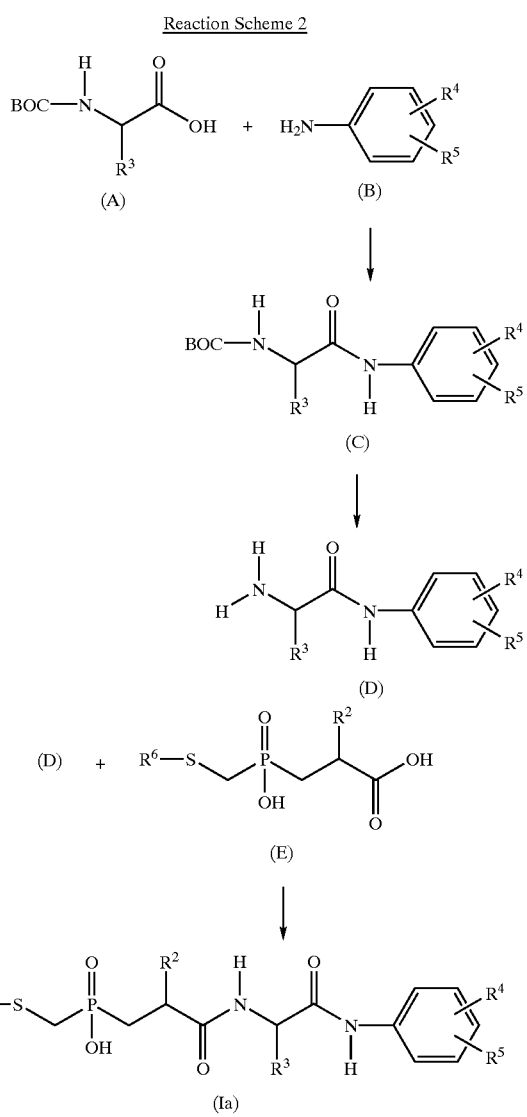

Starting Materials—N-protected amino acids of formula (A) and compounds of formula (B) are commercially available or may be prepared according to methods known to those of ordinary skill in the art. Compounds of formula (E) are prepared as described with reference to Reaction Scheme 1.

Formula (C)—In general, compounds of formula (Ia) are prepared by first coupling a compound of formula (A) with a compound of formula (B) [or with another compound of the formula $H_2N\text{—}(CH_2)_p\text{—}R^7$], under standard amide coupling conditions to form a compound of formula (C). For example, to a cold (0–5° C.) solution of the compound of formula (A) and an excess molar amount of HOBT in DMF is added an excess molar amount of EDCI. The resulting solution is stirred from about 1 to about 2 hours, preferably for about 1 hour, at 0–5° C., preferably at 0° C. To the cold solution is then added a solution of an equimolar amount of a compound of formula (B) in the presence of a base, preferably DMAP. The resulting mixture is stirred from 12 to 24 hours, preferably for 24 hours, at room temperature, preferably at 25° C. The compound of formula (C) is then isolated from the reaction mixture by standard peptide isolation techniques.

Formula (D)—The amino-protecting group of the compound of formula (C) is then removed under mild acidic conditions, preferably in the presence of trifluoroacetic acid, to yield a compound of formula (D).

Alternative Preparations of Formula (D)—Another method of preparing a compound of formula (D) particularly when $R^3$ is t-butyl, other β-branched amino acid side chains, or cyclohexyl, p is zero, and $R^7$ is aryl or heteroaryl, employs the intermediate (A-1), the preparation of which is illustrated in Reaction Scheme 2A. Another alternative method of preparing a compound of formula (D) particularly when $R_3$ is 1-hydroxyisopropyl or another β-hydroxy amino acid side chain, and $R^7$ is aryl or heteroaryl, is illustrated in Reaction Scheme 2B.

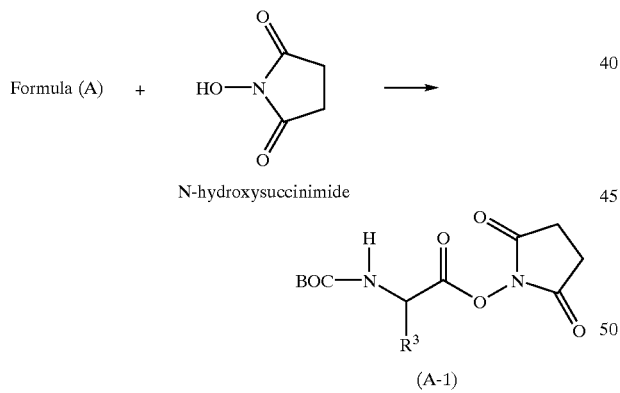

As illustrated in Reaction Scheme 2A, a compound of formula (A) is coupled with about one molar equivalent of N-hydroxysuccinimide in acetonitrile at 0° C. in the presence of DCC. The reaction takes place with stirring at 0° C. to 25° C., for 8 to 16 hours to give the corresponding N-hydroxysuccinimide ester of formula (A-1). This ester is then reacted with a compound of formula B or another compound of the formula $H_2N\text{—}(CH_2)_p\text{—}R^7$ in an inert solvent at 100° C. preferably for 3 hours the resultant compound of formula (C) is isolated and deprotected to yield a compound of formula (D) as described above in Reaction Scheme 2.

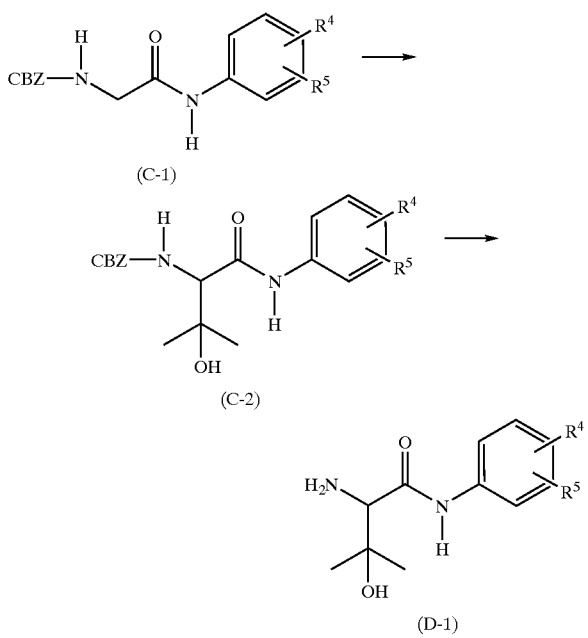

As illustrated in Reaction Scheme 2B, a compound of formula (C-1) in an inert anhydrous solvent such as THF is stirred with n-butyllithium at a temperature below 10° C., preferably 0° C., for about 1 hour, then cooled to about −70° C. and reacted with 3 molar equivalents of acetone. A compound of formula (C-2), as a racemate, is isolated and purified by standard procedures. Following hydrogenolytic removal of the CBZ protecting group, a compound of formula (D-1) is obtained.

Formula (Ia)—As illustrated in Reaction Scheme 2, a compound of formula (D) is coupled with a compound of formula (E) under standard peptide coupling conditions. For example, to a cold (0–5° C., preferably 0° C.) solution of the compound of formula (D) in an inert solvent, preferably THF, is added 1,1'-carbonyldiimidazole. The resulting mixture is stirred from 60 to 90 minutes, preferably for 75 minutes, at 0–5° C., preferably at 0° C., and then reacted with the compound of formula (E) for about 12 to 17 hours, preferably for about 15 hours. The resulting compound of formula (Ia) is then isolated from the reaction mixture by standard peptide isolation techniques, for example, extraction and reverse phase HPLC.

Preparation of Formula (F)

Compounds of formula (F):

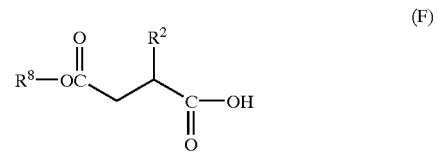

where $R^8$ is t-butyl, are intermediates used in the preparation of compounds of formula (I) as illustrated below in Reaction Scheme 4. The compounds of formula (F) are prepared as shown in Reaction Scheme 3.

23

Reaction Scheme 3

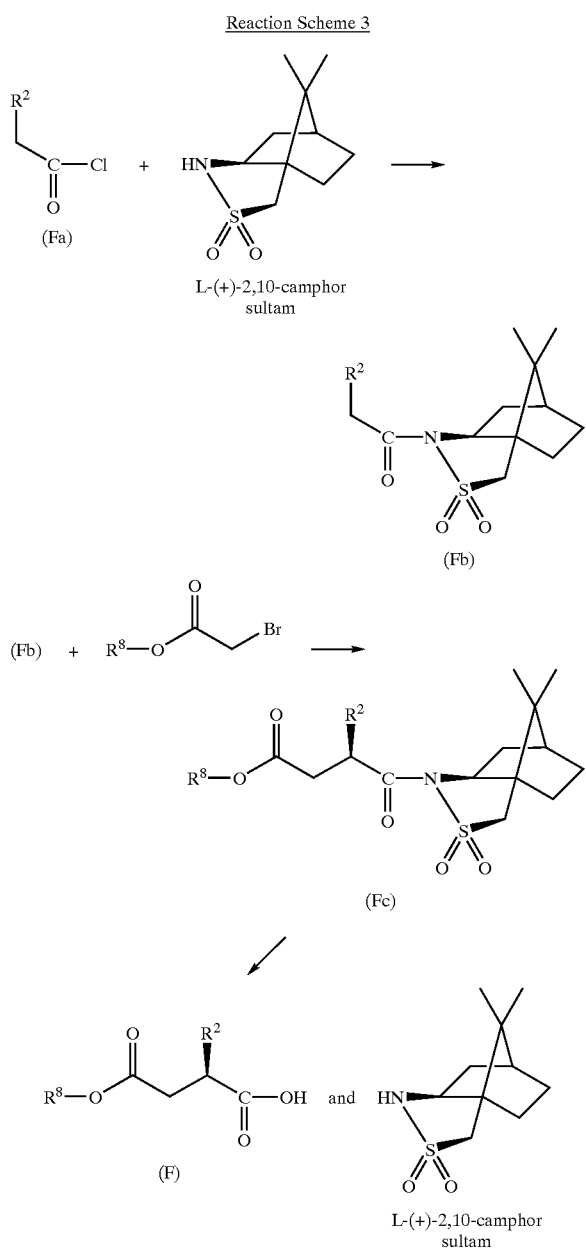

Starting Materials—Compounds of formula (Fa) are commercially available or may be prepared according to methods known to those of ordinary skill in the art, for example, by the method described in Example 11 below. L-(+)-2,10-Camphor sultam and D-(−)-2,10-camphor sultam are commercially available, for example, from Aldrich.

Formula (Fb)—In general, compounds of formula (F) (illustrated as one of the two isomers obtainable by this synthesis) are prepared by first condensing a compound of formula (Fa) [where the group $R^2$ encompasses the group "X" of Formula (I) and can be, e.g., a biphenylpropylene or fluorenyl propylene group] with L-(+)-2,10-camphor sultam to form a compound of formula (Fb).

Formula (Fc)—Using sodium hexamethyldisilazide to generate the anion for 1 hour, the reaction is quenched with t-butylbromoacetate to form the corresponding ester of formula (Fc).

Formula (F)—The camphor group is then removed under basic conditions, such as lithium hydroperoxide (formed in situ from lithium hydroxide and hydrogen peroxide) initially at reduced temperature (preferably 0° C.) for 15 minutes and warmed to room temperature for 2 hours. The mixture is cooled back to 0° C. and an aqueous mixture of sodium sulfite and sodium bicarbonate is added with stirring, after which the mixture is allowed to return to room temperature, and the pH is neutralized to yield an individual stereoisomer of a compound of formula (F) wherein the carbon to which the —X—$R^2$ group is attached is in the (R) configuration. In a similar manner, but substituting D-(−)-2,10-camphor sultam for L-(+)-2,10-camphor sultam, the corresponding individual stereoisomers in the (S) configuration can be prepared.

Alternative Preparation of Formula (F)—Another method of preparing stereoisomers of formula (F) utilizes the commercially available chiral compound, 4S-phenylmethyl-oxazolidinone, as shown below in Reaction Scheme 3A (following the Starting Materials section, where preparation of the compounds of starting material of formula (Fa') are illustrated].

Starting Materials

Compounds of formula (Fa') where X is —O—$CH_2$—$CH_2$— are prepared as illustrated in Reaction Scheme 3A-1.

Reaction Scheme 3A-1

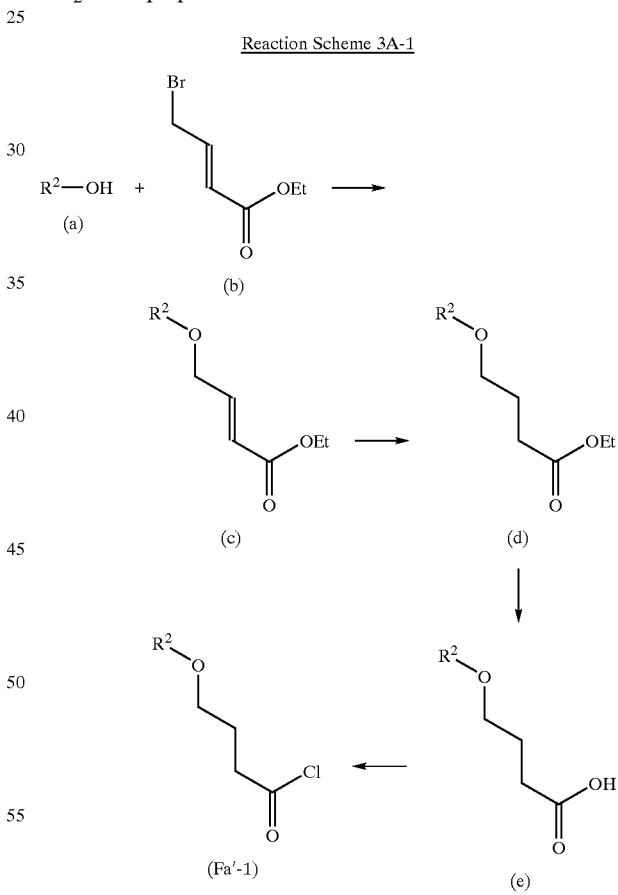

A commercially-available alcohol (a) is reacted with ethyl-4-bromocrotonate (b) in the presence of stoichiometric sodium hydride in a solvent such as DMF at 0° C. to room temperature, or in the case of a phenol (a), by refluxing with (b) in acetone in the presence of excess potassium carbonate for several hours. The resulting unsaturated ester (c) is converted by hydrogenation in the presence of platinum on carbon to the saturated ester (d), which is then saponified with aqueous sodium hydroxide in ethanol to the acid (e). The acid (e) is converted to the acid chloride (Fa'-1) through the action of oxalylchloride at between room temperature and 50° C.

Compounds of formula (Fa') where X is —S—CH$_2$CH$_2$— are prepared as illustrated in Reaction Scheme 3A-2.

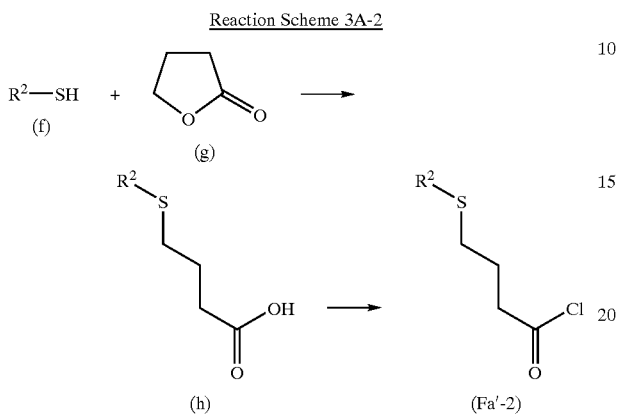

A commercially-available thiol (f) is reacted with lithium hydride in DMF at room temperature for several hours to form the lithium thiolate. Excess butyrolactone (g) is added and heated to reflux under argon to give the acid (h). Acid (h) is then converted to the acid chloride (Fa'-2) with oxalyl chloride, as before.

Compounds of formula (Fa') where X is —CH$_2$CH$_2$—O— are prepared as illustrated in Reaction Scheme 3A-3.

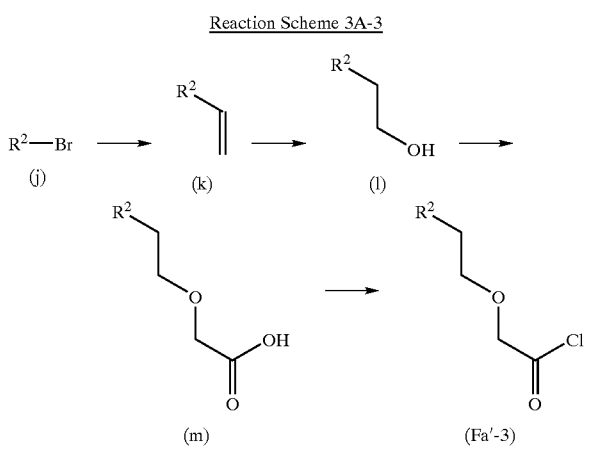

Compounds of formula (l) and (k) are in many cases commercially available. When not, they are prepared as follows. Compounds of formula (j), where R$^2$ is aryl or heteroaryl, are converted to alkenes (k) by treatment for several hours with vinyl-tributylstannane (commercially available from Aldrich Chemical Co.) in the presence of catalytic tetrakis (triphenylphosphine)palladium at reflux in toluene. The alkenes (k) may be further converted to the alcohols (l) by hydroboration with borane in THF at 0° C. to room temperature, over a period of several hours, followed by oxidation with alkaline hydrogen peroxide. The alcohols (l) are converted to the acids (m) by treatment with chloroacetic acid and excess sodium hydride in DMF at elevated temperature, preferably 60° C. The acids (m) are converted to the acid chlorides (Fa'-3) with oxalyl chloride, as before.

Compounds of formula (Fa') where X is —CH$_2$CH$_2$—S— are prepared according to Reaction Scheme 3A-4.

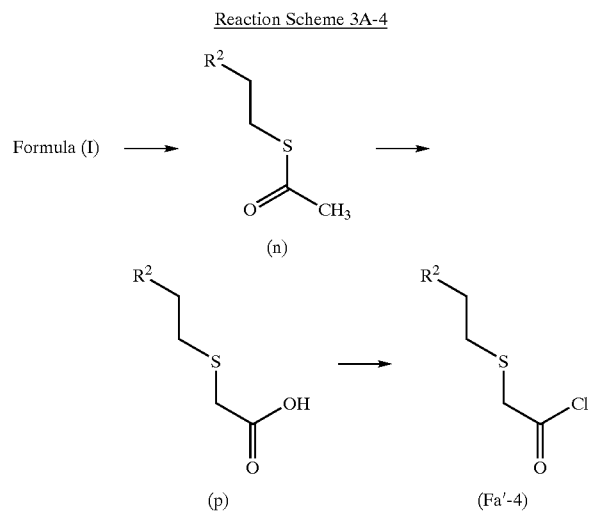

The alcohols (l) are converted to thioacetates (n) by addition of thioacetic acid to the reagent generated from triphosphine and diethyl azodicarboxylate in THF at 0° C. The thioacetates (n) are converted to the acids (p) by treatment with potassium carbonate in methanol in the presence of chloroacetic acid. The acids (p) are converted to the acid chloride (Fa'-4) with oxalyl chloride, as before.

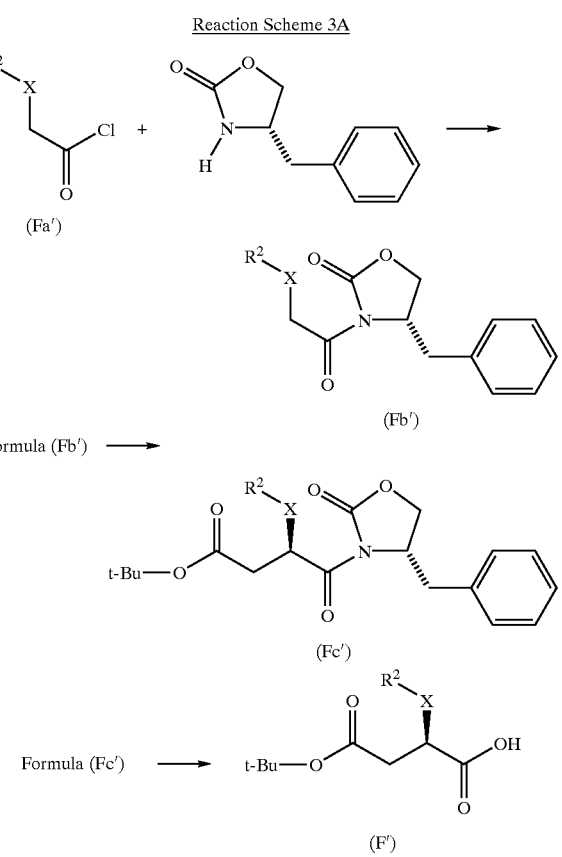

Formula (Fb')—A compound of formula (Fa') is first condensed with 4S-phenylmethyloxazolidinone under standard conditions to give the corresponding compound of formula (Fb').

Formula (Fc')—An approximately equimolar amount of sodium hexamethyldisilazide is added to a compound of formula (Fb') in an inert solvent such as THF. The reaction takes place at −80° C. to −95° C., for about 15 minutes. t-Butylbromoacetate is added in excess to this mixture and the solution is stirred for about 2 hours at −90° C. to −60° C. to yield a single stereoisomer of formula (Fc'), which is purified by standard organic chemistry procedures.

Formula (F')—The oxazolidinone group of a compound of formula (Fc') is removed under basic conditions to yield an individual stereoisomer of formula (F'), for example as described with reference to the preparation of formula (F) in Reaction Scheme 3. The compounds of formula (F') can be used interchangeably with those of formula (F) in the syntheses that follow.

Alternative Preparation of Formula (F)—Formula F can also be prepared as described with reference to Reaction Scheme 3B.

Reaction Scheme 3B

Formula (Fc″) ⟶

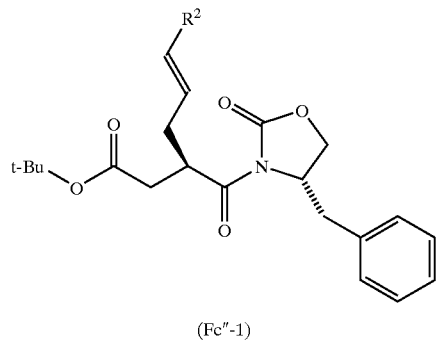

(Fc″-1)

Formula (Fc″-1) ⟶

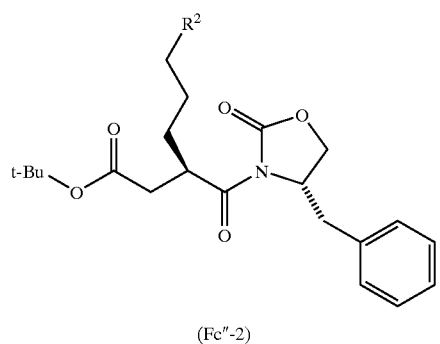

(Fc″-2)

Formula (Fc″-2) ⟶

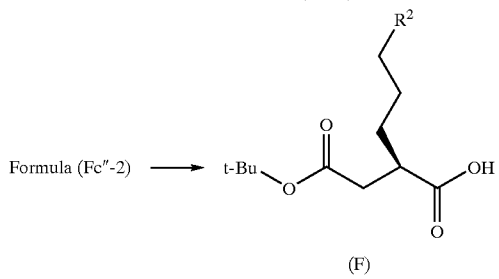

(F)

Starting Materials—The compound illustrated as formula (Fc″) can be prepared analogously to the preparation of formula (Fc') as described with reference to Reaction Scheme 3A, by substituting for the compound of formula (Fa') the corresponding allyl compound where the group shown as X is prop-2-enyl and $R^2$ is H.

Formula (Fc″-1)—Arylation or heteroarylation of (Fc″) is carried out in the presence of a base and a palladium catalyst by adding aryl- or heteroaryl-halide, preferably bromide or iodide, and heating the reaction mixture for about 2 to 4 hours, preferably 4 hours, at about 100° C. to form a compound of the formula (Fc″-1).

Formula (Fc″-2)—Catalytic hydrogenation (Pd/C) of an allyl compound of formula (Fc″-1) yields the corresponding alkyl compound of the formula (Fc″-2).

Formula (F)—A compound of formula (Fc″-2) is subjected to basic conditions, such as lithium hydroperoxide (formed in situ from lithium hydroxide and hydrogen peroxide) initially at reduced temperature (preferably 0° C.) for 15 minutes and warmed to room temperature for 2 hours. The mixture is cooled back to 0° C. and an aqueous mixture of sodium sulfite and sodium bicarbonate is added with stirring, after which the mixture is allowed to return to room temperature, the pH neutralized, and the compound of formula (F) is obtained by standard isolation.

Preparation of Formulae (Ib), (Ic), (Id) and (Ie)

The compounds of formulae (Ib), (Ic), (Id) and (Ie) each represent sub-genuses of formula I in which the $R^1$ substituent varies, prepared sequentially as described in Reaction Scheme 4, where $R^8$ is t-butyl. In compounds of formula (Ib) $R^1$ is alkoxycarbonyl or aralkoxycarbonyl. In compounds of formula (Ic) $R^1$ is carboxy. In compounds of formula (Id) $R^1$ is benzyloxycarbamoyl. In compounds of formula (Ie) $R^1$ is hydroxycarbamoyl.

Reaction Scheme 4

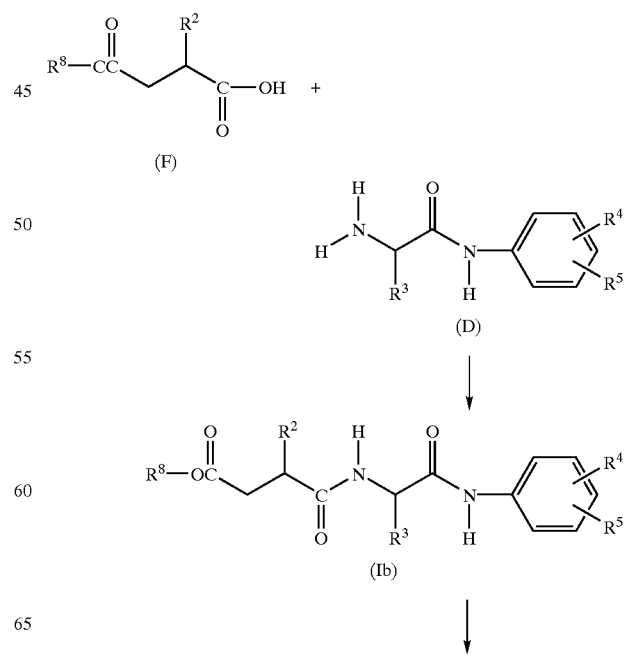

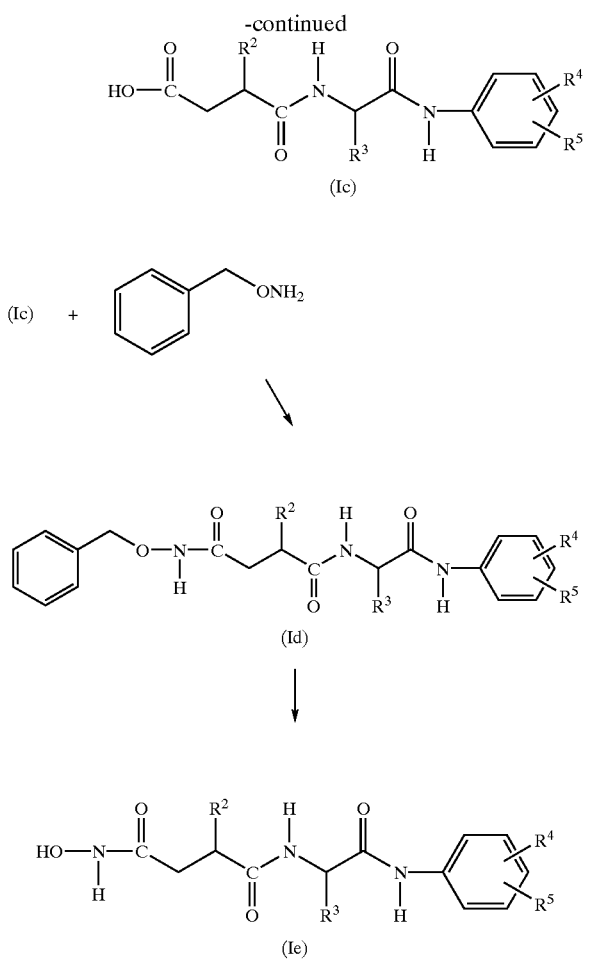

excess molar amount of HOBT, is added an excess molar amount of EDCI. The resulting mixture is stirred from 1 to 2 hours (preferably 1 hour) at 0–5° C. (preferably at 0° C.). To the cold solution is then added an equimolar amount of a compound of formula (D) in the presence of a base, preferably DMAP. The resulting mixture is then stirred from 12 to 24 hours (preferably 24 hours) at room temperature (preferably at 25° C.). The compound of formula (Ib) is then isolated from the reaction mixture by standard peptide isolation techniques, for example, evaporation of solvents, extraction, flash chromatography and/or HPLC.

Formula (Ic)—A compound of formula (Ib) is hydrolyzed under mild acidic conditions, preferably with trifluoroacetic acid, to yield a compound of formula (Ic).

Formula (Id)—A compound of formula (Ic) is then treated with O-benzylhydroxylamine under standard amide coupling conditions to form a compound of formula (Id). For example, a cold (0–5° C.) solution of the compound of formula (Ic) and HOBT in an inert solvent, preferably DMF, is treated with an excess molar amount of EDCI. After stirring the resulting mixture for 30 minutes to an hour at 0–5° C. (preferably at 0° C.), an equimolar amount of O-benzylhydroxyamine is added. The reaction mixture is allowed to warm and remain at room temperature overnight for 8 to 16 hours. The compound of formula (Id) is then isolated from the reaction mixture by standard isolation techniques, for example, by extraction and flash chromatography.

Formula (Ie)—The hydroxyl-protecting group (benzyl) of a compound of formula (Id) is removed under catalytic hydrogenation conditions (Pd/C) to yield a compound of formula (Ie).

Alternative Preparation of Formula (Ie)—An alternative method for preparing formula (Ie) (particularly where $R^4$ is a sulfur-containing moiety, such as alkylsulfinyl) is to treat the corresponding compound of formula (Ic) with hydroxylamine hydrochloride and a peptide coupling reagent, preferably benzotriazol-1-yloxy-tris(dimethylamino) phosphonium hexafluorophosphate, in the presence of a tertiary amine base such as N-methylmorpholine in DMF solvent. The resulting compound of formula (Ie) is isolated from the reaction mixture by standard isolation techniques, for example, by extraction and concentration.

Starting Materials—Formula (D) is prepared as described with reference to Reaction Schemes 2, 2A and 2B. Formula (F) is prepared as described with reference to Reaction Schemes 3 and 3A. O-Benzylhydroxylamine is commercially available, for example, as the hydrochloride salt from Aldrich Co.

Formula (Ib)—A compound of formula (F) is cooled with a compound of formula (D) under standard amide coupling conditions to form a compound of formula (Ib). For example, to a solution of a compound of formula (F) in an aprotic solvent, preferably DMF, containing a slightly Alternative Preparation of Formula (Ib)—A particularly preferred method of preparing compounds of formula (Ib) when $R^2$ is an aryl or heteroaryl, and where X (not shown) is propanyl and p (not shown) is zero is shown in Reaction Scheme 4A.

Reaction Scheme 4A

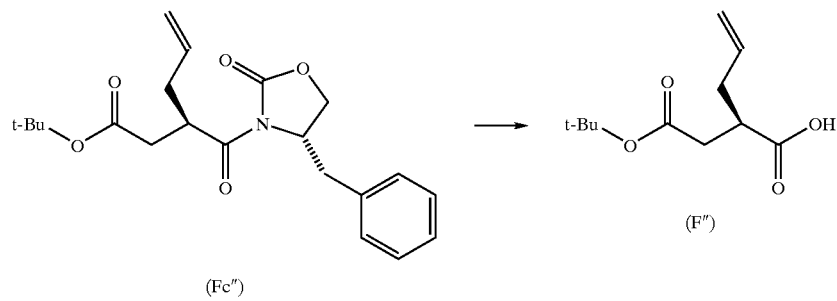

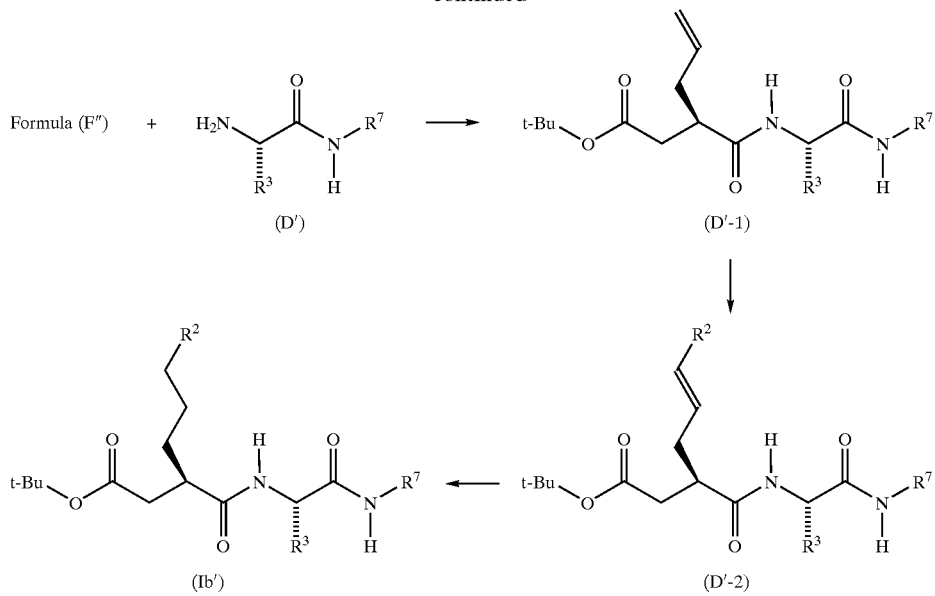

Starting Materials—The compound illustrated as formula (Fc″) can be prepared analogously to the preparation of formula (Fc′) as described with reference to Reaction Scheme 3A, by substituting for the compound of formula (Fa′) the corresponding allyl compound where $R^2$ is prop-2-enyl. The compound of formula (D′) is a compound of formula (D) and can be as described in Reaction Scheme 2. The halo-aryl or halo-heteroaryl reactants used in the preparation of compounds of formula (D′-2) are commercially available, or can be prepared according to methods known to those of ordinary skill in the art, e.g., as described in Example 41C.

A compound of formula (F″) is prepared by alkaline hydrolysis of the oxazolidinone group from a compound of formula (Fc″). After isolation by standard procedures, (F″) is coupled with a compound of formula (D′) under standard peptide coupling conditions as described above with reference to Reaction Scheme 2, to form a compound of formula (D′-1). Arylation or heteroarylation of (D′-1) is accomplished by adding aryl- or heteroaryl-halide (preferably aryl- or heteroaryl bromide, iodide or triflate) and heating the reaction mixture for about 2 hours at about 100° C. to form a compound of the formula (D′-2). Catalytic hydrogenation (Pd/C) of (D′-2) yields a compound of formula (Ib′).

Preparation of Formula (G)

Compounds of formula (G):

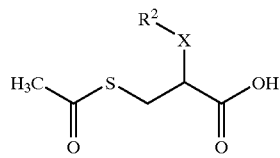

are intermediates in the preparation of compounds of formula (I) and are prepared as illustrated below in Reaction Scheme 6. The compounds of formula (G) are prepared as shown in Reaction Scheme 5.

Reaction Scheme 5

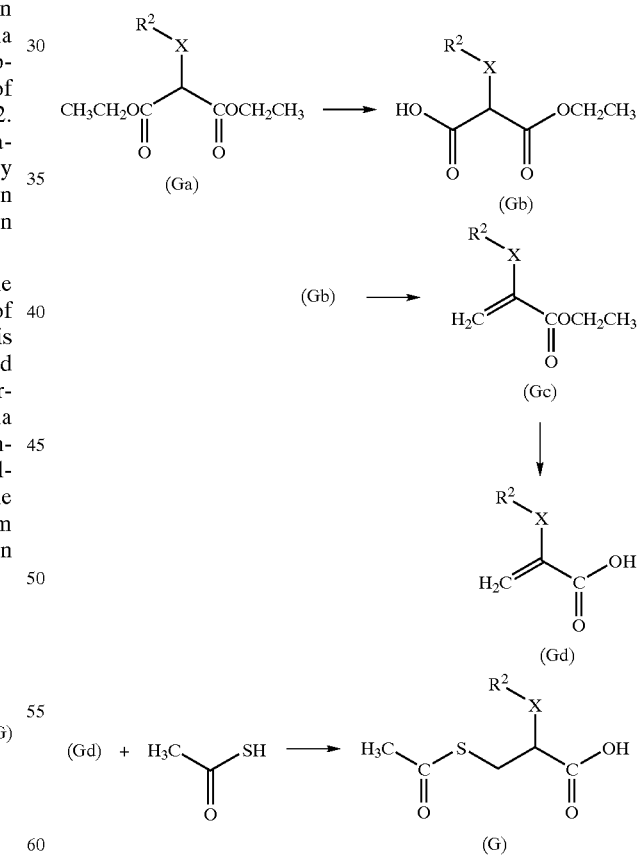

Starting Materials—Compounds of formula (Ga) and thioacetic acid are commercially available, for example, from TCI America Organic Chemicals and the Aldrich Company, respectively.

Formula (Gb)—A compound of formula (Ga) is hydrolyzed with an equimolar amount of a base, for example, potassium hydroxide, to yield a compound of formula (Gb).

Formula (Gc)—A compound of formula (Gb) is deprotonated under basic conditions, for example, in the presence of triethylamine, at 0–5° C. (preferably at 0° C.) and then reacted with formaldehyde, followed by treatment with aqueous base, preferably potassium carbonate, to yield a compound of formula (Gc), which is isolated from the reaction mixture by standard isolation procedures.

Formula (Gd)—A compound of formula (Gc) is hydrolyzed under basic conditions, preferably in the presence of lithium hydroxide, to yield a compound of formula (Gd).

Formula (G)—A compound of formula (Gd) is reacted with an excess molar amount of thioacetic acid at 90–100° C. (preferably at 95° C.) under an inert atmosphere. The compound of formula (G) is then isolated from the reaction mixture by standard isolation techniques, for example, by extraction and evaporation.

Preparation of Formulae (If) and (Ig)

The compounds of formulae (If) and (Ig) each represent sub-genuses of formula I in which the $R^1$ substituent is sulfur-containing, prepared sequentially as described in Reaction Scheme 6. In compounds of formula (If), $R^1$ is acetylthio. In compounds of formula (Ig), $R^1$ is mercapto.

Reaction Scheme 6

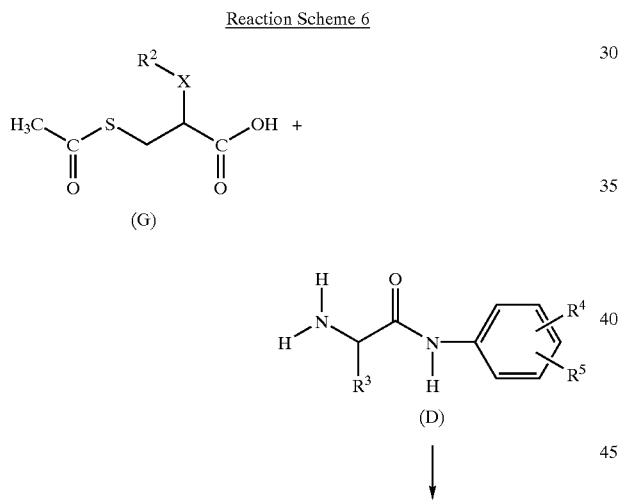

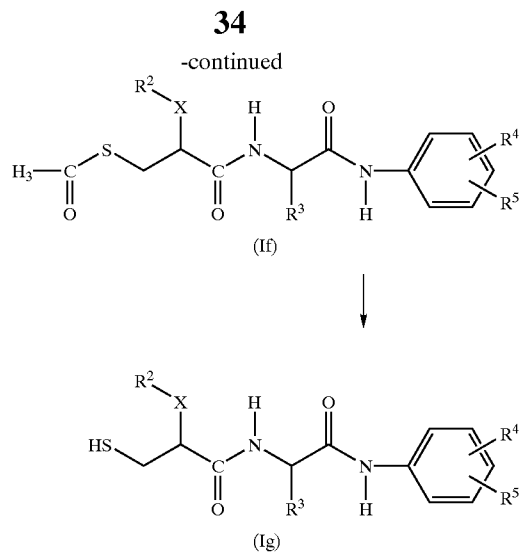

Formula (If)—A compound of formula (G) is coupled with a compound of formula (D) under standard amide coupling conditions to yield a compound of formula (If). For example, to a solution of the compound of formula (G) and HOBT in an aprotic solvent, preferably DMF, is added an excess molar amount of EDCI. Subsequently, the compound of formula (D) is added and the resulting mixture is stirred overnight at room temperature. The resulting compound of formula (If) is then isolated from the reaction mixture by standard isolation techniques, for example, by evaporation of solvent, extraction, and flash chromatography.

Formula (Ig)—A compound of formula (If) is hydrolyzed under basic conditions, preferably in a protic solvent such as methanol in the presence of ammonium hydroxide, to form a compound of formula (Ig).

Preparation of Formula (Ih)

Compounds of formula (Ih) are a sub-genus of formula (I) where $R^1$ is N-hydroxyformamide, and are prepared as shown in Reaction Scheme 7.

Reaction Scheme 7

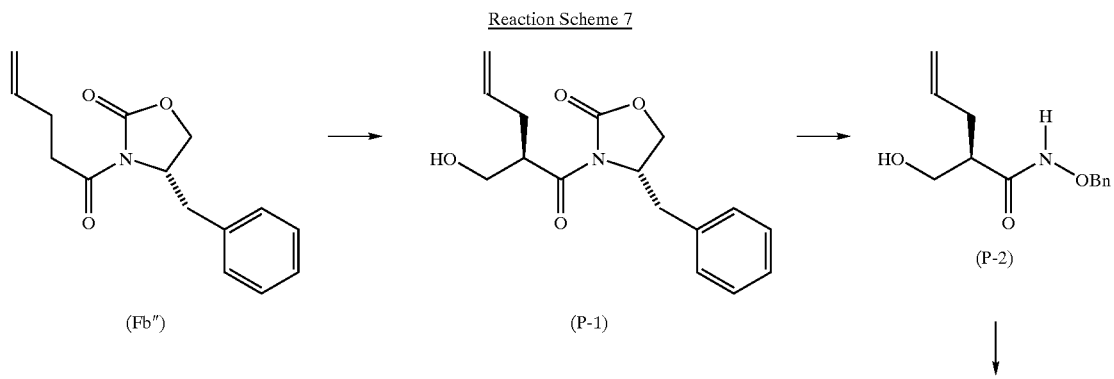

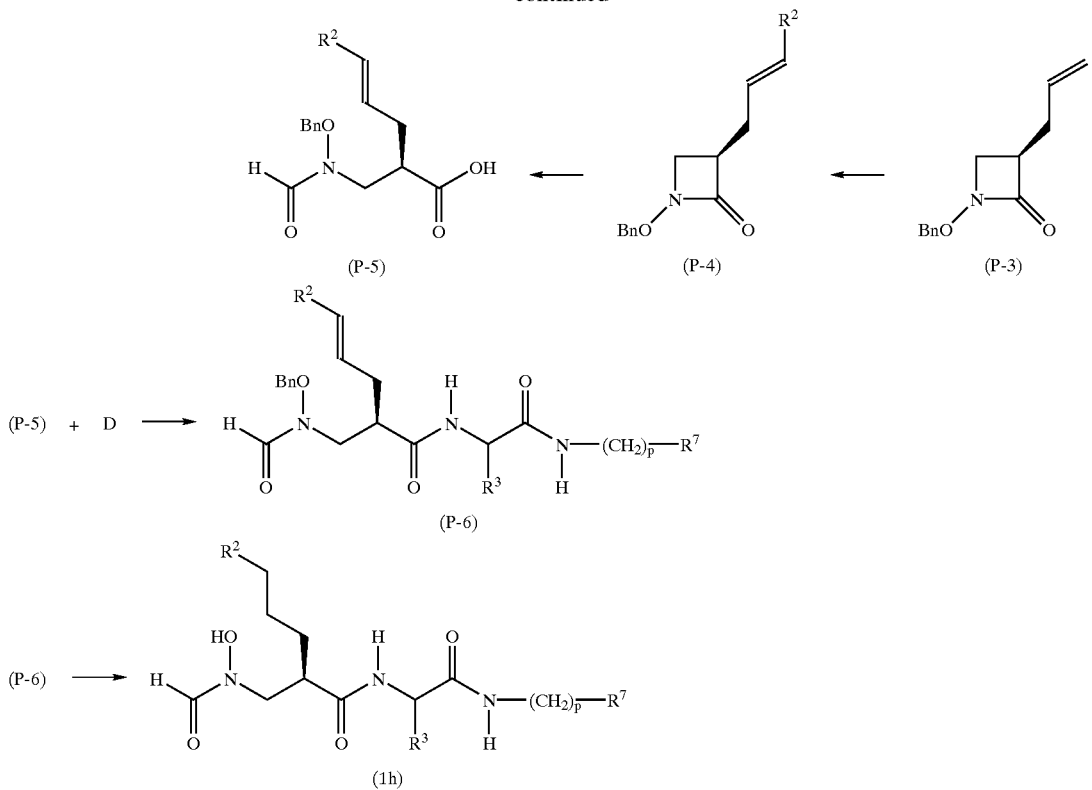

Starting Materials—The compound illustrated as formula (Fb") can be prepared analogously to the preparation of formula (Fb') as described with reference to Reaction Scheme 3A, by substituting for the compound of formula (Fa') the corresponding allyl compound where $R^2$ is prop-2-enyl.

Formula (P-1)—The compound of formula (Fb") is hydroxymethylated by incubation with titanium tetrachloride at reduced temperature, preferably 0° C., under basic conditions for one to three hours, preferably 1 hour followed by addition of S-trioxane and titanium tetrachloride with continued incubation at 0° C. for 3 to 5 hours, preferably 4 hours. The compound of formula (P-1) is then isolated by standard methods, e.g., extraction and column chromatography.

Formula (P-2)—The compound of formula (P-1) is reacted with an excess molar amount of 0-benzylhydroxylamine and of trimethylaluminum at reduced temperature, preferably 0° C. The reaction is allowed to proceed with stirring for 5 to 7 hours, preferably 6 hours, at 0° C. under argon. The resulting compound of formula (P-2) is isolated by standard procedures.

Formula (P-3)—Excess mesyl chloride is reacted with the compound of formula (P-2) in pyridine at 0° C. for several hours, preferably 3 hours. The reaction mixture is cooled on ice, organic solvent-extracted, and concentrated. The concentrated extract is refluxed under basic conditions for several hours, preferably 3 hours, thus yielding the azetidinone compound of formula (P-3), which is purified by standard procedures.

Formula (P-4)—The compound of formula (P-3) is reacted with a desired halogenated $R^2$ group (e.g., an aryl- or heteroaryl halide, preferably -bromide or iodide) in an inert solvent in the presence of a base, such as triethylamine, and a palladium catalyst, preferably formed from palladium (II) acetate and about 2 molar equivalents of tri-o-tolylphosphine. After heating the reaction mixture for 15 to 20 hours, preferably 18 hours at 100° C., the corresponding compound of formula (P-4) is isolated and purified by standard procedures.

Formula (P-5)—Cleavage of the azetidinone ring of a compound of formula (P-4) is carried out under basic conditions at room temperature for 1 to 3 hours, preferably 1 hour. The resultant compound is extracted into organic solvent, concentrated, redissolved in a base-containing solvent (e.g., pyridine), and carboxylated with formic anhydride at reduced temperature, preferably 0° C., for 30 minutes, to yield the corresponding compound of formula (P-5), which is isolated by standard procedures.

Formula (P-6)—A compound of formula (P-5) is coupled with a compound of formula (D') under standard amide coupling conditions to form the corresponding compound of formula (P-6), which is isolated by standard procedures.

Formula (Ih)—Catalytic hydrogenation of a compound of formula (P-6) with Pd/C, followed by removal of the catalyst by filtration yields the corresponding compound of formula (Ih).

Preparation of Salts

In addition, all compounds of formula (I) that exist in either the free acid or the free base form may be converted to their pharmaceutically acceptable salts by treatment with the appropriate inorganic or organic base or with the appropriate inorganic or organic acid, respectively. Salts of the compounds of formula (I) can also be converted to the free acid or free base form or to another salt. For example, a compound of formula (I) having a carboxylic acid moiety can be converted to the carboxylate form by addition of 1 equivalent of NaOH or KOH in an alcoholic solvent followed by evaporation of solvent. A compound of formula (I) in the form of a free base can be converted to the chloride salt, for example, by addition of 1 equivalent of HCl in an organic solvent, followed by concentration.

Preferred Synthesis and Last Steps

In summary, compounds of formula (I) are prepared by:

(A) contacting a compound of formula (D)

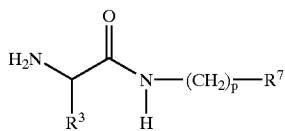

(D)

with a compound of formula (F)

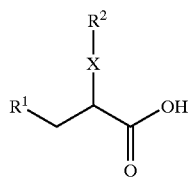

(F)

where $R^1$ is alkoxycarbonyl, aralkoxycarbonyl, aryl- or heteroaryl-thiomethylphosphinoyl, or acetylthio;
in the presence of a base and an amide coupling reagent to give the corresponding compound of formula (I); or (B) catalytically hydrogenating the corresponding compound where X and $R^2$ together are optionally aryl- or heteroaryl-substituted alkenyl; or (C) treating a compound of formula (I), where $R^1$ is alkoxycarbonyl or aralkoxycarbonyl, under mild acidic conditions to give the corresponding compound of formula (I) where $R^1$ is carboxy; or (D) contacting a compound of formula (I), where $R^1$ is carboxy, with O-benzylhydroxylamine to give the corresponding compound of formula (I) where $R^1$ is benzyloxycarbamoyl; or (E) catalytically hydrogenating a compound of formula (I), where $R^1$ is benzyloxycarbamoyl, to give the corresponding compound of formula (I) where $R^1$ is hydroxycarbamoyl; or (F) contacting a compound of formula (I), where $R^1$ is carboxy, with hydroxylamine to give the corresponding compound of formula (I) where $R^1$ is hydroxycarbamoyl; or (G) catalytically hydrogenating a compound of the formula

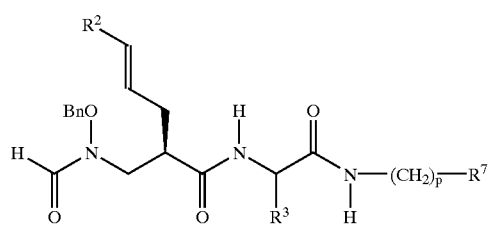

where BnO is benzyloxy, to give the corresponding compound of formula (I) where $R^1$ is N-hydroxyformamide; or (H) treating a compound of formula (I), wherein $R^1$ is acetylthio, with ammonium hydroxide in a protic solvent to give the corresponding compound of formula (I) where $R^1$ is mercapto.

A preferred method of making compounds of formula (I) where $R^1$ is N-hydroxyformamide entails converting a compound of formula (P-4)

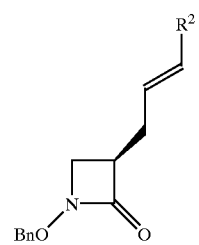

(P-4)

wherein $R^2$ is aryl or heteroaryl, by basic hydrolysis followed by formylation to give a compound of formula (P-5)

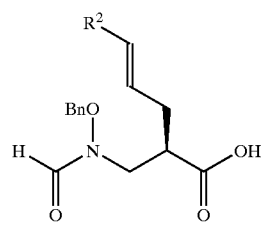

(P-5)

reacting the compound of formula (P-5) with a compound of formula (D) to give a compound of formula (P-6)

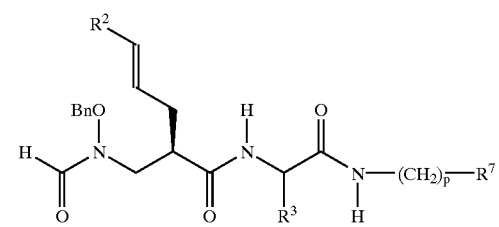

(P-6)

and catalytically hydrogenating the compound of formula (P-6).

Compounds prepared by the above-described process of the invention may be identified by the presence of a detectable amount of one or more compounds of formulae (P-3), (P-4) or (P-6). While it is well known that pharmaceuticals must meet pharmacopoeia standards before approval and/or marketing, and that synthetic reagents (such as O-benzylhydroxylamine) or precursors [such as (P-3), (P-4), or (P-6)] should not exceed the limits prescribed by pharmacopoeia standards, final compounds prepared by a process of the present invention may have minor, but detectable, amounts of such materials present, for example at levels in the range of 50 ppm or lower. These levels of (P-3) can be detected, e.g., by GC-MS, or of (P-4) can be detected, e.g., by HPLC-MS or by HPLC with fluorescence detection, or of (P-6) can be detected, e.g., by HPLC with fluorescence detection. It is important to monitor the purity of pharmaceutical compounds for the presence of such materials, which presence is additionally disclosed as a method of detecting use of a process of the invention.

EXAMPLES

The following preparations and examples are given to enable those skilled in the art to more clearly understand and to practice the present invention. They should not be considered as limiting the scope of the invention, but merely as being illustrative and representative thereof.

Example 1

Compounds of Formula (Ea)

1A. Crystalline phosphinic acid (8.4 g, 0.13 mol) was stirred in neat triethylorthoformate (22 mL, 0.20 mL) for 90 minutes at room temperature. This was then transferred via cannula to a stirred solution of ethylisobutylacrylate (8 g, 0.036 mol) and tetramethylguanidine (4.5 mL, 0.036 mol) that had been cooled to 0° C. for 10 minutes. The ice bath was removed and the reaction stirred for 4 hours. The mixture was diluted with 200 mL of diethyl ether and the solution washed with 1 N HCl (100 mL), water (4×100 mL) brine (100 mL); and dried over magnesium sulfate. This was rotary-evaporated to yield 8.15 g of 2-(ethoxy) phosphinoylmethyl-4-methylpentanoic acid ethyl ester as a slightly yellow colored oil, MS: 349 (M−H$_2$O)$^+$.

1B. In a similar manner, the following compounds of formula (Ea) are prepared:
  2-(ethoxy)phosphinoylmethyl-5-phenylpentanoic acid ethyl ester;
  2-(ethoxy)phosphinoylmethyl-4-phenylbutanoic acid ethyl ester;
  2-(ethoxy)phosphinoylmethyl-3-phenylpropanoic acid ethyl ester;
  2-(ethoxy)phosphinoylmethyl-3-cyclohexylpropanoic acid ethyl ester; and
  2-((ethoxy)phosphinoylmethyl)pentanoic acid ethyl ester.

Example 2

Compound of Formula (Eb)

2A. Crude 2-(ethoxy)phosphinoylmethyl-4-methylpentanoic acid ethyl ester (26 g) was dissolved in 600 mL THF/CH$_2$Cl$_2$ (50/50) and cooled to 0° C. Diisopropyl-ethylamine (32 mL) and 90.8 mL of bis-(trimethylsilyl) acetamide were then added to the solution and the resulting mixture was stirred for 20 minutes before paraformaldehyde (5.5 g) was added. The solution was brought to room temperature and heated at 37° C. for 18 hours. The solvent was removed by evaporation, and the resulting oil dissolved in 200 mL ethyl acetate. The solution was washed with 50 mL of 1N HCl (2×), 50 mL of brine (2×), dried over MgSO$_4$, filtered and evaporated to yield 19.3 g of 2-(ethoxy)(hydroxymethyl) phosphinoylmethyl-4-methylpentanoic acid ethyl ester as a faintly yellow oil, MS: 281.2 (MH$^+$).

2B. In a similar manner, the following compounds of formula (Eb) are prepared:
  2-(ethoxy)(hydroxymethyl)phosphinoylmethyl-5-phenylpentanoic acid ethyl ester;
  2-(ethoxy)(hydroxymethyl)phosphinoylmethyl-4-phenylbutanoic acid ethyl ester;
  2-(ethoxy)(hydroxymethyl)phosphinoylmethyl-3-phenylpropanoic acid ethyl ester;
  2-(ethoxy)(hydroxymethyl)phosphinoylmethyl-3-cyclohexylpropanoic acid ethyl ester; and
  2-((ethoxy)(hydroxymethyl)phosphinoylmethyl) pentanoic acid ethyl ester.

Example 3

Compounds of Formula (Ec)

3A. 2-(Ethoxy)(hydroxymethyl)phosphinoylmethyl-4-methylpentanoic acid ethyl ester (5 g) was dissolved in 20 mL of CH$_2$Cl$_2$ and cooled to −20° C. (in duplicate). Methanesulfonyl chloride (1.5 mL) and triethylamine (3.0 mL) were added to solution dropwise. After 15 minutes the bath was removed and the reaction left at room temperature for 3% hours. Each solution was then washed with 10 mL cold 2% HCl, 10 mL NaHCO$_3$ (sat), mL brine, dried with MgSO$_4$, filtered and evaporated to yield 12.8 g (combined yield) of 2-(ethoxy)(methane-sulfonyloxymethyl)phosphinoylmethyl-4-methylpentanoic acid ethyl ester.

3B. In a similar manner, but replacing methanesulfonyl chloride with p-toluenesulfonyl chloride, 2-(ethoxy)-(p-toluenesulfonyloxymethyl)phosphinoylmethyl-4-methylpentanoic acid ethyl ester is prepared.

3C. In a similar manner, the following compounds of formula (Ec) are prepared:
  2-(ethoxy)(methanesulfonyloxymethyl)phosphinoyl-methyl-5phenylpentanoic acid ethyl ester;
  2-(ethoxy)(methanesulfonyloxymethyl)phosphinoyl-methyl-4-phenylbutanoic acid ethyl ester;
  2-(ethoxy)(methanesulfonyloxymethyl)phosphinoyl-methyl-3-phenylpropanoic acid ethyl ester;
  2-(ethoxy)(methanesulfonyloxymethyl)phosphinoyl-methyl-3-cyclohexylpropanoic acid ethyl ester;
  2-((ethoxy)(methanesulfonyloxymethyl)phosphinoyl-methyl)pentanoic acid ethyl ester;
  2-(ethoxy)(p-toluenesulfonyloxymethyl)phosphinoyl-methyl-5-phenylpentanoic acid ethyl ester;
  2-(ethoxy)(p-toluenesulfonyloxymethyl)phosphinoyl-methyl-4-phenylbutanoic acid ethyl ester;
  2-(ethoxy)(p-toluenesulfonyloxymethyl)phosphinoyl-methyl-3-phenylpropanoic acid ethyl ester;
  2-(ethoxy)(p-toluenesulfonyloxymethyl)phosphinoyl-methyl-3-cyclohexylpropanoic acid ethyl ester; and
  2-((ethoxy)(p-toluenesulfonyloxymethyl)phosphinoyl-methyl)pentanoic acid ethyl ester.

Example 4

Compounds of Formula (Ee)

4A. Sodium hydride (1.52 g, (60%)) and 2-quinolinethiol (6 g) were stirred together at 0° C. in 50 mL DMF. After the initial H₂ evolution had subsided, the mixture was stirred at room temperature for 2.5 hours. The mixture was then cooled to 0° C. and 2-(ethoxy)(methanesulfonyloxymethyl)phosphinoylmethyl-4-methylpentanoic acid ethyl ester (12.8 g) in 10 mL DMF was added via cannula and the resulting mixture was then stirred for 18 hours, slowly warming to room temperature. The DMF was removed by evaporation, the residue dissolved in 50 mL ethyl acetate and washed with 50 mL H₂O (2×), brine (50 mL), dried with MgSO₄ and evaporated to a yellow semi-solid. Purification by flash chromatography using 10 ethyl acetate/hexane to 80% ethyl acetate/hexane for the elution yielded 10 g of 2-(ethoxy)(quinolin-2-ylthiomethyl)-phosphinoyl-methyl-4-methylpentanoic acid ethyl ester (Rf 0.35 80% ethyl acetate/hexane), MS: 424.1 (MH⁺).

4B. In a similar manner, but replacing 2-quinolinethiol with 1-naphthalenethiol, 2-naphthalenethiol or thiophenol, the following compounds of formula (Ee) are prepared:

2-(ethoxy)(naphth-1-ylthiomethyl)phosphinoylmethyl-4-methylpentanoic acid ethyl ester;

2-(ethoxy)(naphth-2-ylthiomethyl)phosphinoylmethyl-4-methylpentanoic acid ethyl ester; and 2-(ethoxy)(phenylthiomethyl)phosphinoylmethyl-4-methylpentanoic acid ethyl ester.

4C. In a similar manner, the following compounds of formula (Ee) are prepared:

2-(ethoxy)(quinolin-2-ylthiomethyl)phosphinoylmethyl-5-phenylpentanoic acid ethyl ester;

2-(ethoxy)(quinolin-2-ylthiomethyl)phosphinoylmethyl-4-phenylbutanoic acid ethyl ester;

2-(ethoxy)(quinolin-2-ylthiomethyl)phosphinoylmethyl-3-phenylpropanoic acid ethyl ester;

2-(ethoxy)(quinolin-2-ylthiomethyl)phosphinoylmethyl-3-cyclohexylpropanoic acid ethyl ester;

2-((ethoxy)(quinolin-2-ylthiomethyl)phosphinoylmethyl)pentanoic acid ethyl ester;

2-(ethoxy)(naphth-1-ylthiomethyl)phosphinoylmethyl-5-phenylpentanoic acid ethyl ester;

2-(ethoxy)(naphth-1-ylthiomethyl)phosphinoylmethyl-4-phenylbutanoic acid ethyl ester;

2-(ethoxy)(naphth-1-ylthiomethyl)phosphinoylmethyl-3-phenylpropanoic acid ethyl ester;

2-(ethoxy)(naphth-1-ylthiomethyl)phosphinoylmethyl-3-cyclohexylpropanoic acid ethyl ester;

2-((ethoxy)(naphth-1-ylthiomethyl)phosphinoylmethyl)pentanoic acid ethyl ester;

2-(ethoxy)(naphth-2-ylthiomethyl)phosphinoylmethyl-5-phenylpentanoic acid ethyl ester;

2-(ethoxy)(naphth-2-ylthiomethyl)phosphinoylmethyl-4-phenylbutanoic acid ethyl ester;

2-(ethoxy)(naphth-2-ylthiomethyl)phosphinoylmethyl-3-phenylpropanoic acid ethyl ester;

2-(ethoxy)(naphth-2-ylthiomethyl)phosphinoylmethyl-3-cyclohexylpropanoic acid ethyl ester;

2-((ethoxy)(naphth-2-ylthiomethyl)phosphinoylmethyl)pentanoic acid ethyl ester;

2-(ethoxy)(phenylthiomethyl)phosphinoylmethyl-5-phenylpentanoic acid ethyl ester;

2-(ethoxy)(phenylthiomethyl)phosphinoylmethyl-4-phenylbutanoic acid ethyl ester;

2-(ethoxy)(phenylthiomethyl)phosphinoylmethyl-3-phenylpropanoic acid ethyl ester;

2-(ethoxy)(phenylthiomethyl)phosphinoylmethyl-3-cyclohexylpropanoic acid ethyl ester; and 2-((ethoxy)(phenylthiomethyl)phosphinoylmethyl)pentanoic acid ethyl ester.

Example 5

Compounds of Formula (E)

5A. 2-(Ethoxy)(quinolin-2-ylthiomethyl)phosphinoylmethyl-4-methylpentanoic acid ethyl ester (4.5 g) was dissolved in 100 mL THF and 12.5 mL of 2N NaOH was added together with enough methanol to make the solution homogeneous. After 18 hours the THF was removed by evaporation, the residue diluted with 50 mL H₂O and washed with 50 mL ethyl acetate. The aqueous phase was then acidified to pH 4, and the product extracted with 50 mL ethyl acetate (2×). The ethyl acetate was washed with 20 mL brine, dried with MgSO₄ and evaporated to yield 3.8 g of 2-(hydroxy)(quinolin-2-ylthiomethyl)phosphinoylmethyl-4-methylpentanoic acid as a yellow oil, MS: 368 (MH⁺).

5B. In a similar manner, the following compounds of formula (E) are prepared:

2-(hydroxy)(naphth-1-ylthiomethyl)phosphinoylmethyl-4-methylpentanoic acid;

2-(hydroxy)(naphth-2-ylthiomethyl)phosphinoylmethyl-4-methylpentanoic acid; and 2-(hydroxy)(phenylthiomethyl)phosphinoylmethyl-4-methylpentanoic acid.

5C. In a similar manner, the following compounds of formula (E) are prepared:

2-(hydroxy)(quinolin-2-ylthiomethyl)phosphinoylmethyl-5-phenylpentanoic acid;

2-(hydroxy)(quinolin-2-ylthiomethyl)phosphinoylmethyl-4-phenylbutanoic acid;

2-(hydroxy)(quinolin-2-ylthiomethyl)phosphinoylmethyl-3-phenylpropanoic acid;

2-(hydroxy)(quinolin-2-ylthiomethyl)phosphinoylmethyl-3-cyclohexylpropanoic acid;

2-((hydroxy)(quinolin-2-ylthiomethyl)phosphinoylmethyl)pentanoic acid;

2-(hydroxy)(naphth-1-ylthiomethyl)phosphinoylmethyl-5-phenylpentanoic acid;

2-(hydroxy)(naphth-1-ylthiomethyl)phosphinoylmethyl-4-phenylbutanoic acid;.

2-(hydroxy)(naphth-1-ylthiomethyl)phosphinoylmethyl-3-phenylpropanoic acid;

2-(hydroxy)(naphth-1-ylthiomethyl)phosphinoylmethyl-3-cyclohexylpropanoic acid;

2-((hydroxy)(naphth-1-ylthiomethyl)phosphinoylmethyl)pentanoic acid;

2-(hydroxy)(naphth-2-ylthiomethyl)phosphinoylmethyl-5-phenylpentanoic acid;

2-(hydroxy)(naphth-2-ylthiomethyl)phosphinoylmethyl-4-phenylbutanoic acid;

2-(hydroxy)(naphth-2-ylthiomethyl)phosphinoylmethyl-3-phenylpropanoic acid;

2-(hydroxy)(naphth-2-ylthiomethyl)phosphinoylmethyl-3-cyclohexylpropanoic acid;

2-((hydroxy)(naphth-2-ylthiomethyl)phosphinoylmethyl)pentanoic acid;

2-(hydroxy)(phenylthiomethyl)phosphinoylmethyl-5-phenylpentanoic acid;

2-(hydroxy)(phenylthiomethyl)phosphinoylmethyl-4-phenylbutanoic acid;

2-(hydroxy)(phenylthiomethyl)phosphinoylmethyl-3-phenylpropanoic acid;

2-(hydroxy)(phenylthiomethyl)phosphinoylmethyl-3-cyclohexylpropanoic acid; and 2-((hydroxy)(phenylthiomethyl)phosphinoylmethyl)pentanoic acid.

Example 6

Resolution of a Compound of Formula (E)

2-(Hydroxy)(quinolin-2-ylthiomethyl)phosphinoylmethyl-4-methylpentanoic acid (5.3 g) was dissolved in 50 mL of warm ethanol (abs) and 4.2 g of (−)-cinchonidine was added. After 30 minutes at room temperature the salt began to precipitate out. The flask was covered in foil and allowed to stand for 2 days. The salt was then removed by suction filtration, and the filtrate evaporated to a yellow foam. The salt and the filtrate were each dissolved in 100 mL ethyl acetate and washed successively with 1% HCl to remove the cinchonidine while keeping the pH above 4. Both solutions were each dried over $MgSO_4$ and evaporated to yield 2.4 g of a single stereoisomer, $[\alpha]_D^{24}$=+10.68° (9.73 mg in methanol (2 mL)) and 2.5 g of the other single stereoisomer, $[\alpha]_D^{24}$=−8.70° (9.88 mg in methanol (2 mL)).

Example 7

Compounds of Formula (B)

7A. To a cold (0° C.) suspension of 4-acetamido-benzenesulphonyl chloride (4.0 g, 17 mmol) in $CH_2Cl_2$ (40 mL) was added pyridine (1.7 mL, 20 mmol) and DMAP (209 mg, 1.7 mmol). (A clear solution resulted). Anhydrous methylamine was bubbled into the solution for 1 hour at 0° C., and then the solution was allowed to stir at 25° C. for 2 hours. The solution was extracted with 1M NaOH (3×15 mL) and the combined extracts were adjusted to pH 6 at 0° C. with 3M HCl. The product, which precipitated as fluffy white crystals, was filtered and washed with cold water to afford 3.2 g (82%) of 4-acetamido-N-methylbenzenesulphonamide: $^1$H NMR (300 MHz, MeOH) δ 2.35 (s, 3H), 2.70 (s, 3H), 7.96 (s, 4H).

7B. A mixture of 4-acetamido-N-methylbenzenesulphonamide (3.2 g, 14 mmol) and 100 mL of 1M HCl was refluxed under argon for 3 hours. After cooling to 25° C., $CH_2Cl_2$ (10 mL) was added and the aqueous phase was neutralized with 1M NaOH at 0° C. The aqueous phase was separated and extracted with $CH_2Cl_2$ (2×25 mL). The combined organic phases were washed with brine (10 mL), dried ($Na_2SO_4$) and concentrated to afford 1.5 g (58%) of a compound of formula (B) where $R^4$ is N-methylsulfonamide as a colorless solid: $^1$H NMR (300 MHz, MeOH) δ 2.46 (s, 3H), 6.67–6.72 ($AA^1$ part of $AA^1XX^1$ 2H), 7.48–7.52 ($XX^1$ part of $AA^1XX^1$, 2H).

Example 8

Compounds of Formula (C)

8A. To a cold (0° C.) solution of N-tert-butoxycarbonyl-L-leucine (1.4 g, 6.3 mmol) and HOBT (1.5 g, 9.8 mmol) in DMF (30 mL) was added EDCI (2.5 g, 14 mmol) in portions. After stirring for 1 hour at 0° C., the resulting solution was treated with methyl 4-aminobenzoate (1.09 mL, 6.8 mmol) and DMAP (0.32 g, 2.6 mmol). After stirring for 24 hours at 25° C., the DMF was removed in vacuo. The residue was dissolved in $CH_2Cl_2$ and washed with saturated $NAHCO_3$ solution, 1M HCl (twice), and brine. Drying over $Na_2SO_4$ and concentration in vacuo afforded the crude product which was purified by flash chromatography on $SiO_2$ (20% ethyl acetate/hexenes eluent). There was obtained 1.0 g (85%) of N-t-butoxycarbonyl-L-leucine-N'-(4-methoxycarbonylphenyl)carboxamide as a foamy solid, MS (FAB) 363 (M−H)⁻.

8B. In a similar manner, the following compound of formula (C) were prepared:

N-t-butoxycarbonyl-L-tryptophan-N'-phenylmethylcarboxamide;

N-t-butoxycarbonyl-L-tryptophan-N'-phenylcarboxamide;

N-t-butoxycarbonyl-L-tryptophan-N'-(4-methoxycarbonylphenyl)carboxamide;

N-t-butoxycarbonyl-L-tryptophan-N'-(4-ethoxycarbonylphenyl)carboxamide;

N-t-butoxycarbonyl-L-leucine-N'-(4-(N"-methylaminosulfonyl)phenyl)carboxamide;

N-t-butoxycarbonyl-L-alanine-N'-(4-methoxycarbonylphenyl)carboxamide;

N-t-butoxycarbonyl-L-methionine-N'-(4-methoxycarbonylphenyl)carboxamide;

N-t-butoxycarbonyl-L-leucine-N'-(3-ethoxycarbonylphenyl)carboxamide;

N-t-butoxycarbonyl-L-leucine-N'-(2-methoxycarbonylphenyl)carboxamide;

N-t-butoxycarbonyl-L-leucine-N'-(4-(1-methylethyloxy)carbonyl)phenyl)carboxamide;

N-t-butoxycarbonyl-L-leucine-N'-(aminosulfonyl)phenyl)carboxamide;

N-t-butoxycarbonyl-L-leucine-N'-(4-methoxycarbonylmethylphenyl)carboxamide;

N-t-butoxycarbonyl-L-pyridin-3-ylalanine-N'-(4-methoxycarbonylphenyl)carboxamide;

N-t-butoxycarbonyl-L-cyclohexylglycine-N'-(4-methoxycarbonylphenyl)carboxamide;

N-t-butoxycarbonyl-L-isoleucine-N'-(4-methoxycarbonylphenyl)carboxamide

N-t-butoxycarbonyl-L-O-benzylthreonine-N'-(4-methoxycarbonylphenyl)carboxamide;

N-t-butoxycarbonyl-L-t-leucine-N'-(4-methoxycarbonylphenyl)carboxamide;

N-t-butoxycarbonyl-L-leucine-N'-(4-cyanophenyl)carboxamide;

N-t-butoxycarbonyl-L-leucine-N'-(4-(N"-(2-dimethylaminoethylcarbamoyl)carboxamide; and 1N-t-butoxycarbonyl-L-leucine-N'-(4-(N"-(3-dimethylaminopropyl)carbamoyl)phenyl)carboxamide.

8C. In a similar manner, the following compounds of formula (C) are prepared:

N-t-butoxycarbonyl-L-tryptophan-N'-(4-nitrophenyl)carboxamide;

N-t-butoxycarbonyl-L-tryptophan-N'-(4-aminophenyl)carboxamide;

N-t-butoxycarbonyl-L-leucine-N'-(4-methylsulfonylphenyl)carboxamide;

N-t-butoxycarbonyl-L-leucine-N'-(4-ethyloulfonylphenyl)carboxamide; and

N-t-butoxycarbonyl-L-leucine-N'-(4-tetrazolylphenyl)carboxamide.

Example 9

Compounds of Formula (D)

9A. To a cold (0° C.) solution of N-t-butoxycarbonyl-L-leucine-N'-phenylcarboxamide (3.4 g, 11 mmol) in dry $CH_2Cl_2$ (10 mL) was added TFA (2 mL). The solution was allowed to stir at 25° C. for 6 hours and was then concentrated in vacuo. The residue was partitioned between $CH_2Cl_2$ and $H_2O$ and the aqueous layer was basified at 0° C. with saturated $K_2CO_3$ solution. The organic phase was separated and the aqueous layer was extracted three times with $CH_2Cl_2$. The combined organic layers were washed with brine and dried over $Na_2SO_4$. Concentration afforded L-leucine-N'-phenylcarboxamide.

9B. In a similar manner, the following compounds are prepared:
L-leucine-N'-(4-methoxycarbonylphenyl)carboxamide;
L-tryptophan-N'-phenylmethylcarboxamide;
L-tryptophan-N'-phenylcarboxamide;
L-tryptophan-N'-(4-methoxycarbonylphenyl)carboxamide;
L-tryptophan-N'-(4-ethoxycarbonylphenyl)carboxamide;
L-leucine-N'-(4-(N"-methylaminosulfonyl)phenyl)carboxamide;
L-alanine-N'-(4-methoxycarbonylphenyl)carboxamide;
L-methionine-N'-(4-methoxycarbonylphenyl)carboxamide;
L-leucine-N'-(3-ethoxycarbonylphenyl)carboxamide;
L-leucine-N'-(2-methoxycarbonylphenyl)carboxamide;
L-leucine-N'-(4-(1-methylethyloxy)carbonyl)phenyl)carboxamide;
L-leucine-N'-(aminosulfonyl)phenyl)carboxamide;
L-leucine-N'-(4-methoxycarbonylmethylphenyl)carboxamide;
L-pyridin-3-ylalanine-N'-(4-methoxycarbonylphenyl)carboxamide;
L-spirocyclopentylglycine-N'-(4-methoxycarbonylphenyl)carboxamide;
L-cyclohexylglycine-N'-(4-methoxycarbonylphenyl)carboxamide;
L-isoleucine-N'-(4-methoxycarbonylphenyl)carboxamide;
L-O-benzylthreonine-N'-(4-methoxycarbonylphenyl)carboxamide;
L-t-leucine-N'-(4-methoxycarbonylphenyl)carboxamide;
L-leucine-N'-(4-cyanophenyl)carboxamide;
L-leucine-N'-(4-(N"-(2-dimethylaminoethyl)carbamoyl)phenyl)carboxamide; and
L-leucine-N'-(4-(N"-(3-dimethylaminopropyl)carbamoyl)phenyl)carboxamide.

9C. In a similar manner, the following compounds of formula (D) are prepared:
L-tryptophan-N'-(4-nitrophenyl)carboxamide;
L-tryptophan-N'-(4-aminophenyl)carboxamide;
L-leucine-N'-(4-methylsulfonylphenyl)carboxamide;
L-leucine-N'-(4-ethylsulfonylphenyl)carboxamide; and
L-leucine-N'-(4-tetrazolylphenyl)carboxamide.

Example 10

Compounds of Formula (Ia)

10A. To a cold (0° C.) solution of 2-(hydroxy)(quinolin-2-ylthiomethyl)phosphinoylmethyl-4-methylpentanoic acid (0.20 g, 0.54 mmol) in THF (6 mL) was added 1,1'-carbonyldiimidazole (0.12 g, 0.7 mmol). The mixture was stirred for 75 minutes at 0° C. and was then treated with L-tryptophan-N'-(4-ethoxycarbonylphenyl)carboxamide (0.22 g, 0.62 mmol) and stirred at 25° C. for 15 hours. The THF was evaporated and the residue was dissolved in ethyl acetate (60 mL). The solution was washed with $H_2O$ (10 mL), brine (10 mL), and dried over $MgSO_4$. Concentration was followed by reverse phase HPLC using a gradient of acetonitrile and 50 mM $NH_4OAc$ buffer afforded 30 mg of N-(2-(hydroxy)(quinolin-2-ylthiomethyl)phosphinoyl-methyl-4-methylpentanoyl)-L-tryptophan-N'-(4-ethoxycarbonyl-phenyl)carboxamide as an off white solid, MS (FAB) 701 (M–H)$^+$ (mixture of diastereomers).

10B. In a similar manner, the following compounds of formula (Ia) were prepared:
N-(2-(hydroxy)(quinolin-2-ylthiomethyl)phosphinoylmethyl-4-methylpentanoyl)-L-tryptophan-N'-(4-methoxycarbonylphenyl)carboxamide, MS (FAB) 687 (M+H)$^+$;
N-(2-(hydroxy)(quinolin-2-ylthiomethyl)phosphinoylmethyl-4-methylpentanoyl)-L-alanine-N'-(4-methoxycarbonylphenyl)carboxamide, MS (FAB) 572 (M+H)$^+$;
N-(2-(hydroxy)(quinolin-2-ylthiomethyl)phosphinoylmethyl-4-methylpentanoyl)-L-methionine-N'-(4-methoxycarbonylphenyl)carboxamide, MS (FAB) 632 (M+H)$^+$;
N-(2-(hydroxy)(quinolin-2-ylthiomethyl)phosphinoylmethyl-4-methylpentanoyl)-L-leucine-N'-(4-methoxycarbonylphenyl)carboxamide, MS (FAB) 614 (M+H)$^+$;
N-(2-(hydroxy)(quinolin-2-ylthiomethyl)phosphinoylmethyl-4-methylpentanoyl)-L-leucine-N'-(3-ethoxycarbonylphenyl)carboxamide, $^1$H NMR (300 MHz, MeOH) δ 0.73–1.01 (m, 12H), 1.28–2.00 (m, 14H), 2.4–3.61 (m, 2H), 4.27–4.45 (m, 3H), 7.23–7.44 (m, 3H), 7.65–7.98 (m, 6H), 8.29 (s, 0.5H), 8.50 (s, 0.5H);
N-(2-(hydroxy)(quinolin-2-ylthiomethyl)phosphinoylmethyl-4-methylpentanoyl)-L-leucine-N'-(2-methoxycarbonylphenyl)carboxamide, $^1$H NMR (300 MHz, MeOH) δ 0.78–0.99 (m, 13H), 1.3–2.4 (m, 7H), 2.90–3.05 (m, 1H), 3.5–3.75 (m, 2H), 3.89, 3.90, 3.94 (3s, 3H total), 4.35–3.50 (m, 1H), 7.05–8.10 (m, 11H), 8.32, 8.55, 8.60 (3d, J=8.7, 1H);
N-(2-(hydroxy)(quinolin-2-ylthiomethyl)phosphinoylmethyl-4-methylpentanoyl)-L-leucine-N'-(4-(1,1-dimethylethoxycarbonylphenyl)carboxamide, MS (FAB) 642 (MH)$^+$;
N-(2-(hydroxy)(quinolin-2-ylthiomethyl)phosphinoylmethyl-4-methylpentanoyl)-L-leucine-N'-(4-aminosulfonylphenyl)carboxamide, $^1$H NMR (300 MHz, MeOH) δ 0.76 (d, J=6.5, 3H), 0.81 (d, J=6.5, 3H), 0.85–1.1 (m, 7H), 1.2–2.1 (m, 7H), 2.92–2.95 (m, 1H), 3.45–3.70 (m, 2H), 4.35–4.45 (m, 1H), 7.28 (d, J=8.7, 1H), 7.45 (t, J=8.7, 1H), 7.68 (t, J=8.7, 1H), 7.7–7.8 (m, 3H), 7.87 (d, J=8.7, 1H), 7.95–8.1 (m, 3H);
N-(2-(hydroxy)(quinolin-2-ylthiomethyl)phosphinoylmethyl-4-methylpentanoyl)-L-leucine-N'-(4-methoxycarbonylmethylphenyl)carboxamide, MS (FAB) 628 (MH)$^+$.

10C. In a similar manner, the following compounds of formula (Ia) are prepared:
N-(2-(hydroxy)(quinolin-2-ylthiomethyl)phosphinoylmethyl-5-phenylpentanoyl)-L-leucine-N'-(4-methoxycarbonylphenyl)carboxamide;

N-(2-(hydroxy)(quinolin-2-ylthiomethyl)
phosphinoylmethyl-4-phenylbutanoyl)-L-leucine-N'-
(4-methoxycarbonylphenyl)carboxamide;

N-(2-(hydroxy)(quinolin-2-ylthiomethyl)
phosphinoylmethyl-3-phenylpropanoyl)-L-leucine-N'-
(4-methoxycarbonylphenyl)carboxamide;

N-(2-(hydroxy)(quinolin-2-ylthiomethyl)
phosphinoylmethyl-3-cyclohexylpropanoyl)-L-
leucine-N'-(4-methoxycarbonylphenyl)carboxamide;

N-(2-((hydroxy)(quinolin-2-ylthiomethyl)
phosphinoylmethyl)pentanoyl)-L-leucine-N'-(4-
methoxycarbonylphenyl)carboxamide;

N-(2-(hydroxy)(naphth-1-ylthiomethyl)phosphinoyl-
methyl-5-phenylpentanoyl)-L-leucine-N'-(4-
methoxycarbonylphenyl)carboxamide;

N-(2-(hydroxy)(naphth-1-ylthiomethyl)phosphinoyl-
methyl-4-phenylbutanoyl)-L-leucine-N'-(4-
methoxycarbonylphenyl)carboxamide;

N-(2-(hydroxy)(naphth-1-ylthiomethyl)phosphinoyl-
methyl-3-phenylpropanoyl)-L-leucine-N'-(4-
methoxycarbonylphenyl)carboxamide;

N-(2-(hydroxy)(naphth-1-ylthiomethyl)phosphinoyl-
methyl-3-cyclohexylpropanoyl)-L-leucine-N'-(4-
methoxycarbonylphenyl)carboxamide;

N-(2-((hydroxy)(naphth-1-ylthiomethyl)phosphinoyl-
methyl)pentanoyl)-L-leucine-N'-(4-
methoxycarbonylphenyl)carboxamide;

N-(2-(hydroxy)(naphth-2-ylthiomethyl)phosphinoyl-
methyl-5-phenylpentanoyl)-L-leucine-N'-(4-
methoxycarbonylphenyl)carboxamide;

N-(2-(hydroxy)(naphth-2-ylthiomethyl)phosphinoyl-
methyl-4-phenylbutanoyl)-L-leucine-N'-(4-
methoxycarbonylphenyl)carboxamide;

N-(2-(hydroxy)(naphth-2-ylthiomethyl)phosphinoyl-
methyl-3-phenylpropanoyl)-L-leucine-N'-(4-
methoxycarbonylphenyl)carboxamide;

N-(2-(hydroxy)(naphth-2-ylthiomethyl)phosphinoyl-
methyl-3-cyclohexylpropanoyl)-L-leucine-N'-(4-
methoxycarbonylphenyl)carboxamide;

N-(2-((hydroxy)(naphth-2-ylthiomethyl)phosphinoyl-
methyl)pentanoyl)-L-leucine-N'-(4-methoxycarbonyl-
phenyl)carboxamide;

N-(2-(hydroxy)(phenylthiomethyl)phosphinoylmethyl-5-
phenylpentanoyl)-L-leucine-N'-(4-methoxycarbonyl-
phenyl)carboxamide;

N-(2-(hydroxy)(phenylthiomethyl)phosphinoylmethyl-4-
phenylbutanoyl)-L-leucine-N'-(4-methoxycarbonyl-
phenyl)carboxamide;

N-(2-(hydroxy)(phenylthiomethyl)phosphinoylmethyl-3-
phenylpropanoyl)-L-leucine-N'-(4-methoxycarbonyl-
phenyl)carboxamide;

N-(2-(hydroxy)(phenylthiomethyl)phosphinoylmethyl-3-
cyclohexylpropanoyl)-L-leucine-N'-(4-methoxy-
carbonylphenyl)carboxamide; and N-(2-((hydroxy)(phenylthiomethyl)phosphinoylmethyl)
pentanoyl)-L-leucine-N'-(4-methoxycarbonylphenyl)
carboxamide.

10D. A solution of N-(2-(hydroxy)(quinolin-2-ylthiomethyl)
phosphinoylmethyl-4-methylpentanoyl)-L-tryptophan-
N'-(4-methoxycarbonylphenyl)carboxamide in THF (2
mL) and 1M NaOH (1 mL) was stirred for 24 hours at 25°
C. The organic solvents were evaporated, and the residue
dissolved in ethyl acetate/H$_2$O. The aqueous phase was
acidified with 1M HCl and the separated aqueous phase
was extracted twice with ethyl acetate. The combined
organic layers were washed with brine, dried (MgSO$_4$)
and concentrated to 27 mg of N-(2-(hydroxy)(quinolin-
2-ylthiomethyl)phosphinoylmethyl-4-methylpentanoyl)-
L-tryptophan-N'-(4-carboxyphenyl)carboxamide as a yel-
low powder.

10E. In a similar manner, but starting with N-(2-(hydroxy)
(quinolin-2-ylthiomethyl)phosphinoylmethyl-4-
methylpentanoyl)-L-leucine-N'-(4-methoxycarbonyl-
phenyl)carboxamide (30 mg, 0.048 mmol) there was
obtained 10 mg of N-(2-(hydroxy)(quinolin-2-
ylthiomethyl)phosphinoylmethyl-4-methylpentanoyl)-L-
leucine-N'-(4-carboxyphenyl)carboxamide as a semisolid
after trituration with ethyl acetate; $^1$H NMR$^1$ (300 MHZ,
MeOH) 0.81–1.02 (m, 12H), 1.1–2.3 (m, 10H), 2.82–3.00
(m, 1H), 3.49, 3.56 (2s, 2H), 3.5–3.8 (m, 2H), 4.45–4.55
(m, 1H), 7.09 (d, J=8.2, 1H), 7.19 (d, J=8.2, 1H), 7.45 (t,
J=8.2, 1H) 7.45–7.6 (m, 3H), 7.65–7.80 (m, 1H),
7.82–7.98 (m, 2H), 8.10–8.20 (m, 1H).

Example 11

Compounds of Formula (Fa)

11A. To 4-methylpentanoic acid (25 g, 0.215 mmol) in a 25°
C. water bath, thionyl chloride (20.4 mL, 1.3 g) was
slowly added. Then the mixture was heated at 50° C.
under argon for 3 hours (until the evolution of gas had
stopped). The crude reaction mixture was distilled at
atmospheric pressure to give 4-methylpentanoyl chloride
(25.3 g, 87.3%), b.p. 143° C.

11B. In a similar manner, but replacing 4-methylpentanoic
acid with 5-phenylpentanoic acid (5 g),
5-phenylpentanoyl chloride was prepared (4.4 g), as a
colorless liquid, b.p. 91°–93° C.

Example 12

Compounds of Formula (Fb)

12A. To a suspension of 60% NaH (836 mg, 1.5 eq.) in
toluene (200 mL) at room temperature under argon was
added L-(+)-2,10-camphor sultam (3.0 g, 13.9 mmol)
portion-wise. The mixture was stirred vigorously at room
temperature for one hour. Then 4-methylpentanoyl chlo-
ride was carefully added dropwise to the solution at 0° C.
After stirring the reaction at room temperature for 3 hours,
the reaction was quenched with 10 mL of water, and 70
mL of ether was added. The reaction mixture was first
washed with 0.5N HCl (2×50 mL), then 5% K$_2$CO$_3$ (3×50
mL) and finally with brine (1×50 mL). The organic layer
was dried over MgSO$_4$, filtered and evaporated to dry-
ness. Purification by column chromatography (1:6 ethyl
acetate/petroleum ether as eluant) gave N-4-
methylpentanoyl-L-(+)-2,10-camphor sultam (3.39 g,
78%).

12B. In a similar manner, but replacing 4-methylpentanoyl
chloride with the appropriate chloride, the following
compounds of formula (Fb) were prepared:

N-3-phenylpropanoyl-L-(+)-2,10-camphor sultam, MS:
347 (M$^+$);

N-5-phenylpentanoyl-L-(+)-2,10-camphor sultam, MS:
375 M$^+$;

N-pentanoyl-L-(+)-2,10-camphor sultam, MS: 300
(M+H)$^+$.

Example 13

Compounds of Formula (Fc)

13A. To a solution of N-4-methylpentanoyl-L-(+)-2,10-
camphor sultam (3.39 g, 10.8 mmol) in 75 mL of dry THF at −78° C. under argon was added NaN(TMS)$_2$ (1.0 M in THF, 11.34 mL, 1.05 eq.) dropwise over five minutes. After stirring at −78° C. for 1 hour, hexamethylphosphoramide (5 mL) was added to the mixture, followed by t-butylbromoacetate (5.2 ml, 3 eq), then 400 mg of tetra n-butyl ammonium iodide was added in one portion. The resulting solution was kept at −78° C. under argon overnight. The next morning, the reaction was quenched with water (100 mL), and then it was extracted with ether (3×100 mL). The combined ether layers were washed with brine, then dried over Na$_2$SO$_4$, filtered and concentrated. Purification by column chromatography (5:95 ethyl acetate/petroleum ether to 10:90 ethyl acetate/petroleum ether as eluant) gave N-(4-methyl-2-t-butoxycarbonylmethyl) pentanoyl-L-(+)-2,10-camphor sultam (4 g, 86.5%).

13B. In a similar manner, but replacing N-4-methylpentanoyl-L-(+)-2,10-camphor sultam with the appropriate compound of formula (Fb), the following compounds of formula (Fc) were prepared:

N-(3-phenyl-2-t-butoxycarbonylmethyl)propanoyl-L-(+)-2,10-camphor sultam, MS: 461 (M$^+$);

N-(5-phenyl-2-t-butoxycarbonylmethyl)pentanoyl-L-(+)-2,10-camphor sultam, MS: 490.1 (M+H)$^+$;

N-(2-t-butoxycarbonylmethyl)pentanoyl-L-(+)-2,10-camphor sultam, MS: 414 (M+H)$^+$.

Example 14

Compounds of Formula (F)

14A. To a stirred solution of N-(4-methyl-2-t-butoxycarbonylmethyl)pentanoyl-L-(+)-2,10-camphor sultam (5.45 g, 12.7 mmol) in 50% aqueous THF (150 mL) at 0° C. under argon was added LiOH.H$_2$O crystals (2.14 g, 4 eq.) followed by 30% H$_2$O$_2$ (11.5 mL). Then the ice-bath was removed and the resulting emulsion was stirred for 3 hours before it had turned clear. Most of the THF was removed under reduced pressure at 35° C. Then CH$_2$Cl$_2$ (150 mL) was added and with stirring 4N HCl was added to pH=2. After adding NaCl, the aqueous layer was further extracted with CH$_2$Cl$_2$ (3×150 mL). The CH$_2$Cl$_2$ was removed under reduced pressure at 35° C. and then the residue was taken up in ethyl acetate (150 mL). This solution was then extracted with 5% K$_2$CO$_3$ (3×50 mL) and the combined extracts were washed with ether (50 mL). Then CH$_2$Cl$_2$ was added to the aqueous layer and with stirring with NaCl, the aqueous layer was extracted with CH$_2$Cl$_2$ (3×70 mL) and the combined extracts were dried over Na$_2$SO$_4$, filtered and concentrated to give (2R)-4-methyl-2-t-butoxycarbonylmethyl-pentanoic acid as a colorless oil (2.95 g, quantitative yield).

14B. In a similar manner, but replacing N-(4-methyl-2-t-butoxycarbonylmethyl)pentanoyl-L-(+)-2,10-camphor sultam with the appropriate compound of formula (Fc), the following compounds of formula (F) were prepared:

(2R)-3-phenyl-2-t-butoxycarbonylmethyl-propanoic acid, MS: 265 (M+H)$^+$;

(2R)-5-phenyl-2-t-butoxycarbonylmethyl-pentanoic acid, MS: 293.1 (M+H)$^+$;

(2R)-2-t-butoxycarbonylmethyl-pentanoic acid, (colorless oil, 1.09 g).

14C. (2R)-3-Phenyl-2-t-butoxycarbonylmethyl-propanoic acid (55 mg) was taken up in glacial acetic acid (20 mL) and PtO$_2$ (25 mg) was added in acetic acid. Then the beaker was placed in a Parr bomb, it was evacuated and charged with 100 psi of H$_2$. After stirring for 3 days, the mixture was suction filtered through a 1 cm bed of celite. The filtrate was then concentrated to a yellow oil, (2R)-3-cyclohexyl-2-t-butoxycarbonylmethyl-propanoic acid (56 mg), MS: 269.5 (M–H)$^-$.

Example 15

Compounds of Formula (Ib)

15A. To a solution of 4-methyl-2-t-butoxycarbonyl-methylpentanoic acid (0.28 g, 1.2 mmol) in DMF (5 mL) containing HOBT (0.22 g, 1.8 mmol) was added EDCI (0.31 g, 1.8 mmol). The mixture was stirred at 0° C. for 1 hour and was then treated with L-cyclohexylglycine-N'-(4-methoxycarbonylphenyl)carboxamide (1.2 mmol) and DMAP (27 mg, 0.24 mmol). Stirring was continued for 24 hours at 25° C. and then the DMF was evaporated. The residue was dissolved in CH$_2$Cl$_2$ (20 mL) and the solution was washed with 1M HCl (10 mL), saturated NaHCO$_3$ (10 mL), brine (10 mL) and was dried over Na$_2$SO$_4$. Concentration in vacuo afforded an oil which was purified by flash chromatography on SiO$_2$ using 20% ethyl acetate/hexenes as element. There was obtained 0.22 g (22%) of N-(4-methyl-2-t-butoxycarbonylmethyl-pentanoyl)-L-cyclohexylglycine-N'-(4-methoxycarbonylphenyl)carboxamide as a solid, MS (FAB) 503 (MH)$^+$.

15B. In a similar manner, the following compounds were prepared:

N-(4-methyl-2-t-butoxycarbonylmethylpentanoyl)-L-pyridin-3-ylalanine-N'-(4-methoxycarbonylphenyl)carboxamide;

N-(4-methyl-2-t-butoxycarbonylmethylpentanoyl)-L-O-benzylthreonine-N'-(4-methoxycarbonylphenyl)carboxamide;

N-(4-methyl-2-t-butoxycarbonylmethylpentanoyl)-L-isoleucine-N'-(4-methoxycarbonylphenyl)carboxamide;

N-(4-methyl-2-t-butoxycarbonylmethylpentanoyl)-L-leucine-N'-(4-methoxycarbonylphenyl)carboxamide;

N-(4-methyl-2-t-butoxycarbonylmethylpentanoyl)-L-t-leucine-N'-(4-methoxycarbonylphenyl)carboxamide;

N-(4-methyl-2-t-butoxycarbonylmethylpentanoyl)-L-leucine-N'-(4-cyanophenyl)carboxamide;

N-(4-methyl-2-t-butoxycarbonylmethylpentanoyl)-L-leucine-N'-(4-(N"-(3-dimethylaminopropyl)carbamoyl)phenyl)carboxamide;

N-(4-methyl-2-t-butoxycarbonylmethylpentanoyl)-L-leucine-N'-(4-(N"-(2-dimethylaminoethyl)carbamoyl)phenyl)carboxamide;

N-(4-methyl-2-t-butoxycarbonylmethylpentanoyl)-L-leucine-N'-(4-aminosulfonylphenyl)carboxamide;

N-(4-methyl-2-t-butoxycarbonylmethylpentanoyl)-L-leucine-N'-(4-methylaminosulfonylphenyl)carboxamide;

N-(2-t-butoxycarbonylmethylpentanoyl)-L-leucine-N'-(4-methoxycarbonylphenyl)carboxamide;

N-(3-phenyl-2-t-butoxycarbonylmethylpentanoyl)-L-leucine-N'-(4-methoxycarbonylphenyl)carboxamide;

N-(3-cyclohexyl-2-t-butoxycarbonylmethylpropanoyl)-L-leucine-N'-(4-methoxycarbonylphenyl)carboxamide;

N-(4-phenyl-2-t-butoxycarbonylmethylbutanoyl)-L-leucine-N'-(4-methoxycarbonylphenyl)carboxamide; and N-(5-phenyl-2-t-butoxycarbonylmethylpentanoyl)-L-leucine-N'-(4-methoxycarbonylphenyl)carboxamide.

Example 16

Compounds of Formula (Ic)

16A. To a cold (0° C.) solution of N-(4-methyl-2-t-butoxycarbonylmethyl-pentanoyl)-L-cyclohexylglycine-N'-(4-methoxycarbonylphenyl)-carboxamide (70 mg, 0.14 mmol) in $CH_2Cl_2$ (2 mL) was added TFA (0.5 mL). After stirring for 5 hours at 25° C., the solution was concentrated in vacuo and the product was purified by reverse phase HPLC using a gradient of acetonitrile and 50 mM $NH_4OAc$ buffer to provide 44 mg (71%) of N-(4-methyl-2-carboxymethylpentanoyl)-L-cyclohexylglycine-N'-(4-methoxycarbonylphenyl)-carboxamide as a white solid, MS (FAB) 445 (M−H)⁻.

16B. In a similar manner, the following compounds were prepared:

N-(4-methyl-2-carboxymethylpentanoyl)-L-isoleucine-N'-(4-methoxycarbonylphenyl)carboxamide, MS (FAB) 419 (M−H)⁻;

N-(4-methyl-2-carboxymethylpentanoyl)-L-leucine-N'-(4-methoxycarbonylphenyl)carboxamide, MS (FAB) 419 (M−H)⁻;

N-(4-methyl-2-carboxymethylpentanoyl)-L-t-leucine-N'-(4-methoxycarbonylphenyl)carboxamide;

N-(4-methyl-2-carboxymethylpentanoyl)-L-leucine-N'-(4-cyanophenyl)carboxamide, ¹H NMR (300 MHz, NeOH) δ 0.84–0.99 (m, 12H), 1.15–1.82 (m, 6H), 2.36–2.41 (m, 1H), 2.52–2.65 (m, 1H), 2.8–2.95 (m, 1H), 4.49–4.54 (m, 1H), 7.4–7.9 (m, 4H);

N-(4-methyl-2-carboxymethylpentanoyl)-L-leucine-N'-(4-aminosulfonylphenyl)carboxamide, ¹H NMR (300 MHZ, MeOH) δ 0.85–1.00 (m, 12H), 1.1–1.3 (m, 2H), 1.52–1.85 (m, 4H), 2.31–2.95 (m, 3H), 4.49–4.55 (m, 1H), 7.75–7.91 (m, 4H);

N-(4-methyl-2-carboxymethylpentanoyl)-L-leucine-N'-(4-methylaminosulfonylphenyl)carboxamide, MS (FAB) 459 (M−H)⁻;

N-(2-carboxymethylpentanoyl)-L-leucine-N'-(4-methoxycarbonylphenyl)carboxamide, MS (FAB) 405 (M−H)⁻;

N-(3-phenyl-2-carboxymethylpropanoyl)-L-leucine-N'-(4-methoxycarbonylphenyl)carboxamide, MS (FAB) 455 (M+H)⁺;

N-(3-cyclohexyl-2-carboxymethylpropanoyl)-L-leucine-N'-(4-methoxycarbonylphenyl)carboxamide, MS (FAB) 459 (M−H)⁻;

N-(4-phenyl-2-carboxymethylbutanoyl)-L-leucine-N'-(4-methoxycarbonylphenyl)carboxamide, MS (FAB) 467 (M−H)⁻;

N-(4-phenyl-2-carboxymethylbutanoyl)-L-cyclohexylglycine-N'-(4-methoxycarbonylphenyl)carboxamide;

N-(4-phenyl-2-carboxymethylbutanoyl)-L-t-leucine-N'-(4-methoxycarbonylphenyl)carboxamide;

N-(5-phenyl-2-carboxymethylpentanoyl)-L-leucine-N'-(4-methoxycarbonylphenyl)carboxamide, MS (FAB) 481 (M−H)⁻; and N-(4-methyl-2-carboxymethylpentanoyl)-L-O-benzylthreonine-N'-(4-methoxycarbonylphenyl)carboxamide, MS (FAB) 497 (M−H)⁻.

16C. In a similar manner, but triturating the crude product with ether and then decanting the ether to yield the following compounds as TFA salts:

N-(4-methyl-2-carboxymethylpentanoyl)-L-pyridin-3-ylalanine-N'-(4-methoxycarbonylphenyl)carboxamide, MS (FAB) 456 (M+H)⁺;

N-(4-methyl-2-carboxymethylpentanoyl)-L-leucine-N'-(4-(N''-(3-dimethylaminopropyl)carbamoyl)phenyl)carboxamide, MS (FAB) 491 (M+H)⁺; and N-(4-methyl-2-carboxymethylpentanoyl)-L-leucine-N'-(4-(N''-(2-dimethylaminoethyl)carbamoyl)phenyl)carboxamide, MS (FAB) 491 (M+H)⁺.

16D. A mixture of N-(4-methyl-2-t-butoxycarbonylmethyl-pentanoyl)-L-O-benzylthreonine-N'-(4-methoxycarbonylphenyl)-carboxamide (60 mg) and Pd/C in ethyl acetate/THF (1:1, 25 mL) was hydrogenated overnight at 1 atm pressure. Filtration through Celite, concentration of the filtrate, and trituration of the residue with ether/hexenes produced N-(4-methyl-2-t-butoxycarbonylmethyl-pentanoyl)-L-threonine-N'-(4-methoxycarbonylphenyl)carboxamide, MS (FAB) 407 (M−H)⁻.

16N. By following the procedure of part A and substituting N-(4-methyl-2-t-butoxycarbonylmethyl-pentanoyl)-L-cyclohexylglycine-N'-(4-methoxycarbonylphenyl)-carboxamide with the following:

N-(2R-(t-butoxycarbonyl)methyl-5-(biphen-4-yl)pentanoyl)-L-lysine-N'-(4-(ethoxycarbonyl)phenyl)carboxamide;

N-(2R-(t-butoxycarbonyl)methyl-5-(phenyl)pentanoyl)-L-lysine-N'-(4-(ethoxycarbonyl)phenyl)carboxamide;

N-(2R-(t-butoxycarbonyl)methyl-5-(biphen-4-yl)pentanoyl)-L-(Nε-isopropyl)lysine-N'-(4-(ethoxycarbonyl)phenyl)carboxamide;

N-(2R-(t-butoxycarbonyl)methyl-4-(phenyl)butanoyl)-L-cyclohexylglycine-N'-(4-(N'',N''-dimethylaminoethylaminosulfonyl)phenyl)carboxamide;

N-(2R-(t-butoxycarbonyl)methyl-5-(phenyl)pentanoyl)-L-(N,N'-diethylguanido)lysine-N'-(4-(ethoxycarbonyl)phenyl)carboxamide;

N-(2R-(t-butoxycarbonyl)methyl-5-(biphen-4-yl)pentanoyl)-L-t-leucine-N'-(4-(methylthio)phenyl)carboxamide;

N-(2R-(t-butoxycarbonyl)methyl-5-biphen-4-yl)pentanoyl)-L-t-leucine-N'-(3-(2-hydroxyethyl)phenyl)carboxamide;

N-(2R-(t-butoxycarbonyl)methyl-5-biphen-4-yl)pentanoyl)-L-S-((4-cyanophenyl)methyl)penicillamine-N'-(phenyl)carboxamide;

N-(2R-(t-butoxycarbonyl)methyl-5-(biphen-4-yl)pentanoyl)-L-cyclohexylglycine-N'-(2-(4-aminosulfonyl)phenylethyl)carboxamide;

N-(2R-(t-butoxycarbonyl)methyl-5-(biphen-4-yl)pentanoyl)-L-cyclohexylglycine-N'-(3-(morpholin-4-yl)propyl)carboxamide;

N-(2R-(t-butoxycarbonyl)methyl-5-(biphen-4-yl)pentanoyl)-L-t-leucine-N'-(4-(methylaminosulfonyl)phenyl)carboxamide;

N-(2R-(t-butoxycarbonyl)methyl-5-(biphen-4-yl)pentanoyl)-L-cyclohexylglycine-N'-(4-((2-hydroxyethyl)aminosulfonyl)phenyl)carboxamide;

N-(2R-(t-butoxycarbonyl)methyl-5-(biphen-4-yl)pentanoyl)-L-cyclohexylglycine-N'-(4-(N'',N''-dimethylaminoethylaminosulfonyl)phenyl)carboxamide; and N-(2R-(t-butoxycarbonyl)methyl-5-(biphen-4-yl)pentanoyl)-L-t-leucine-N'-(4-((3-(morpholin-4-yl)propyl)aminosulfonyl)phenyl)carboxamide, there are obtained:

N-(2R,S)-(N"-formyl-N"-hydroxyamino)methyl-4-(methyl)pentanoyl)-L-leucine-N'-(4-(methoxycarbonyl)phenyl)carboxyamide: MS: 434.2 (M–H)⁻ 388 (M–HCO—OH);

N-(2R-(N"-hydroxycarbamoyl)methyl-4-(methyl)pentanoyl)D,L-norvaline-N'-(4-((2-(dimethylamino)ethyl)carbamoyl)phenyl)carboxamide: MS: 478 (M+H)⁺;

N-(2R-carboxymethyl-5-(biphen-4-yl)pentanoyl)-L-lysine-N'-(4-(ethoxycarbonyl)phenyl)carboxamide: MS: 588.3 (M+H)⁺;

N-(2R-carboxymethyl-5-(phenyl)pentanoyl)-L-lysine-N'-(4-(ethoxycarbonyl)phenyl)carboxamide: MS: 512.3 (M+H)⁺;

N-(2R-carboxymethyl-5-(biphen-4-yl)pentanoyl)-L-(Nε-isopropyl)lysine-N'-(4-(ethoxycarbonyl)phenyl)carboxamide: MS: 630 (M+H)⁺;

N-(2R-carboxymethyl)-4-(phenyl)butanoyl)-L-cyclohexylglycine-N'-(4-(N",N"-dimethylaminoethylaminosulfonyl)phenyl)carboxamide: MS: 586 (M+H)⁺;

N-(2R-carboxymethyl-5-(phenyl)pentanoyl)-L-(N,N'-diethylguanido)lysine-N'-(4-(ethoxycarbonyl)phenyl)carboxamide; MS: 610.4 (M+H)⁺;

N-(2R-carboxymethyl-5-(biphen-4-yl)pentanoyl)-L-t-leucine-N'-(4-(methylthio)phenyl)carboxamide: FAB-MS (M+Na)⁺ calc. 569.2450; found: 569.2461;

N-(2R-carboxymethyl-5-biphen-4-yl)pentanoyl)-L-t-leucine-N'-(3-(2-hydroxyethyl)phenyl)carboxamide: FAB-MS (M+H)⁺ calc. 545.3015; found: 545.3021;

N-(2R-carboxymethyl-5-biphen-4-yl)pentanoyl)L-S-((4-cyanophenyl)methyl)penicillamine-N'-(phenyl) carboxamide: FAB-MS (M+H)⁺ calc. 634.2740; found: 634.2749;

N-(2R-carboxymethyl-5-(biphen-4-yl)pentanoyl)-L-cyclohexylglycine-N'-(2-(4-aminosulfonyl)phenylethyl)carboxamide: FAB-MS (M+H)⁺ calc. 634.2951; found: 634.2963;

N-(2R-carboxymethyl-5-(biphen-4-yl)pentanoyl)-L-cyclohexylglycine-N'-(3-(morpholin-4-yl)propyl) carboxamide: FAB-MS (M+H)⁺ calc. 578.3594; found: 578.3583;

N-(2R-carboxymethyl-5-(biphen-4-yl)pentanoyl)-L-t-leucine-N'-(4-(methylaminosulfonyl)phenyl) carboxamide: ¹H NMR (300 MHz, acetone-d6) δ 9.73 (br, s, 1H), 7.91 (d, 2H, J=9 Hz), 7.79 (d, 2H, J=9 Hz), 7.56 (d, 2H, J=8 Hz), 7.25–7.45 (m, 6H), 7.19 (d, 2H, J=8 Hz), 4.48 (d, 1H, J=9 Hz), 2.38–3.00 (m, 9H), 1.43–1.72 (m, 4H), 1.04 (s, 9H);

N-(2R-carboxymethyl-5-(biphen-4-yl)pentanoyl)-L-cyclohexylglycine-N'-(4-((2-hydroxyethyl)aminosulfonyl)phenyl)carboxamide: FAB-MS (M+Cs)⁺ calc. 782.1876; found: 782.1896;

N-(2R-carboxymethyl-5-(biphen-4-yl)pentanoyl)-L-cyclohexylglycine-N'-(4-((2-dimethylamino)ethyl) aminosulfonyl)phenyl)carboxamide: FAB-MS (M+Cs)⁺ calc. 809.2349; found: 809.2369; and N-(2R-carboxymethyl-5-(biphen-4-yl)pentanoyl)-L-t-leucine-N'-(4-((3-(morpholin-4-yl)propyl)aminosulfonyl)phenyl)carboxamide: FAB-MS (M+H)⁺ calc. 707.3478; found: 707.3489.

Example 17

Compounds of Formula (Id)

17A. A solution of N-(4-methyl-2-carboxymethylpentanoyl)-L-leucine-N'-(4-methoxycarbonylphenyl) carboxamide (0.28 g, 0.66 mmol) and HOBT (0.12 g) in dry DMF (20 mL) was cooled to 0° C. and treated with EDCI (0.32 g). After stirring 0.5 hours at 0° C., O-benzylhydroxylamine (0.30 mL) was added and the reaction was allowed to warm to 25° C. overnight. The DMF was removed in vacuo and the residue was taken up in CH₂Cl₂ and washed with 5% HCl/5% NaHCO₃ and brine and the solution was dried over Na₂SO₄. After concentration, the product was purified by flash chromatography (SiO₂, R_f=0.6, 10% MeOH/CH₂Cl₂). The product containing fractions were further purified by trituration with CH₂Cl₂ to give N-(4-methyl-2-(N"-benzyloxycarbamoyl)methylpentanoyl)-L-leucine-N'-(4-methoxycarbonylphenyl)carboxamide as a solid, mp 198–199° C.

17B. In a similar manner, the following compounds were prepared:

N-(2-(N"-benzyloxycarbamoyl)methylpentanoyl)-L-leucine-N'-(4-methoxycarbonylphenyl)carboxamide;

N-(4-phenyl-2-(N"-benzyloxycarbamoyl)methylbutanoyl)L-leucine-N'-(4-methoxycarbonylphenyl) carboxamide; and N-(4-methyl-2-(N"-benzyloxycarbamoyl) methylpentanoyl)-L-tryptophan-N'-(4-methoxycarbonylphenyl)carboxamide.

17C. N-(4-Methyl-2-(N"-benzyloxycarbamoyl)-methylpentanoyl)-L-leucine-N'-(4-methoxycarbonylphenyl)-carboxamide (210 mg) was hydrolyzed with 1M NaOH (1.4 mL) at 50–60° C. for 2 hour in THF (20 mL) and MeOH (5 mL). The organic solvents were evaporated and the residue was taken up in 10 mL H₂O and washed with ether (2×10 mL). The aqueous phase was acidified to pH 2 with 10% HCl and extracted with ethyl acetate (3×10 mL). The combined extracts were washed with brine dried (Na₂SO₄), and concentrated to afford N-(4-methyl-2-(N"-benzyloxycarbamoyl)-methylpentanoyl)-L-leucine-N'-(4-carboxyphenyl)-carboxamide (110 mg).

Example 18

Compounds of Formula (Ie)

18A. To a solution of N-(4-phenyl-2-(N"-benzyloxycarbamoyl)methylbutanoyl)-L-leucine-N'-(4-methoxycarbonylphenyl)carboxamide (25 mg) in 20 mL MeOH and 10 mL THF was added 10% Pd/C (20 mg). The suspension was hydrogenated for 1 hour and then suction filtered through Celite. Concentration afforded the product which was purified on silica (2.5% MeOH/CH₂Cl₂) to give 8 mg of N-(4-phenyl-2-(N"-hydroxycarbamoyl)methylbutanoyl)-L-leucine-N'-(4-methoxycarbonylphenyl)carboxamide, MS (FAB) 482 (M–H)⁻.

18B. In a similar manner, the following compounds were prepared:

N-(4-methyl-2-(N"-hydroxycarbamoyl)methylpentanoyl)-L-leucine-N'-(4-carboxyphenyl)carboxamide;

N-(4-methyl-2-(N"-hydroxycarbamoyl)methylpentanoyl)-L-leucine-N'-(4-methoxycarbonylphenyl) carboxamide, MS (FAB) 436 (M+H)⁺;

N-(2-(N"-hydroxycarbamoyl)methylpentanoyl)-L-leucine-N'-(4-methoxycarbonylphenyl)carboxamide, MS (FAB) 420 (M–H)⁻;

N-(4-phenyl-2-(N"-hydroxycarbamoyl)methylbutanoyl)-L-t-leucine-N'-(4-methoxycarbonylphenyl) carboxamide;

N-(4-phenyl-2-(N"-hydroxycarbamoyl)methylbutanoyl)-L-cyclohexylglycine-N'-(4-methoxycarbonyl-phenyl)carboxamide;

N-(4-phenyl-2-(N"-hydroxycarbamoyl)methylbutanoyl)-L-leucine-N'-(4-methoxycarbonylphenyl)carboxamide;

N-(4-methyl-2-(N"-hydroxycarbamoyl)methylpentanoyl)-L-t-leucine-N'-(4-methoxycarbonylphenyl)carboxamide;

N-(4-methyl-2-(N"-hydroxycarbamoyl)methylpentanoyl)-L-tryptophan-N'-(4-methoxycarbonylphenyl)carboxamide, MS (FAB) 507 (M–H)⁻; and N-(4-phenyl-2-(N"-hydroxycarbamoyl)methylbutanoyl)-L-leucine-N'-(4-methoxycarbonylphenyl)carboxamide.

18C. In a similar manner, the following compounds are prepared:

N-(3-phenyl-2-(N"-hydroxycarbamoyl)methylpropanoyl)-L-leucine-N'-(4-methoxycarbonylphenyl)carboxamide;

N-(5-phenyl-2-(N"-hydroxycarbamoyl)methylpentanoyl)-L-leucine-N'-(4-methoxycarbonylphenyl)carboxamide; and N-(3-cyclohexyl-2-(N"-hydroxycarbamoyl)methylpropanoyl)-L-leucine-N'-(4-methoxycarbonyl-phenyl)carboxamide.

Example 19

Compounds of Formula (Gb)

19A. To a cold (0° C.) solution of diethyl isobutylmalonate (21.6 g, 0.1 mol) in 150 mL of ethanol was added a solution of KOH (5.89 g, 0.1 mol) slowly over 30 minutes. The clear solution was stirred at 25° C. for 60 hours. The ethanol was removed under reduced pressure and the solid residue was dissolved in 50 mL of $H_2O$. The aqueous solution was acidified to pH 2 with 4M HCl and extracted with ether (2×50 mL). The combined extracts were dried over $MgSO_4$ and evaporated to provide 19.0 g (100%) of ethyl isobutylmalonate as a colorless oil.

19B. In a similar manner, the following compounds of formula (Gb) are prepared: ethyl tert-butylmalonate; ethyl propylmalonate; ethyl benzylmalonate; and ethyl cyclohexymethylmalonate.

Example 20

Compounds of Formulae (Gc) and (Gd)

20A. To neat ethyl isobutylmalonate (25 g, 0.13 mol) at 0° C. was slowly added ice cold diethylamine (15.1 mL, 0.15 mol). After stirring for 15 minutes, formalin (11.1 mL of 37% aqueous formaldehyde) was added dropwise and the mixture was allowed to stir at 25° C. for 3 days. The reaction was treated with a solution of 20 g of $K_2CO_3$ in 40 mL $H_2O$ and extracted with ether (2×100 mL). The combined ether layers were washed with brine, dried over $MgSO_4$, and evaporated at 20° C. on a rotary evaporator. The crude product ethyl 4-methyl-2-methylenepentanoate (containing some ether) was dissolved in 250 mL of absolute ethanol and treated with acetonitrile (250 mL), 1M LiOH (9.7 g in 250 mL of $H_2O$, 0.23 mol). After stirring overnight, the organic solvents were evaporated and the aqueous residue was extracted with ethyl acetate (2×150 mL). The combined extracts were washed with brine, dried ($MgSO_4$), and evaporated to afford 10.5 g of 4-methyl-2-methylenepentanoic acid as a colorless oil.

20B. In a similar manner, the following compounds of formula (Gd) are prepared: 4-phenyl-2-methylenebutanoic acid; 3-cyclohexyl-2-methylenepropanoic acid; 5-phenyl-2-methylenepentanoic acid; 2-methylenepentanoic acid; and 3,3-dimethyl-2-methylenebutanoic acid.

Example 21

Compounds of Formula (G)

A mixture of 4-methyl-2-methylenepentanoic acid (5.0 g) and thioacetic acid (25 mL) was heated at 95° C. under argon for 3 days. The excess thioacetic acid was evaporated and the residual oil was dissolved in ethyl acetate (40 mL) and extracted with saturated $NaHCO_3$ (3×40 mL). The combined $NaHCO_3$ extracts were combined and acidified at 0° C. to pH 2 with 1M HCl. The aqueous layer was extracted with $CH_2Cl_2$ (3×40 mL), the combined organic phases were dried ($MgSO_4$) and evaporated to give 3.0 g of 4-methyl-2-acetylthiomethyl-pentanoic acid; $^1H$ NMR (80 MHz, $CDCL_3$) δ 0.95 (d, J=8.0, 6H), 1.20–1.90 (m, 4H), 2.35 (s, 3H), 2.50–3.20 (m, 3H), 6.7 (br s, 1H).

Example 22

Compounds of Formula (If)

22A. To a solution of 4-methyl-2-acetylthiomethylpentanoic acid (204 mg, 1.0 mmol) in dry DMF (15 mL) containing HOBT (92 mg, 0.6 mmol) and L-leucine-N'-(4-methoxycarbonylphenyl)carboxamide (0.6 mmol) was added EDCI (345 mg, 1.8 mmol). The solution was stirred overnight at 25° C. and then the DMF was removed in vacuo. The residue was dissolved in ethyl acetate (35 mL) and washed with 1M, HCl, 1M NaOH, and brine. Drying over $MgSO_4$ and evaporation afforded a semisolid which was flash chromatographed on silica gel (ethyl acetate 1:petroleum ether 2) to give N-(4-methyl-2-acetylthiomethylpentanoyl)-L-leucine-N'-(4-methoxycarbonylphenyl)carboxamide (190 mg) as a white solid.

22B. In a similar manner, the following compounds of formula (If) are prepared:

N-(5-phenyl-2-acetylthiomethylpentanoyl)-L-leucine-N'-(4-methoxycarbonylphenyl)carboxamide;

N-(4-phenyl-2-acetylthiomethylbutanoyl)-L-leucine-N'-(4-methoxycarbonylphenyl)carboxamide;

N-(3-phenyl-2-acetylthiomethylpropanoyl)-L-leucine-N'-(4-methoxycarbonylphenyl)carboxamide;

N-(3-cyclohexyl-2-acetylthiomethylpropanoyl)-L-leucine-N'-(4-methoxycarbonylphenyl)carboxamide;

N-(2-acetylthiomethylpentanoyl)-L-leucine-N'-(4-methoxycarbonylphenyl)carboxamide;

N-(5-phenyl-2-acetylthiomethylpentanoyl)-L-leucine-N'-(4-aminocarbonylphenyl)carboxamide;

N-(4-phenyl-2-acetylthiomethylbutanoyl)-L-leucine-N'-(4-carboxyphenyl)carboxamide;

N-(3-phenyl-2-acetylthiomethylpropanoyl)-L-leucine-N'-(4-methylsulfonylphenyl)carboxamide;

N-(3-cyclohexyl-2-acetylthiomethylpropanoyl)-L-leucine-N'-(4-carbamoylphenyl)carboxamide;

N-(2-acetylthiomethylpentanoyl)-L-leucine-N'-(4-cyanophenyl)carboxamide;

N-(5-phenyl-2-acetylthiomethylpentanoyl)-L-tryptophan-N'-(4-methoxycarbonylphenyl)carboxamide;

N-(4-phenyl-2-acetylthiomethylbutanoyl)-L-tryptophan-N'-(4-methoxycarbonylphenyl)carboxamide;

N-(3-phenyl-2-acetylthiomethylpropanoyl)-L-tryptophan-N'-(4-methoxycarbonylphenyl)carboxamide;

N-(3-cyclohexyl-2-acetylthiomethylpropanoyl)-L-tryptophan-N'-(4-methoxycarbonylphenyl)carboxamide; and N-(2-acetylthiomethylpentanoyl)-L-tryptophan-N'-(4-methoxycarbonylphenyl)carboxamide.

Example 23

Compounds of Formula (Ig)

23A. To a solution of N-(4-methyl-2-acetylthiomethylpentanoyl)-L-leucine-N'-(4-methoxycarbonylphenyl)carboxamide (85 mg, 0.19 mmol) in MeOH (8 mL) at 0° C. was added concentrated $HN_4OH$ (0.4 mL). After stirring at 0° C. for 5 hours, the methanol was evaporated and ether (30 mL) was added. The ether solution was washed with 0.5 M HCl, brine, and was dried over $MgSO_4$. Concentration afforded N-(4-methyl-2-mercaptomethylpentanoyl)-L-leucine-N'-(4-methoxycarbonyl-phenyl)carboxamide in quantitative yield as a white foam, MS (FAB) 407 (M–H)$^-$.

23B. In a similar manner, the following compounds of formula (Ig) are prepared:

N-(5-phenyl-2-mercaptomethylpentanoyl)-L-leucine-N'-(4-methoxycarbonylphenyl)carboxamide;

N-(4-phenyl-2-mercaptomethylbutanoyl)-L-leucine-N'-(4-methoxycarbonylphenyl)carboxamide;

N-(3-phenyl-2-mercaptomethylpropanoyl)-L-leucine-N'-(4-methoxycarbonylphenyl)carboxamide;

N-(3-cyclohexyl-2-mercaptomethylpropanoyl)-L-leucine-N'-(4-methoxycarbonylphenyl)carboxamide;

N-(2-mercaptomethylpentanoyl)-L-leucine-N'-(4-methoxycarbonylphenyl)carboxamide;

N-(5-phenyl-2-mercaptomethylpentanoyl)-L-leucine-N'-(4-aminocarbonylphenyl)carboxamide;

N-(4-phenyl-2-mercaptomethylbutanoyl)-L-leucine-N'-(4-carboxyphenyl)carboxamide;

N-(3-phenyl-2-mercaptomethylpropanoyl)-L-leucine-N'-(4-methylsulfonylphenyl)carboxamide;

N-(3-cyclohexyl-2-mercaptomethylpropanoyl)-L-leucine-N'-(4-carbamoylphenyl)carboxamide;

N-(2-mercaptomethylpentanoyl)-L-leucine-N'-(4-cyanophenyl)carboxamide;

N-(5-phenyl-2-mercaptomethylpentanoyl)-L-tryptophan-N'-(4-methoxycarbonylphenyl)carboxamide;

N-(4-phenyl-2-mercaptomethylbutanoyl)-L-tryptophan-N'-(4-methoxycarbonylphenyl)carboxamide;

N-(3-phenyl-2-mercaptomethylpropanoyl)-L-tryptophan-N'-(4-methoxycarbonylphenyl)carboxamide;

N-(3-cyclohexyl-2-mercaptomethylpropanoyl)-L-tryptophan-N'-(4-methoxycarbonylphenyl)carboxamide; and N-(2-mercaptomethylpentanoyl)-L-tryptophan-N'-(4-methoxycarbonylphenyl)carboxamide.

Example 24

Formula (Fc")

To a stirred solution of 6.48 g (25.0 mmol) of N-(4-pentenoyl)-4S-phenylmethyl-2-oxazolidinone in 50 mL of dry THF under argon at –95° C. was added 27.5 mL (27.5 mmol) of 1.0 M sodium hexamethyldisilazide in THF via syringe at a rate to maintain the reaction temperature at less than –75° C. After 15 min at –80° C. to –95° C., 5.65 mL (6.83 g, 35 mmol) of t-butyl bromoacetate, which had been filtered through basic alumina immediately prior to use, was added via syringe over a 1 min period. The solution was stirred at –90° C. to –60° C. for 2 h, and then partitioned between hexane (100 mL) and dilute aq. $NaHSO_4$. The organic layer was washed with sat. aq. NaCl containing a little 1 M phosphate buffer (pH 7), dried over $Na_2SO_4$, and concentrated. The residue was recrystallized from 75 mL of hexane to give 5.56 g (60%) of N-(2R-(t-Butoxycarbonyl)methyl-4-pentenoyl)-4S-phenylmethyl-2-oxazolidinone as pale yellow needles: mp 75–76° C.

El. Anal. Calc. for $C_{21}H_{27}NO_5$: C, 67.54; H, 7.29, N, 3.75. Found: C, 67.76; H, 7.34; N, 3.87.

Example 25

Formula (Fc"-1) Where $R^2$ is Biphenyl

To a solution of 4.75 g (12.7 mmol) of N-(2R-(t-Butoxycarbonyl)methyl-4-pentenoyl)-4S-phenylmethyl-2-oxazolidinone, 3.73 g (16.0 mmol) of 4-bromobiphenyl, 0.234 g (0.77 mmol) of tri-o-tolylphosphine, and 2.22 mL (1.62 g, 16.0 mmol) of triethylamine in 10 mL of anhydrous DMF under argon was added 0.086 g (0.385 mmol) of palladium(II) acetate. The solution was heated at 100° C. for 4 h, cooled to room temperature, diluted with ethyl acetate. The precipitate was removed by filtration, and the filtrate was partitioned between 150 mL of 2:1 ethyl acetate:hexane and 50 mL of pH 7 phosphate buffer (0.5 M) containing a little sodium sulfite. The organic layer was washed with 0.2 N aq. sodium bisulfate and brine/pH 7 phosphate buffer, dried over sodium sulfate, and concentrated. The residue was dissolved in 50 mL of ethyl acetate, diluted with 250 mL of isooctane, and seeded with a few crystals of the product. The solid was removed by filtration, and recrystallized from 250 mL of 4:1 isooctane:ethyl acetate to give 4.20 g (63%) of the product, N-(2R-(t-Butoxycarbonyl)methyl-(5-(biphen-4-yl)-4-pentenoyl)-4S-phenylmethyl-2-oxazolidinone, as fine white needles: mp 118–119° C.; $^1$H NMR (300 MHz, $CDCl_3$) 7.25–7.60 (m, 14H), 6.47 (d, 1H, J=16 Hz), 6.25 (dt, 1H, J=16 and 8 Hz), 4.65–4.70 (m, 1H), 4.34–4.44 (m, 1H), 4.11 (dd, 1H, J=9 and 2 Hz), 4.01 (t, 1H, J=8 Hz), 3.33 (dd, 1H, J=14 and 3 Hz), 2.89 (dd, 1H, J=17 and 11 Hz), 2.76 (dd, 1H, J=14 and 10 Hz), 2.40–2.57 (m, 3H), 1.43 (s, 9H).

El. Anal. Calc. for $C_{37}H_{35}NO_5$: C, 75.40; H, 6.77, N, 2.66. Found: C, 75.17; H, 6.84; N, 2.58.

Example 26

Formula (Fc"-2) Where $R^3$ is Biphenyl

A solution of 5.23 g (10.00 mmol) of N-(2R-(t-butoxycarbonyl)methyl-(5-(biphen-4-yl)-4-pentenoyl)-4S-phenylmethyl-2-oxazolidinone in 50 mL of ethyl acetate was hydrogenated at 1 atm of hydrogen over 500 mg of 10% Pd/C for 2 h at room temperature. The catalyst was removed by filtration through Celite, and the filtrate was concentrated to about 20 mL, then diluted with about 75 mL of isooctane. The solution was seeded with a few crystals of the product, and the mixture was concentrated to about 50 mL, then cooled to –20° C. Filtration of the precipitate gave 4.91 g (94%) of N-(2R-(t-butoxycarbonyl)methyl-(5-(biphen-4-yl) pentanoyl)-4S-phenylmethyl-2-oxazolidinone as a white powder: mp: 75–76° C.; $^1$H NMR (300 MHz, CDCl$_3$) 7.22–7.59 (m, 14H), 4.61–4.70 (m, 1H), 4.18–4.24 (m, 1H), 4.14 (d, 2H, J=5 Hz), 3.34 (dd, 1H, J=13 and 3 Hz), 2.57–2.89 (m, 4H), 2.48 (dd, 1H, J=13 and 5 Hz), 1.65–1.83 (m, 3H), 1.50–1.60 (m, 1H), 1.42 (s, 9H).

El. Anal. Calc. for C$_{33}$H$_{37}$NO$_5$: C, 75.11; H, 7.07, N, 2.65. Found: C, 75.34; H, 7.11; N, 2.69.

Example 27

Formula F Where R$^2$ is Biphenyl

To a solution of 4.02 g (7.62 mmol) of N-(2R-(t-butoxycarbonyl)methyl-(5-(biphen-4-yl)pentanoyl)-4S-phenylmethyl-2-oxazolidinone in 60 mL of THF at 0° C. was added 2.8 mL of 30% aq. hydrogen peroxide followed by 8.0 mL of 2 N aq. lithium hydroxide. The mixture was stirred vigorously at 0° C. for 15 min, and then allowed to warm to room temperature. After 2 h, the mixture was cooled to 0° C., and 20 mL of 2 N aq. sodium sulfite and 30 mL of saturated aq. sodium bicarbonate were added. After 10 min at 0° C., the mixture was stirred an additional 1 h at room temperature and then poured into 1 M pH 7 phosphate buffer. The aqueous phase was acidified to pH 6 by addition of solid sodium bisulfate, and then the mixture was extracted with 1:1 ethyl acetate:hexane (200 mL). The organic layer was. washed with brine, dried over sodium sulfate, and concentrated. The residue was chromatographed on 125 g of silica gel, eluting with 20% to 30% ethyl acetate:hexane containing 0.5% acetic acid. The product-containing fractions were concentrated and then azeotroped several times with toluene to give 2.93 (>100%) of the product, 2R-(t-butoxycarbonyl)methyl-(5-(biphen-4-yl)pentanoic acid, as a thick syrup which slowly solidified upon storage at −20° C.: mp 44–45° C. (after drying solid in vacuo); $^1$H NMR (300 MHz, CDCl$_3$) δ 7.22–7.59 (m, 9H), 2.82–2.90 (m, 1H), 2.59–2.75 (m, 3H), 2.40 (dd, 1H, J=14 and 5 Hz), 1.55–1.80 (m, 4H), 1.42 (s, 9H).

El. Anal. Calc. for C$_{23}$H$_{28}$O$_4$: C, 74.97; H, 7.66. Found: C, 75.08; H, 7.76.

Example 28

Formula (A-1)

To a solution of 5.00 g (21.6 mmol) of N-(t-butoxycarbonyl)-L-t-leucine and 2.50 g (21.7 mmol) of N-hydroxysuccinimide in 40 mL of acetonitrile at 0° C. was added dropwise a solution of 4.12 g (20 mmol) of dicyclohexylcarbodiimide in 40 mL of acetonitrile. The mixture was stirred at 0° C. to room temperature overnight, and then the mixture was filtered to remove the precipitated dicyclohexylurea. The filtrate was concentrated and the residue was triturated with ethyl acetate/dichloromethane to give 5.06 g (80%) of N-(t-Butoxycarbonyl)-L-t-leucine, N-hydroxysuccinimide ester as a white solid: mp 136–137° C.; $^1$H NMR (300 MHz, CDCl$_3$) δ 5.07 (br d, 1H), 4.43 (d, 1H, J=10 Hz), 2.84 (s, 4H), 1.46 (s, 9H), 1.10 (s, 9H).

Example 29

Formula (C) Where R$^3$ is t-Butyl, and R$^7$ is 4-Pyridine (in Place of the Illustrated Phenyl Group)

A solution of 2.00 g (6.32 mmol) of N-(t-butoxycarbonyl)-L-t-leucine, N-hydroxysuccinimide ester and 2.98 g (31.6 mmol) of 4-aminopyridine in 20 mL of dioxane was heated at 100° C. for 3 h. The reaction was cooled to room temperature and concentrated. The residue was purified by chromatography on silica gel, eluting with 5% to 10% methanol in dichloromethane, to give 1.06 g (54%) of N-(t-butoxycarbonyl)-L-t-leucine-N'-(pyrid-4-yl) carboxamide as a white solid: $^1$H NMR (300 MHz, CDCl$_3$) δ 8.47 (d, 2H, J=6 Hz), 8.35 (br s, 1H), 7.50 (d, 2H, J=6 Hz), 5.23 (broad d, 1H), 4.00 (br d, 1H), 1.44 (s, 9H), 1.05 (s, 9H).

FAB-MS ((M+H)$^+$ calculated: 308.1974 observed: 308.1970.

Example 30

30A. Formula (D) Where R$^3$ in t-Butyl, and R$^7$ is 4-Pyridine (in Place of the Illustrated Phenyl Group)

To a solution of 132 mg (0.43 mmol) of N-(t-butoxycarbonyl)-L-t-leucine-N'-(pyrid-4-yl)carboxamide in 2 mL of dichloromethane was added 1 mL of trifluoroacetic acid. After 1 h at room temperature, the solution was diluted with ca. 5 mL of toluene and concentrated. Repeated dissolution in toluene/dichloromethane/methanol and concentration eventually provided 190 mg (100%) of L-t-leucine-N'-(pyrid-4-yl)carboxamide bis(trifluoroacetate) as a white solid: $^1$H NMR (300 MHz, DMSO-d6) δ 11.58 (br s, 1H), 8.68 (d, 2H, J=6 Hz), 8.35 (br s, 2H), 7.91 (d, 2H, J=6 Hz), 3.81 (s, 1H), 1.04 (s, 9H).

FAB-MS ((M+H)$^+$ calculated: 208.1500 observed: 208.1496.

30B. Formula (D) Where R$^3$ is t-Butyl, and R$^7$ is 4-(Methylthio)phenyl

In a manner analogous to that of part A was prepared L-t-leucine-N'-(4-(methylthio)phenyl)carboxamide: $^1$H NMR (300 MHz, CDCl$_3$) δ 9.02 (s, 1H), 7.49 (d, 2H, J=6.5 Hz), 7.23 (d, 2H, J=6.5 Hz), 3.23 (s, 2H); 2.44 (s, 3H), 1.03 (s, 9H).

Example 31

31A. Formula (Ib) Where R$^2$ is Biphenyl (and X is Propanyl), R$^3$ and R$^8$ are t-Butyl, and R$^7$ is 4-Pyridine (in Place of the Illustrated Phenyl Group)

To a solution of 357 mg (0.97 mmol) of 2R-(t-butoxycarbonyl)methyl-(5-(biphen-4-yl)pentanoic acid, 422 mg (0.97 mmol) of L-t-leucine-N'-(4-(pyrid-4-yl) carboxamide bis(trifluoroacetate), and 0.50 mL (3.6 mmol) of triethylamine in 5 mL of DMF was added 442 mg (1.00 mmol) of benzotriazol-1-yl-tris-(dimethylamino) phosphonium hexafluorophosphate. After 4 h, the reaction was partitioned between ethyl acetate and water. The aqueous layer was extracted twice with ethyl acetate, and the combined organic layers were washed with water and with brine, dried over sodium sulfate, and concentrated. Purification of the residue by silica gel chromatography, eluting with 25% to 75% ethyl acetate in hexane, gave 360 mg (66%) of N-(2R-(t-butoxycarbonyl)methyl-5-(biphen-4-yl) pentanoyl)-L-t-leucine-N'-(pyrid-4-yl)carboxamide: $^1$H NMR (300 MHz, CDCl$_3$) δ 8.52 (s, 1H), 8.42 (d, 2H, J=6 Hz), 7.54 (d, 2H, J=7 Hz), 7.40–7.48 (m, 6H), 7.32 (t, 1H, J=7 Hz), 7.13 (d, 2H, J=8 Hz), 6.62 (d, 1H, J=9 Hz), 4.35 (d, 1H, J=9 Hz), 2.58–2.68 (m, 4H), 2.40 (dd, 1H, J=16 and 3 Hz), 1.40–1.75 (s over m, obscured by H$_2$O, 13H), 1.08 (s, 9H).

31B. Formula (Ib) Varying R$^7$

By following the procedure of part A and substituting L-t-leucine-N'-(4-(pyrid-4-yl)carboxamide bis (trifluoroacetate) with the following: L-t-leucine-N'-(4-((2-hydroxyethyl)aminosulfonyl)phenyl)carboxamide; L-t-leucine-N'-(4-(methylthio)phenyl)carboxamide; there are obtained:

N-(2R-(t-butoxycarbonyl)methyl-5-(biphen-4-yl)
pentanoyl)-L-t-leucine-N'-(4-((2-hydroxyethyl)
aminosulfonyl)phenyl)carboxamide: mp 89–92° C.; $^1$H
NMR (300 MHz, methanol-d4) δ 7.80 (s, 4H), 7.51 (d,
2H, J=7 Hz), 7.41 (d, 2H, J=7 Hz), 7.36 (d, 2H, J=8
Hz), 7.28 (t, 1H, J=7 Hz), 7.14 (d, 2H, J=8 Hz), 4.47 (s,
1H), 3.47 (t, 2H, J=6 Hz), 2.85–2.95 (t overlapping m,
3H), 2.52–2.62 (m, 3H), 2.32 (dd, 1H, J=16.5 and 5
Hz), 1.48–1.62 (m, 4H), 1.41 (s, 9H), 1.09 (s, 9H); El.
Anal. Calc. for $C_{37}H_{49}N_3O_7S$: C, 65.37; H, 7.26; N,
6.18; S, 4.72. Found: C, 65.13; H, 7.33; N, 6.22; S,
4.63;

N-(2R-(t-butoxycarbonyl)methyl-5-(biphen-4-yl)
pentanoyl)-L-t-leucine-N'-(4-(methylthio)phenyl)
carboxamide: $^1$H NMR (300 MHz, CDCl$_3$) δ 7.79 (s,
1H), 7.53 (d, 2H, J=7 Hz), 7.31–7.44 (m, 7H), 7.19 (d,
2H, J=9 Hz), 7.13 (d, 2H, J=8 Hz), 6.58 (d, 1H, J=9
Hz), 4.36 (d, 1H, J=9 Hz), 2.55–2.67 (m, 4H),
2.34–2.40 (s overlapping m, 4H), 1.38–1.75 (s over-
lapping m, 13H), 1.07 (s, 9H); El. Anal. Calc. for
$C_{36}H_{46}NO_4S.0.25H_2O$: C, 71.19; H, 7.72, N, 4.61, S,
5.28. Found: C, 71.20; H, 7.78, N, 4.58, S, 5.28;

Example 32

32A. Formula (Ic) Where R$^2$ is Biphenyl (and X is
Propanyl), R$^3$ is t-Butyl, and R$^7$ is 4-Pyridine (in Place of
the Illustrated Phenyl Group)

To a solution of 360 mg (0.64 mmol) of N-(2R-(t-
butoxycarbonyl)methyl-5-(biphen-4-yl)pentanoyl)-L-t-
leucine-N'-(pyrid-4-yl)carboxamide in 4 mL of dichlo-
romethane was added 2 mL of trifluoroacetic acid. After 1 h
at room temperature, the solution was diluted with toluene
and concentrated. The residue was dissolved in ethyl acetate
(15 mL) and washed with 0.5 N pH 4 citrate buffer (2×15
mL). The combined aq. layers were extracted with ethyl
acetate (2×15 mL), and the combined organic layers were
washed with brine, dried over sodium sulfate, and concen-
trated. The residue was triturated with ethyl acetate/hexane
to give 230 mg (71%) of N-(2R-carboxymethyl-5-(biphen-
4-yl)pentanoyl)-L-t-leucine-N'-(pyridin-4-yl)carboxamide
as a white solid: mp 198–201° C.; $^1$H NMR (300 MHz,
MeOH-d4) δ 8.32 (d, 2H, J=7 Hz), 7.64 (d, 2H, J=5 Hz),
7.45 (d, 2H, J=7 Hz), 7.24–7.38 (m, 7H), 7.10 (d, 2H, J=8
Hz), 4.42 (s, 1H), 2.85–3.00 (m, 1H), 2.33–2.65 (m, 4H),
1.40–1.62 (m, 4H), 1.02 (s, 9H).

El. Anal. Calc. for $C_{30}H_{36}N_3O_4.0.5H2O.0.5$ ethyl acetate
(solvate): C, 69.29; H, 7.27, N, 7.58. Found: C, 69.46; H,
7.09; N, 7.55.

32B. Formula (Ic) Varying R$^7$

By following the procedure of part A and substituting
N-(2R-(t-butoxycarbonyl)-methyl-5-(biphen-4-yl)
pentanoyl)-L-t-leucine-N'-(pyrid-4-yl)carboxamide with the
following:

N-(2R-(t-butoxycarbonyl)methyl-5-(biphen-4-yl)
pentanoyl)-L-t-leucine-N'-(4-((2-hydroxyethyl)
aminosulfonyl)phenyl)carboxamide;

N-(2R-(t-butoxycarbonyl)methyl-5-(biphen-4-yl)
pentanoyl)-L-t-leucine-N-'(4R/S-(methylsulfinyl)
phenyl)carboxamide;

N-(2R-(t-butoxycarbonyl)methyl-5-(fluoren-2-yl)
pentanoyl)-L-leucine-N'-(4-(methoxycarbonyl)phenyl)
carboxamide;

N-(2R-(t-butoxycarbonyl)methyl-5-(7-(glycyl)
aminofluoren-2-yl)pentanoyl)-L-leucine-N'-(4-
(methoxycarbonyl)phenyl)carboxamide;

N-(2R-(t-butoxycarbonyl)methyl-5-(4-(pyrid-4-yl)
phenyl)pentanoyl)-L-leucine-N'-(4-(methoxycarbonyl)
phenyl)carboxamide;

N-(2R-(t-butoxycarbonyl)methyl-5-(biphen-4-yl)
pentanoyl)-L-β-hydroxyvaline-N'-(phenyl)
carboxamide;

N-(2R-(t-butoxycarbonyl)methyl-5-(biphen-4-yl)
pentanoyl)-L-t-leucine-N'-(4-(methyl-sulfonyl)phenyl)
carboxamide;

N-(2R-(t-butoxycarbonyl)methyl-5-(4-(2-hydroxyethyl)
phenyl)pentanoyl)-L-leucine-N'-(4-(methoxycarbonyl)
phenyl)carboxamide;

N-(2R-(t-butoxycarbonyl)methyl-5-(4'-hydroxybiphen-4-
yl)pentanoyl)-L-leucine-N'-(4-(methoxycarbonyl)
phenyl)carboxamide;

N-(2R-(t-butoxycarbonyl)methyl-5-(4'-cyanobiphen-4-
yl)pentanoyl)-L-leucine-N'-(4-(methoxycarbonyl)
phenyl)carboxamide;

N-(2R-(t-butoxycarbonyl)methyl-5-(biphen-4-yl)
pentanoyl)-L-leucine-N'-(4-(methoxycarbonyl)phenyl)
carboxamide;

N-(2R-(t-butoxycarbonyl)methyl-5-(4'-(2-aminoethoxy)
biphen-4-yl)pentanoyl)-L-leucine-N'-(4-
(methoxycarbonyl)phenyl)carboxamide;

N-(2R-(t-butoxycarbonyl)methyl-5-(4-(pyridin-4-yl)
phenyl)pentanoyl)-L-cyclohexylglycine-N'-(4-((2-
hydroxyethyl)aminosulfonyl)phenyl)carboxamide;

N-(2R-(t-butoxycarbonyl)methyl-5-(biphen-4-yl)
pentanoyl)-L-threonine-N'-(4S-(methylsulfinyl)
phenyl)carboxamide;

N-(2R-(t-butoxycarbonyl)methyl-5-(2-fluorobiphen-4-yl)
pentanoyl)-L-leucine-N'-(4-(methoxycarbonyl)phenyl)
carboxamide;

N-(2R-(t-butoxycarbonyl)methyl-4-((biphen-4-yl)thio)
butanoyl)-L-t-leucine-N'-(pyridin-4-yl)carboxamide;

N-(2R-(t-butoxycarbonyl)methyl-5-(4-(2-aminopyridin-
5-yl)phenyl)pentanoyl)-L-threonine-N'-(4S-
(methylsulfinyl)phenyl)carboxamide;

N-(2R-(t-butoxycarbonyl)methyl-5-(2-hydroxybiphen-4-
yl)pentanoyl)-L-threonine-N'-(4S-(methylsulfinyl)
phenyl)carboxamide;

N-(2R-(t-butoxycarbonyl)methyl-5-(4'-cyanobiphen-4-
yl)pentanoyl)-L-(trans-4-hydroxycyclohexyl)glycine-
N'-(4S-(methylsulfinyl)phenyl)carboxamide;

N-(2R-(t-butoxycarbonyl)methyl-5-(biphen-4-yl)
pentanoyl)-L-(4-hydroxytetrahydropyran-4-yl)glycine-
N'-(4S-(methylsulfinyl)phenyl)carboxamide; and N-(2R-(t-butoxycarbonyl)methyl-5-(2R/S-hydroxy-3,3,
3-trifluoropropyl)phenyl)pentanoyl)-L-(cyclohexyl)
glycine-N'-(4S-(4-((2-hydroxyethyl)aminosulfonyl)
phenyl)carboxamide, there are obtained:

N-(2R-carboxymethyl-5-(biphen-4-yl)pentanoyl)-L-t-
leucine-N'-(4-((2-hydroxyethyl)aminosulfonyl)
phenyl)carboxamide: $^1$H NMR (300 MHz, MeOH-
d4) δ 7.80 (s, 4H), 7.50 (d, 2H, J=7 Hz), 7.25–7.42
(m, 5H), 7.15 (d, 1H, J=8 Hz), 4.47 (s, 1H), 3.47 (t,
2H, J=6 Hz), 2.89–3.00 (m, 1H), 2.87 (t, 2H, J=6
Hz), 2.49–2.70 (m, 3H), 2.39 (dd, 1H, J=16 and 5
Hz), 1.46–1.67 (m, 4H), 1.07 (s, 9H); El. Anal. Calc.
for $C_{33}H_{41}N_3O_7S.0.5H_2O$: C, 62.64; H, 6.69; N,
6.64; S, 5.07. Found: C, 62.61; H, 6.80; N, 6.31; S,
4.97;

N-(2R-carboxymethyl-5-(biphen-4-yl)pentanoyl)-L-t-
leucine-N'-(4R/S-(methylsulfinyl)phenyl)
carboxamide: $^1$H NMR (300 MHz, MeOH-d4) δ
8.03 (d, 1H, J=9 Hz), 7.76 (d, 2H, J=9 Hz), 7.57 (dd, 2H, J=9 and 2 Hz), 7.44 (d, 2H, J=7 Hz), 7.36 (t, 2H, J=7 Hz), 7.23–7.28 (m, 3H), 7.10 (d, 2H, J=8 Hz), 4.45 (d, 1H, J=9 Hz), 2.85–2.98 (m, 1H, J=8 Hz), 2.44–2.64 (m, 7H), 2.35 (dd, 1H, J=16 and 5 Hz), 1.43–1.62 (m, 4H), 1.03 (s, 9H);

N-(2R-carboxymethyl-5-(fluoren-2-yl)pentanoyl)-L-leucine-N'-(4-(methoxycarbonyl)phenyl)carboxamide mp 188–190° C.; $^1$H NMR (300 MHz, CDCl$_3$) δ 12.06 (s, 1H), 10.30 (s, 1H), 8.19 (d, 1H, J=8 Hz), 7.86 (d, 2H, J=9 Hz), 7.68–7.77 (m, 3H), 7.62 (d, 1H, 8 Hz), 7.48 (d, 1H, J=7 Hz), 7.20–7.35 (m, 3H), 7.10 (d, 1H, J=7 Hz), 4.48 (m, 1H), 3.76 (s, 3H), 3.70 (s, 2H), 2.15–2.75 (, 5H), 1.35–1.75 (m, 5H), 0.90–0.99 (m, 4H); El. Anal. Calc. for $C_{34}H_{38}N_2O_6$: C, 71.56; H, 6.71, N, 4.91. Found: C, 71.51; H, 6.97; N, 4.84;

N-(2R-carboxymethyl-5-(7-(glycyl)aminofluoren-2-yl)pentanoyl)-L-leucine-N'-(4-(methoxycarbonyl)phenyl)carboxamide: mp 222–224° C. FAB-MS (M+H)$^+$ calculated for $C_{40}H_{51}N_4O_7$: 699.3758; observed: 699.3770;

N-(2R-carboxymethyl-5-(4-(pyrid-4-yl)phenyl)pentanoyl)-L-leucine-N'-(4-(methoxycarbonyl)phenyl)carboxamide: $^1$H NMR (300 MHz, d$_4$-MeOH) δ 8.52 (d, 2H, J=5.5 Hz), 7.92 (d, 2H, J=9.19 Hz), 7.67 (d, 2H, J=8.82 Hz), 7.58 (d, 2H, J=6.25 Hz), 7.46 (d, 2H, J=8.45 Hz), 7.20 (d, 2H, J=8.46 Hz), 4.6–4.4 (m, 1H), 3.84 (s, 3H), 2.83–2.59 (m, 4H), 2.38 (dd, 1H, J=16.7 and 5 Hz), 1.71–1.57 (m, 7H), 0.96 (dd, 6H, J=9.92 and 6.3 Hz);

N-(2R-carboxymethyl-5-(biphen-4-yl)pentanoyl)-L-β-hydroxyvaline-N'-(phenyl)carboxamide: $^1$H NMR (300 MHz, CDCl$_3$) δ 8.73 (s, 1H), 8.07 (d, 1H, J=8.09 Hz), 7.52–7.25 (m, 11H), 7.10 (t, 1H, J=7.54 Hz), 6.97 (d, 2H, J=8.08 Hz), 4.41 (d, 1H, J=8.45 Hz), 3.02–3.00 (m, 1H), 2.75 (dd, 1H, J=16.55 and 8.45 Hz), 2.53–2.51 (m, 2H), 2.44 (dd, 1H, J=17.1 and 4.6 Hz), 1.85–1.47 (m, 4H), 1.45 (s, 3H), 1.21 (s, 3H); El. Anal. Calc. for $C_3H_3N_4O_4$: C, 71.69; H, 6.82; N, 5.57. Found: C, 71.65; H, 6.86; N, 5.53;

N-(2R-carboxymethyl-5-(biphen-4-yl)pentanoyl)-L-t-leucine-N'-(4-(methylsulfonyl)phenyl)carboxamide: $^1$H NMR (300 MHz, MeOH-d4) δ 8.10 (d, 1H, J=9 Hz), 7.84 (s, 4H), 7.47 (d, 2H, J=8 Hz), 7.25–7.40 (m, 5H), 7.13 (d, 2H, J=8 Hz), 4.48 (d, 1H, J=9 Hz), 2.95 (s, 3H), 2.44–2.70 (m, 4H), 2.36 (dd, 1H, J=16 and 5 Hz), 1.47–1.63 (m, 4H), 1.06 (s, 9H);

N-(2R-carboxymethyl-5-(4-(2-hydroxyethyl)phenyl)pentanoyl)-L-leucine-N'-(4-(methoxycarbonyl)phenyl)carboxamide: $^1$H NMR (300 MHz, MeOH-d4) δ 7.91 (d, 2H, J=9 Hz), 7.64 (d, 2H, J=9 Hz), 6.96 (s, 4H), 4.47–4.51 (m, 1H), 3.84 (s, 3H), 3.63 (t, 2H, J=7 Hz), 2.68 (t, 2H, J=7 Hz), 2.46–2.75 (m, 4H), 2.37 (dd, 1H, J=16 and 5 Hz), 1.51–1.73 (m, 7H), 0.93 and 0.89 (2d, 6H, J=7 Hz);

N-(2R-carboxymethyl-5-(4'-hydroxybiphen-4-yl)pentanoyl)-L-leucine-N'-(4-(methoxycarbonyl)phenyl)carboxamide: mp 195–197° C.; FAB-MS (M+H) expected: 575.2757; observed: 595.2750;

N-(2R-carboxymethyl-5-(4'-cyanobiphen-4-yl)pentanoyl)-L-leucine-N'-(4-(methoxycarbonyl)phenyl)carboxamide: $^1$H NMR (300 MHz, MeOH-d4) δ 10.02s, 1H), 8.37 (d, 1H, J=7 Hz), 7.87 (d, 2H, J=8 Hz), 7.71 (d, 2H, J=8.5 Hz), 7.64 (d, 4H, J=9 Hz), 7.35 (d, 2H, J=8 Hz), 7.16 (d, 2H, J=8 Hz), 4.50–4.53 (m, 1H), 3.81 (s, 3H), 2.49–2.78 (m, 4H), 2.35 (dd, 1H, J=16 and 5 Hz), 1.46–1.72 (m, 7H), 0.88 and 0.90 (2d, 2H, J=7 Hz);

N-(2R-carboxymethyl-5-(biphen-4-yl)pentanoyl)-L-leucine-N'-(4-(methoxycarbonyl)phenyl)carboxamide: mp 191–193° C.;

N-(2R-carboxymethyl-5-(4'-(2-aminoethoxy)biphen-4-yl)pentanoyl)-L-leucine-N'-(4-(methoxycarbonyl)phenyl)carboxamide: FAB-MS (M+H)$^+$ calc. 618.3179; found: 618.3189;

N-(2R-carboxymethyl-5-(4-(pyridin-4-yl)phenyl)pentanoyl)-L-cyclohexylglycine-N'-(4-((2-hydroxyethyl)aminosulfonyl)phenyl)carboxamide;

N-(2R-carboxymethyl-5-(biphen-4-yl)pentanoyl)-L-threonine-N'-(4S-(methylsulfinyl)phenyl)carboxamide;

N-(2R-carboxymethyl-5-(2-fluorobiphen-4-yl)pentanoyl)-L-leucine-N'-(4-(methoxycarbonyl)phenyl)carboxamide;

N-(2R-carboxymethyl-4-((biphen-4-yl)thio)butanoyl)-L-t-leucine-N'-(pyridin-4-yl)carboxamide;

N-(2R-carboxymethyl-5-(4-(2-aminopyridin-5-yl)phenyl)pentanoyl)-L-threonine-N'-(4S-(methylsulfinyl)phenyl)carboxamide;

N-(2R-carboxymethyl-5-(2-hydroxybiphen-4-yl)pentanoyl)-L-threonine-N'-(4S-(methylsulfinyl)phenyl)carboxamide;

N-(2R-carboxymethyl-5-(4'-cyanobiphen-4-yl)pentanoyl)-L-(trans-4-hydroxycyclohexyl)glycine-N'-(4S-(methylsulfinyl)phenyl)carboxamide;

N-(2R-carboxymethyl-5-(biphen-4-yl)pentanoyl)-L-(4-hydroxytetrahydropyran-4-yl)glycine-N'-(4S-(methylsulfinyl)phenyl)carboxamide; and N-(2R-carboxymethyl-5-(2R/S-hydroxy-3,3,3-trifluoropropyl)phenyl)pentanoyl)-L-(cyclohexyl)glycine-N'-(4S-(4-((2-hydroxyethyl)aminosulfonyl)phenyl)carboxamide.

Example 33

33A. Formula (II) Where $R^2$ is Biphenyl (and X is Propanyl), $R^3$ is t-Butyl, and $R^7$ is 4-Pyridine (in Place of the Illustrated Phenyl Group)

To a solution of 127.4 mg (0.200 mmol) of N-(2R-carboxymethyl-5-(biphen-4-yl)pentanoyl)-L-t-leucine-N'-(pyridin-4-yl)carboxamide and 40 μL of N-methyl morpholine in 1.0 mL of DMP at room temperature was added 115 mg (0.26 mmol) of benzotriazol-1-yl-tris-(dimethylamino) phosphonium hexafluorophosphate. After 15 min, 42 mg (0.60 mmol) of hydroxylamine hydrochloride was added in one portion, followed by addition of an additional 70 μL of N-methyl morpholine. The mixture was stirred for 24 h at room temperature, then partitoned between 30 mL of ethyl acetate and 25 mL of 0.5 M aq. sodium bicarbonate. The organic layer was washed with additional aq. sodium bicarbonate and with brine/pH 7 buffer, dried over sodium sulfate, and concentrated. Recrystallization from ethyl acetate provided 42.2 mg of N-(2R-(N-hydroxycarbamoyl)methyl-5-(biphen-4-yl)pentanoyl-L-t-leucine-N'-(pyrid-4-yl)carboxamide. Concentration of the filtrate and purification by radial chromatography (1 mm plate, 5% to 10% ethanol:dichloromethane) provided, after recrystallization from 2:1 ethyl acetate:hexane, an additional 21.0 mg of product. Total yield was 63.1 mg (61%) of N-(2R-(N-hydroxycarbamoyl)methyl-5-(biphen-4-yl)pentanoyl-L-t-leucine-N'-(pyrid-4-yl)carboxamide as a white powder: $^1$H NMR (300 MHz, DMSO-d6) δ 10.45 (s, 1H), 10.34 (s, 1H), 8.68 (8, 1H), 8.38 (d, 2H, J=7 Hz), 8.04 (d, 1H, J=9 Hz), 7.25–7.60 (m, 9H), 7.12 (d, 2H, J=7 Hz), 4.39 (d, 1H, J=9 Hz), 2.86–2.97 (m, 1H), 2.36–2.60 (m, 2H, obscured by DMSO-d5 resonance), 2.14 (dd, 1H, J=15 and 7 Hz), 2.02 (dd, 1H, J=15 and 8 Hz), 1.30–1.53 (m, 4H), 0.94 (s, 9H).

El. Anal. Calc. for $C_{30}H_{36}N_4O_4 \cdot 0.25H_2O$: C, 69.14; H, 7.06, N, 10.75. Found: C, 69.15; H, 7.23; N, 10.56.

33B. Formula (Ie) Varying $R^2$, $R^3$, and $R^7$

By following the procedure of part A and substituting N-(2R-carboxymethyl-5-(biphen-4-yl)pentanoyl)-L-t-leucine-N'-(pyridin-4-yl)carboxamide with the following:

N-(2R-(carboxymethyl-5-(biphen-4-yl)pentanoyl)-L-threonine-N'-(4S-(methylsulfinyl)phenyl)carboxamide;

N-(2R-(carboxymethyl-5-(4-(pyridin-4-yl)phenyl)pentanoyl)-L-(β-hydroxy)valine-N'-(4S-methylsulfinyl)phenylcarboxamide; and N-(2R-(carboxymethyl-4-methylpentanoyl)-L-t-leucine-N'-(pyridin-4-yl)carboxamide;

N-(2R-(carboxymethyl-(5-(4-(2S-hydroxypropyl)phenyl)pentanoyl)-L-(trans-4-hydroxycyclohexyl)glycine-N'-(pyridin-4-yl)carboxamide;

N-(2R-(carboxymethyl-5-(4-(2-methylthiazol-4yl)phenyl)pentanoyl)-L-(β-hydroxy)valine-N'-(pyridin-4yl)carboxamide; and N-(2R-(carboxymethyl-5-(4-(2R/S-hydroxy-3,3,3-trifluoropropyl)phenyl)pentanoyl)-L-(β-hydroxy)valine-N'-(pyridin-4-yl)carboxamide, there are obtained:

N-(2R-(N-hydroxycarbamoyl)methyl-5-(biphen-4-yl)pentanoyl)-L-threonine-N'-(4S-(methylsulfinyl)phenyl)carboxamide;

N-(2R-(N-hydroxycarbamoyl)methyl-5-(4-(pyridin-4-yl)phenyl)pentanoyl)-L-(β-hydroxy)valine-N'-(4S-methylsulfinyl)phenylcarboxamide;

N-(2R-(N-hydroxycarbamoyl)methyl-4-methylpentanoyl)-L-t-leucine-N'-(pyridin-4-yl)carboxamide;

N-(2R-(N-hydroxycarbamoyl)methyl-(5-(4-(2S-hydroxypropyl)phenyl)pentanoyl)L-(trans-4-hydroxycyclohexyl)glycine-N'-(pyridin-4-yl)carboxamide;

N-(2R-(N-hydroxycarbamoyl)methyl-5-(4-(2-methylthiazol-4-yl)phenyl)pentanoyl)-L-(β-hydroxy)valine-N'-(pyridin-4-yl)carboxamide;

N-(2R-(N-hydroxycarbamoyl)methyl-5-(4-(2R/S-hydroxy-3,3,3-trifluoropropyl)phenyl)pentanoyl)-L-(β-hydroxy)valine-N'(pyridin-4-yl)carboxamide.

N-(2R-(N-hydroxycarbamoyl)methyl-(5-(4-(2S-hydroxypropyl)phenyl)pentanoyl)-L-(trans-4-hydroxycyclohexyl)glycine-N'-(pyridin-4-yl)carboxamide;

N-(2R-(N-hydroxycarbamoyl)methyl-5-(4-(2-methylthiazol-4yl)phenyl)pentanoyl)-L-(β-hydroxy)valine-N'-(pyridin-4yl)carboxamide; and N-(2R-(N-hydroxycarbamoyl)methyl-5-(4-(2R/S-hydroxy-3,3,3-trifluoropropyl)phenyl)pentanoyl)-L-(β-hydroxy)valine-N'-(pyridin-4-yl)carboxamide.

Example 34

34A. Formula (C) Where $R^3$ is t-Butyl, and $R^4$ and $R^5$ are H

A solution of 2.00 g (6.32 mmol) of the N-hydroxysuccinimide ester of N-(t-butoxycarbonyl)-L-t-leucine in 9 mL of distilled aniline was stirred and heated at 100° C. for 30 min. The mixture was allowed to cool to room temperature, and diluted with 40 mL of ethyl acetate. The solution was washed with 4×50 mL of 1 N aq. sodium bisulfate, and the combined aqueous layers were extracted with 25 mL of ethyl acetate. The combined organic layers were washed with brine, dried over sodium sulfate, and concentrated. The residue was purified by chromatography on silica gel (2% to 10% ethyl acetate in dichloromethane) to give 1.36 g (74%) of N-(t-butoxycarbonyl)-L-t-leucine-N'-phenylcarboxamide as a white solid: $^1$H NMR (300 MHz, CDCl$_3$) δ 7.49 (d, 2H, J=8 Hz), 7.31 (t, 2H, J=8 Hz), 7.11 (t, 1H, J=7 Hz), 5.30–5.36 (m, 1H), 3.95 (d, 1H, J=9 Hz), 1.44 (8, 9H), 1.07 (s, 9H).

34B. Formula (C) Where $R^3$ is t-Butyl, $R^4$ is 4-Methylthio, and $R^5$ is H

In a manner analogous to that of part A was prepared N-(t-butoxycarbonyl)-L-t-leucine-N'-(4-(methylthio)phenyl)carboxamide: $^1$H NMR (300 MHz, CDCl$_3$) δ 7.65 (br s, 1H), 7.42 (d, 2H, J=8.5 Hz), 7.21 (d, 2H, J=8.5 Hz), 5.32 (br d, 1H), 3.95 (d, 1H, J=8.5 Hz), 2.45 (s, 3H), 1.44 (s, 9H), 1.06 (s, 9H).

El. Anal. Calc. for $C_{18}H_{23}N_2O_3S$: C, 61.33; H, 8.01, N, 7.95, S, 9.09. Found: C, 61.34; H, 8.06; N, 8.00, S, 9.18.

Example 35

Formula (C) Having A Trifluoroacetyl Protecting Group, Where $R^3$ is t-Butyl, and $R^4$ and $R^5$ are H To a solution of 1.36 g (4.4 mmol) of N-(t-butoxycarbonyl)-L-t-leucine-N'-phenylcarboxamide in 10 mL of dichloromethane was added 5 mL of tifluoroacetic acid. After 45 min at room temperature, the solution was diluted with toluene and concentrated. The residue was twice more concentrated from toluene to remove excess triflouroacetic acid, then dried under vacuum (ca. 1 mm Hg). The residue was then dissolved in 15 mL of dichloromethane and treated successively with pyridine (0.90 mL, 11 mmol) and trifluoroacetic anhydride (0.70 mL, 4.84 mmol). After 30 min, the mixture was partitioned between dichloromethane (25 mL) and 1 N aq. sodium bisulfate. The organic layer was washed with additional aq. sodium bisulfate, brine, dried over sodium sulfate, and concentrated to give 1.22 g (91%) of N-(trifluoroacetyl)-L-t-leucine-N'-phenylcarboxamide as a white solid: mp 201–203° C., $^1$H NMR (300 MHz, CDCl$_3$) δ 7.50 (d, 2H, J=8 Hz), 7.36 (t, 2H, J=8 Hz), 7.17 (t, 1H, J=7 Hz), 4.43 (d, 1H, J=9 Hz), 1.10 (s, 9H).

El. Anal. Calc. for $C_{14}H_{17}F_3N_2O_2$: C, 55.62; H, 5.67, N, 9.27. Found: C, 55.57; H, 5.60; N, 9.18.

Example 36

Formula (C) Having A Trifluoroacetyl Protecting Group, Where $R^3$ is t-Butyl, $R^4$ is 4-(2-Hydrozyethyl)aminosulfonyl, and $R^5$ is H To a solution of 250 mg (0.83 mmol) of N-(trifluoroacetyl)-L-t-leucine-N'-phenylcarboxamide in 5 mL of chloroform was added 0.4 mL (6 mmol) of chlorosulfonic acid. The mixture was heated to reflux for 35 min and then cooled to 0° C. and diluted with ethyl acetate. Ethanolamine (1.5 mL) was added and the mixture was stirred at 0° C. for 15 min. The mixture was partitioned between water and ethyl acetate, and the organic layer was washed with 1 N aq. sodium bisulfate, dried over sodium sulfate, and concentrated to provide 140 mg (40%) of N-(trifluoroacetyl)-L-t-leucine-N'-(4-((2-hydroxyethyl)aminosulfonyl)phenyl)carboxamide: $^1$H NMR (300 MHz, CDCl$_3$) δ 7.93 (s, 1H), 7.84 (d, 2H, J=9 Hz), 7.67 (d, 2H, J=9 Hz), 7.15 (br d, 1H), 4.90 (br t, 1H), 4.49 (d, 1H, J=9 Hz), 3.70 (t, 2H, J=5 Hz), 3.11 (q, 2H, J=5 Hz), 1.12 (s, 9H).

Example 37

Formula (D) Where $R^3$ is t-Butyl, $R^4$ is 4-(2-Hydrozyethyl)aminosulfonyl, and $R^5$ is H To a solution of 257 mg (0.6 mmol) of N-(trifluoroacetyl)-L-t-leucine-N'-(4-((2-hydroxyethyl)aminosulfonyl)phenyl)

carboxamide in 8 mL of ethanol was added 227 mg (6 mmol) of sodium borohydride. The mixture was heated to 55° C. for 15 min, allowed to cool to room temperature, and quenched with 10% ammonium hydroxide in methanol. After 20 h at room temperature, the mixture was filtered and the filtrate was absorbed onto silica gel. Chromatography (dichloromethane to 90:9:1 dichloromethane:methanol:ammonium hydroxide) gave 110 mg (56%) of L-t-leucine-N'-(4-((2-hydroxyethyl)aminosulfonyl)phenyl)carboxamide, as an oil: $^1$H NMR (300 MHz, CDCl$_3$) δ 9.48 (br s, 1H), 7.81 (d, 2H, J=9 Hz), 7.72 (d, 2H, J=9 Hz), 3.67 (t, 2H, J=5 Hz), 3.30 (s, 1H), 3.08 (q, 2H, J=5 Hz), 1.06 (s, 9H).

FAB-MS (M+H$^+$): expected 330.1488 observed 330.1480.

Example 38

Formula (Ib) Where R$^2$ is Biphenyl (X is propanyl), R$^3$ is t-Butyl, R$^4$ is 4R/S-Methylsulfinyl, and R$^5$ is H To a solution of 60.3 mg (0.100 mmol) of N-(2R-(t-butoxycarbonyl)methyl-5-(biphen-4-yl)pentanoyl)-L-t-leucine-N'-(4-(methylthio)phenyl)carboxamide in 2 mL of dichloromethane at −78° C. was added a solution of 26 mg (0.15 mmol) of m-chloroperbenzoic acid in 1 mL of dichloromethane. The reaction was stirred at −78° C. for 50 min, and then 0.2 mL of dimethyl sulfide was added. The mixture was allowed to warm to room temperature, and then partitioned between dichloromethane and sat. aq. sodium bicarbonate. The organic layer was washed with brine, dried over sodium sulfate, and concentrated to give 59.6 mg (96%) of N-(2R-(t-butoxycarbonyl)methyl-5-(biphen-4-yl)pentanoyl)-L-t-leucine-N'-(4R/S-(methylsulfinyl)phenyl) carboxamide, as a white solid: $^1$H NMR (300 MHz, CDCl$_3$) δ 8.46 (br s, 1H), 7.32–7.68 (m, 11H), 7.14 (d, 2H, J=8 Hz), 6.63 (d, 1H, J=9 Hz), 4.42 (d, 1H, J=9 Hz), 2.36–2.72 (m, 8H), 1.42–1.76 (s overlapping m, 13H), 1.09 (s, 9H).

Example 39

Formula (F")

To a solution of 2.779 g (7.50 mmol) of N-(2R-(t-butoxycarbonyl)methyl-4-pentenoyl)-4S-phenylmethyl-2-oxazolidinone in 30 mL of THF at 0° C. was added 2.55 mL (22.5 mol) of 30% aq. hydrogen peroxide, followed by the addition of 7.5 mL (15 mmol) of 2.0 N aq. lithium hydroxide. The mixture was stirred for 2 h at 0° C. and for 0.5 h at room temperature. After the mixture was recooled to 0° C., 15 mL of 2 M aq. sodium sulfite and 23 mL of sat. aq. sodium bicarbonate were added. The mixture was stirred an additional 30 min at 0° C., and then most of the THF was removed by concentration in vacuo. The residue was partitioned between CH$_2$Cl$_2$ and H$_2$O, and the aq. layer was extracted with additional CH$_2$Cl$_2$. The combined organic layers were extracted with aq. sodium bicarbonate, and then the combined aq. layers were acidified to pH 2 with sodium bisulfate. The resulting mixture was extracted twice with ethyl acetate, and the combined organic layers were washed with sat. aq. NaCl, diluted with 0.25 volume of hexane, dried over Na$_2$SO$_4$, and concentrated to provide 1.47 g (92%) of 2R-(t-Butoxycarbonyl)methyl-4-pentenoic acid as a colorless oil: $^1$H NMR (300 MHz, CDCl$_3$) δ 5.68–5.82 (m, 1H), 5.07–5.15 (m, 2H), 2.86–2.96 (m, 1H), 2.60 (dd, 1H, J=18 and 10 Hz), 2.25–2.52 (m, 3H), 1.43 (s, 9H).

Example 40

Formula (D'-1) Where R$^3$ is t-Butyl and R$^7$ is 4-(Methoxycarbonyl)phenyl

In a manner analogous to Example 31, substituting 2R-(t-butoxycarbonyl)methyl-(5-(biphen-4-yl)pentanoic acid with 2R-(t-Butoxycarbonyl)methyl-4-pentenoic acid, and substituting L-t-leucine-N'-(4-(pyrid-4-yl)carboxamide with L-leucine-N'-(4-(methoxycarbonyl)phenyl)-carboxamide, there was prepared N-(2R-(t-butoxycarbonyl)methyl-4-pentenoyl)-L-leucine-N'-(4-(methoxycarbonyl)-phenyl) carboxamide: mp 118–119° C. (cyclohexane); $^1$H NMR (300 MHz, CDCl$_3$) δ 8.96 (s, 1H), 7.95 (d, 2H, J=9 Hz), 7.57 (d, 2H, J=9 Hz), 6.32 (d, 1H, J=7 Hz), 5.63–5.77 (m, 1H), 4.95–5.08 (m, 2H), 4.52–4.60 (m, 1H), 3.88(s, 3H), 2.36–2.77 (m, 4H), 2.14–2.27 (m, 1H), 1.60–1.87 (m, 3H), 1.45 (s, 9H), 0.97 (d, 3H, J=7 Hz), 0.91 (d, 3H, J=7 Hz).

El. Anal. Calc. for CH$_{25}$H$_{36}$N$_2$O$_6$: C, 65.20; H, 7.88, N, 6.08. Found: C, 65.04; H, 7.80; N, 6.06.

Example 41

41A. Formula (D'-2) Where R$^2$ is Fluoren-2-yl (X is Propanyl), R$^3$ is t-Butyl, and R$^7$ is 4-(Methoxycarbonyl) phenyl To a solution of 167 mg (0.36 mmol) of N-(2R-(t-butoxycarbonyl)methyl-4-pentenoyl)-L-leucine-N'-(4-(methoxycarbonyl)phenyl)carboxamide, 108 mg (0.44 mmol) of 2-bromofluorene, 21 mg (0.07 mmol) of tri-o-tolylphosphine, and 69 μL (50 mg, 0.50 mmol) of triethylamine in 1.0 mL of DMF under argon was added 8.0 mg (0.035 mmol) of palladium diacetate. The solution was heated at 100° C. for 2 h, cooled to room temperature, and then partitioned between 3:1 ethyl acetate:hexane and water. The organic layer was washed with 1N aq. sodium bisulfate and with brine/pH 7 buffer, dried over sodium sulfate, and concentrated. Purification by flash chromatography (20 g silica, 5% to 10% t-butyl methyl ether in dichloromethane) gave 185 mg (82%) of the product as a solid containing trace impurities by TLC. Recrystallization from t-butyl methyl ether/isooctane provided 115 mg (51%) of N-(2R-(t-butoxycarbonyl)methyl-5-(fluoren-2-yl)-4E-pentenoyl)-L-leucine-N'-(4-(methoxycarbonyl)phenyl)carboxamide as fine white needles: mp 189–192° C.; $^1$H NMR (300 MHz, CDCl$_3$) δ 8.32 (s, 1H), 7.79 (d, 2H, J=8 Hz), 7.72 (d, 1H, J=8 Hz), 7.57 (d, 1H, J=8 Hz), 7.45–7.53 (m, 3H), 7.36 (t, 1H, J=7.5 Hz), 7.25–7.32 (m, 2H), 7.17 (d, 1H, J=7 Hz), 4.52–4.60 (m, 1H), 3.75 (s, 5H), 2.33–2.87 (m, 5H), 1.60–1.90 (m, 3H), 1.45 (s, 9H), 0.92 (apparent t, 6H).

El. Anal. Calc. for C$_{38}$H$_{44}$N$_2$O$_6$.0.5H$_2$O: C, 72.01; H, 7.16, N, 4.42. Found: C, 71.87; H, 7.07; N, 4.32.

41B. Formula (D'-2) Where R$^2$ is 7-(N-(Benzyloxycarbonyl) glycyl)aminofluoren-2-yl (X is Propanyl), R$^3$ is t-Butyl, and R$^7$ is 4-(Methozycarbonyl)phenyl To a solution of 600 mg (2.31 mmol) of 2-amino-7-bromofluorene and 483 mg (2.31 mmol) of N-(benzyloxycarbonyl)glycine in 10 mL of anhydrous pyridine was added 442 mg (2.31 mmol) of EDC hydrochloride. The reaction was heated at 60° C. for 4 days, and then the solution was concentrated. The residue was partitioned between ethyl acetate and 1 N aq. hydrochloric acid, and the organic layer was washed with sat. aq. sodium bicarbonate and with brine, dried over magnesium sulfate, and concentrated to give 813 mg (78%) of N-(benzyloxycarbonyl) glycine-N'-(7-bromofluoren-2-yl)carboxamide as a tan solid: mp 194–195° C.

By following the procedure of part A and substituting 2-bromofluorene with N-(benzyloxycarbonyl)glycine-N'-(7-bromofluoren-2-yl)carboxamide, there is obtained N-(2R-(t-butoxycarbonyl)methyl-5-(7-(N-(benzyloxycarbonyl) glycyl)aminofluoren-2-yl)-4E-pentenoyl)-L-leucine-N'-(4-(methoxycarbonyl)phenyl)carboxamide: mp 213–214° C. FAB-MS (M+Cs)$^+$ calculated for C$_{48}$H$_{54}$N$_4$O$_9$.Cs: 963.2945; observed: 963.2960. El. Anal. Calc. for $C_{47}H_{54}N_4O_9$: C, 69.40; H, 6.51, N, 6.75. Found: C, 69.47; H, 6.51; N, 6.70.

41C. Formula (D'-2) Where $R^2$ is 4-(Pyrid-4-yl)phenyl (X in Propanyl), $R^3$ is t-Butyl, and $R^7$ is 4-(Methozycarbonyl) phenyl Aq. 2 M sodium carbonate (3 mL)was added to a suspension of 400 mg (2.0 mmol) of 4-bromopyridine in 2 mL of benzene to give 2 clear phases, and argon was bubbled through the mixture for a few minutes before added 115 mg (0.10 mmol) of palladium tetrakis(triphenylphosphine). To the resulting mixture was added a solution of 200 mg (1.00 mmol) of 4-bromophenylboronic acid in 1 mL of ethanol, and the mixture was heated at reflux for 4 h. After cooling to room temperature, the mixture was partitioned between ethyl acetate (25 ml) and water (25 mL). The organic layer was dried over sodium sulfate and concentrated. Purification of the residue by silica gel chromatography, eluting with 25% to 50% ethyl acetate in hexane, gave 193 mg (82%) of 4-(4-bromophenyl)pyridine as a white solid: mp 124–126° C.

By following the procedure of part A and substituting 2-bromofluorene with 4-(4-bromophenyl)pyridine, there is obtained N-(2R-(t-butoxycarbonyl)methyl-5-(4-(pyrid-4-yl) phenyl)-4E-pentenoyl)-L-leucine-N'-(4-(methoxycarbonyl) phenyl)carboxamide: $^1$H NMR (300 MHz, CDCl$_3$) δ 8.80 (s, 1H), 8.64 (d, 2H, J=6 Hz), 7.85 (d, 2H, J=8.5 Hz), 7.49 (d, 2H, J=9 Hz), 7.45 (d, 2H, J=6 Hz), 7.19 (d, 2H, J=8 Hz), 6.40 (d, 1H, J=16 Hz), 6.33 (d, 1H, J=8 Hz), 6.09–6.17 (m, 1H), 4.54–4.57 (m, 1H), 3.80 (s, 3H), 2.38–2.81 (m, 5H), 1.48–1.84 (m, 3H), 1.44 (s, 9H), 0.90 and 0.94 (2 d, 6H, J=7 Hz).

Example 42

42A. Formula (Ib') Where $R^2$ is Fluoren-2-yl (X is Propanyl), $R^3$ is t-Butyl, and $R^7$ is 4-(Methoxycarbonyl) phenyl A solution of 111 mg (0.177 mmol) of N-(2R-(t-butoxycarbonyl)methyl-5-(fluoren-2-yl)-4-pentenoyl)-L-leucine-N'-(4-(methoxycarbonyl)phenyl)carboxamide in 7 mL of 4:3 ethyl acetate:ethanol was hydrogenated at 1 atm hydrogen pressure over 30 mg of 10% palladium on carbon for 3 h. The catalyst was removed by filtration through Celite, and the filtrate was concentrated. Trituration with t-butyl methyl ether gave 110 mg (99%) of N-(2R-(t-butoxycarbonyl)methyl-5-(fluoren-2-yl)pentanoyl)-L-leucine-N'-(4-(methoxycarbonyl)phenyl)carboxamide as a white solid: mp 166–167° C. (softening at 161° C.).

El. Anal. Calc. for $C_{37}H_{46}N_2O_6$: C, 72.29; H, 7.54, N, 4.56. Found: C, 72.32; H, 7.54; N, 4.62.

42B. Formula (Ib') Varying $R^2$

By following the procedure of part A and substituting N-(2R-(t-butoxycarbonyl)methyl-5-(fluoren-2-yl)-4-pentenoyl)-L-leucine-N'-(4-(methoxycarbonyl)phenyl) carboxamide with:

N-(2R-(t-butoxycarbonyl)methyl-5-(7-(N-(benzyloxy-carbonyl)glycyl)aminofluoren-2-yl)-4E-pentenoyl)-L-leucine-N'-(4-(methoxycarbonyl)phenyl)carboxamide; and N-(2R-(t-butoxy-carbonyl)methyl-5-(4-(pyrid-4-yl) phenyl)-4E-pentenoyl)-L-leucine-N'-(4-(methoxy-carbonyl)phenyl)carboxamide, there are obtained:

N-(2R-(t-butoxycarbonyl)methyl-5-(7-(glycyl) aminofluoren-2-yl)pentanoyl)-L-leucine-N'-(4-(methoxycarbonyl)phenyl)carboxamide FAB-MS (M+H)$^+$ calculated for $C_{40}H_{51}N_4O_7$: 699.3758; observed: 699.3770; and N-(2R-(t-butoxycarbonyl)methyl-5-(4-(pyrid-4-yl) phenyl)pentanoyl)-L-leucine-N'-(4-(methoxycar-bonyl)phenyl)carboxamide: mp 174–176° C.; $^1$H NMR (300 MHz, CDCl$_3$) δ 8.85 (s, 1H), 8.63 (d, 2H, J=5 Hz), 7.95 (d, 2H, J=8 Hz), 7.57 (d, 2H, J=9 Hz), 7.41–7.47 (m, 4H), 7.07 (d, 2H, J=8 Hz), 6.19 (d, 1H, J=7 Hz), 4.53–4.56 (m, 1H), 3.85 (s, 3H), 2.37–2.66 (m, 5H), 1.45–1.83 (m, 7H), 1.42 (s, 9H), 0.91 and 0.95 (2 d, 6H, J=7 Hz).

Example 43

Formula (C-1) Where $R^4$ and $R^5$ are H

To a stirred suspension of 4.18 g (20.0 mmol) of N-(benzyloxycarbonyl)glycine, 2.73 mL (2.79 g, 30 mmol) of aniline, and 110 mg (1.0 mmol) of 4-dimethylaminopyridine in 55 mL of dichlormethane at 0° C. was added 6.53 g (22 mmol) of EDC methiodide in one portion. The mixture was stirred for 18 h at room temperature, and then partitoned between 200 mL of 3:1 ethyl acetate:hexane and water. The organic layer was washed with 1 N aq. sodium bisulfate, sat. aq. sodium bicarbonate, and finally with brine/pH 7 phosphate buffer, dried over sodium sulfate, and concentrated. Recrystallization from 1:1 ethyl acetate:isooctane gave 3.69 g (65%) of N-(benzyloxycarbonyl)glycine-N'-phenylcarboxamide: mp 143–144° C.

Example 44

Formula (C-2) Where $R^4$ and $R^5$ are H

To a stirred solution of 1.42 g (5.00 mmol) of N-(benzyloxycarbonyl)glycine-N'-phenylcarboxamide in 35 mL of dry THF at −5° C. was added by syringe 6.15 mL (16.0 mmol) of 2.6 M n-butyllithium in hexane at a rate to maintain the reaction temperature below 10° C. After ca. ⅔ of the n-butyllithium had been added, a yellow color began to persist, and the addition was stopped for ca. 10 min and then resumed in a dropwise fashion so as to maintain the reaction temperature at about 0° C. After the addition was complete, the orange solution was stirred at 0° C. for 45 min, and then cooled to −70° C. Acetone (1.10 mL, 15 mmol) was added in one portion by syringe. After 10 min, the reaction was partitioned between 1 M pH 7 phosphate buffer and 3:1 ethyl acetate:hexane. The organic layer was washed with brine, dried over sodium sulfate, and concentrated. The residue was purified by chromatography on 75 g of silica, eluting with 40% ethyl acetate:hexane. First to elute was pure products fractions (pool #1), followed by fractions containing product and the starting glycinanilide (pool #2). The residue from pool #2 was recrystallized from ethyl acetate:isooctane to give nearly pure starting material as a solid, and mother liquors containing mostly product. The residue from the concentration of the mother liquors was purified by radial chromatography (4 mm plate, 30% ethyl acetate:hexane), and the product fractions were combined with pool #1% to give, after trituration of the gummy residue with hexane/t-butyl methyl ether, 423 mg (25%) of N-(benzyloxycarbonyl)-DL-β-hydroxyvaline-N'-(phenyl) carboxamide as a pale yellow solid: mp 128–129° C.; $^1$H NMR (300 MHz, CDCl$_3$) δ 8.30 (br s, 1H), 7.39 (d, 2H, J=8 Hz), 7.18–7.28 (m, 7H), 7.06 (t, 1H, J=7 Hz), 5.83 (br d, 1H), 5.05 (s, 2H), 4.04 (d, 1H, J=9 Hz), 3.73 (s, 1H), 1.33 (s, 3H), 1.16 (s, 3H).

El. Anal. Calc. for $C_{19}H_{22}N_2O_4$: C, 66.65; H, 6.48, N, 8.18. Found: C, 66.66; H, 6.57; N, 8.14.

Example 45

Formula (C-2) Where $R^4$ and $R^5$ are H

A solution of 400 mg (1.17 mmol) of N-(benzyl-oxycarbonyl)-DL-β-hydroxyvaline-N'-phenylcarboxamide in 10 mL of ethyl acetate was hydrogenated over 50 mg of 10% palladium on carbon at 1 atm of hydrogen pressure for 1.5 h. The catalyst was removed by furation through Celite, and the filtrate was concentrated to give 259 mg (>100%) of DL-β-hydroxyvaline-N'-(phenyl)carboxamide, which was used without further purification: mp 97–99° C.

El. Anal. Calc. for $C_{11}H_{16}N_2O_2$: C, 63.44; H, 7.74, N, 13.45. Found: C, 63.52; H, 7.79; N, 13.40.

Example 46

Formula (Ib) Where $R^2$ is Biphenyl, $R^3$ is Hydroxy-t-butyl, and $R^4$ and $R^5$ are H To a solution of 203 mg (0.55 mmol) of 2R-(t-butoxycarbonyl)methyl-(5-(biphen-4-yl)pentanoic acid, 104 mg (0.50 mmol) of DL-β-hydroxyvaline-N'-(phenyl) carboxamide, and 90 μL (0.65 mmol) of triethylamine in 2.5 mL of DMF was added 265 mg (0.60 mmol) of benzotriazol-1-yl-tris-(dimethylamino)-phosphonium hexafluorophosphate. After 24 h, the reaction was partitioned between 3:1 ethyl acetate:hexane and ca. 0.2 N aq. sodium bicarbonate. The organic layer was washed with 1N ag. sodium bisulfate and with brine/pH 7 buffer, dried over sodium sulfate, and concentrated. The residue was purified by radial chromatography (4 mm plate), eluting with 25% to 30% ethyl acetate in hexane. First to elute was 121 mg (43%) of N-(2R-(t-butoxycarbonyl)methyl-5-(biphen-4-yl) pentanoyl)-D-β-hydroxyvaline-N'-(phenyl)carboxamide (diastereomer), followed by 140 mg (50%) of N-(2R-(t-butoxycarbonyl)methyl-5-(biphen-4-yl)pentanoyl)-L-β-hydroxyvaline-N'-(phenyl)carboxamide as a gummy semi-solid containing, according to NMR analysis, about 1 mole-equivalent of isooctane (the solvent from which the final sample was concentrated): $^1$H NMR (300 MHz, CDCl$_3$) δ 8.77 (s, 1H), 7.24–7.56 (m, 11H), 7.03–7.14 (m, 3H), 6.89 (d, 1H, J=8.5 Hz), 4.46 (d, 1H, J=8.5 Hz), 4.17 (s, 1H), 2.52–2.70 (m, 4H), 2.36 (br d, 1H, J=12.5 Hz), 1.50–1.70 (m, 4H), 1.43 (s, 3H), 1.40 (s, 9H), 1.25 (s, 3H).

Example 47

Formula (P-1)

To a solution of 510 mg (1.97 mmol) of N-(4-pentenoyl)-4S-phenylmethyl-2-oxazolidinone in 8 mL of dichloromethane at 0° C. was added 2.2 mL (2.2 mmol) of 1 M titanium tetrachloride in dichloromethane. After 15 min, 0.42 mL (2.4 mmol) of diisopropylethylamine was added to the thick slurry to give a deep red solution. After 1 h at 0° C., 216 mg (2.4 mmol) of s-trioxane in 2 mL of dichloromethane was added via cannula, followed by an additional 2.2 mL of 1M titanium tetrachloride in dichloromethane. After 4 h at 0° C., the solution was partitioned between aq. ammonium chloride and dichloromethane. The organic layer washed with 1 N aq. HCl, with brine containing pH 7 phosphate buffer, dried over sodium sulfate, and concentrated. The residue was purified by chromatography on 20 g silica, eluting with 30% to 40% ethyl acetate in hexane. Recrystallization of the purified product from t-butyl methyl ether/isooctane provided 404 mg (71%) of N-(2R-hydroxymethyl-4-pentenoyl)-4S-phenylmethyl-2-oxazolidinone: mp 71–72° C.; $^1$H NMR (300 MHz, CDCl$_3$) δ 7.22–7.37 (m, 5H), 5.78 (dddd, J=10, 7, 4, and 3 Hz), 5.03–5.15 (m, 2H), 4.69 (dddd, 1H, J=10, 6, 4, and 3 Hz), 4.17–4.24 (m, 2H), 4.02–4.10 (m, 1H), 3.85–3.91 (m, 2H), 3.29 (dd, 1H, J=4 and 3 Hz), 2.82 (dd, 1H, J=14 and 10 Hz), 2.44 (dt, 1H, J=14 and 7 Hz), 2.31 (dd, 1H, J=14 and 7 Hz), 2.17 (br s, 1H).

Example 48

Formula (P-2)

To a suspension of 4.0 g (25.1 mmol) of O-benzylhydroxylamine hydrochloride in 50 mL of THF at 0° C. under argon was added 11.4 mL (22.8 mmol) of 2M trimethylaluminum in toluene. After the addition was complete, the solution was allowed to warm to room temperature. After 15 min, this solution was added via cannula to a solution of 2.40 g (8.30 mmol) of N-(2R-hydroxymethyl-4-pentenoyl)-4S-phenylmethyl-2-oxazolidinone in 100 mL of THF at 0° C. under argon. The reaction was stirred for 6 h at 0° C., and then partitioned between 1N HCl/brine and ethyl acetate/diethyl ether. The organic layer was with 1M pH 7 phosphate buffer and with brine, dried over sodium sulfate, and concentrated. The residue was purified by chromatography on silica, eluting with 35% to 45% ethyl acetate in hexane, to give, after elution of 4S-phenylmethyl-2-oxazolidinone, 2.01 g of the product. Recrystallization from ethyl acetate: isooctane provided 1.90 g (97%) of N-benzyloxy-2R-hydroxymethyl-4-pentenamide as a white powder: mp 58–59° C.; $^1$H NMR (300 MHz, CDCl$_3$) δ 8.40 (s, 1H), 7.38 (m, 5H), 5.71 (m, 1H), 5.03–5.06 (m, 1H), 4.91 (dd, 1H, J=16 and 12 Hz), 3.73 (m, 1H), 2.20 (m, 2H).

El. Anal. Calc. for $C_{13}H_{17}NO_3$: C, 66.36; H, 7.28, N, 5.95. Found: C, 66.15; H, 7.32; N, 5.99.

Example 49

Formula (P-3)

To a solution of 1.92 g (8.17 mmol) of N-benzyloxy-2R-hydroxymethyl-4-pentenamide in 10 mL of anhydrous pyridine at 0° C. was added 1.24 mL (16.3 mmol) of mesyl chloride. After 3 h, the reaction was poured onto ice, and the mixture was partitioned between ethyl acetate and 1 N aq. sodium bisulfate. The organic layer was washed with additional sodium bisulfate, and the combined aqueous layers were extracted with ethyl acetate. The combined organic layers were dried over sodium sulfate and concentrated. The residual oil was dissolved in 30 mL of acetone and 3.38 g of powdered potassium carbonate was added. The mixture was heated at reflux for 3 h and then cooled to room temperature. The precipitate was removed by filtration through Celite, and the filter cake was washed well with ethyl acetate. The filtrate was concentrated, and the due was purified by chromatography on silica, eluting with 25% ethyl acetate in hexane, to provide 1.64 g (93%) of N-benzyloxy-3R-(2-propen-1-yl)-2-azetidinone as a slightly orange oil: $^1$H NMR (300 MHz, CDCl$_3$) δ 7.37–7.42 (m, 5H), 5.65–5.75 (m, 1H), 5.00–5.06 (m, 1H), 4.93 (s, 2H), 3.32 (ddd, 1H, J=5, 4, and 2 Hz), 2.95 (m, 2H), 2.40–2.47 (m, 1H), 2.20–2.28 (m, 1H).

El. Anal. Calc. for $C_{13}H_{15}NO_2$: C, 71.86; H, 6.96, N, 6.45. Found: C, 71.59; H, 6.88; N, 6.37.

Example 50

Formula (P-4) Where $R^2$ is Biphenyl

A solution of 434 mg (2.00 mmol) of N-benzyloxy-3R-(2-propen-1-yl)-2-azetidinone, 583 mg (2.5 mmol) of 4-bromobiphenyl, 0.34 mL (2.5 mmol) of triethylamine, 35 mg (0.11 mmol) of tri(o-tolyl)phosphine, and 14 mg (0.06 mmol) of palladium diacetate in 7 mL of DMF was heated at 100° C. for 18 h. The reaction solution was cooled to room temperature and partitioned between ethyl acetate and water. The organic layer was washed with water, dried over sodium sulfate, and concentrated. The residue was chromatographed on silica, eluting with 25% ethyl acetate in hexane, to give slightly impure product, which was recrystallized from ethyl acetate/isooctane to give 315 mg (43%) of N-benzyloxy-3R-(3-(biphen-4-yl)-2-propen-1-yl)-2-azetidinone as small white flakes: mp 109–110° C.; $^1$H NMR (300 MHz, CDCl$_3$) δ 7.31–7.61 (m, 14H), 6.43 (d, 1H, J=15 Hz), 6.18 (ddd, 1H, J=15, 9, and 7 Hz), 4.94 (s, 2H), 3.36 (dd, 1H, J=10 and 5 Hz), 3.00–3.04 (m, 2H), 2.60–2.75 (m, 1H), 2.20–2.50 (m, 1H).

El. Anal. Calc. for $C_{25}H_{23}NO_2$: C, 81.27; H, 6.28, N, 3.79. Found: C, 81.09; H, 6.31; N, 3.71.

Example 51

Formula (P-5) Where $R^2$ in Biphenyl

To a stirred solution of 62.0 mg (0.168 mmol) of N-benzyloxy-3R-(3-(biphen-4-yl)-2-propen-1-yl)-2-azetidinone in 5 mL of 4:1 THF:ethanol was added 2 mL of 1N aq. lithium hydroxide. The mixture was stirred vigorously for 1 h at room temperature, and the diluted with 10 mL of 0.5 M pH 4 citrate buffer. The mixture was partitoned between 20 mL of t-butyl methyl ether and brine, and the organic layer was dried, after dilution with ca. 5 mL hexane, over sodium sulfate, and concentrated to a residual glass. This residue was immediately dissolved in 5 mL of dichloromethane, cooled to 0° C., and 0.10 mL of pyridine was added, followed by 1.2 mL of a solution of formic anhydride in dichloromethane, which was prepared by allowing 297 mg (1.00 mmol) of EDC methiodide and 80 μL (2.00 mmol) of formic acid in. 5 mL of dichloromethane to react at 0° C. for 15 min. After 30 min, the reaction was partitioned between dichloromethane and 0.5 M citrate buffer. The organic layer was dried over sodium sulfate and concentrated. Chromatography of the residue on 5 g of silica, eluting with a gradient of 5% to 10% ethanol in dichloromethane, gave 58 mg (83%) of N-((N"-formyl-N"-benzyloxyamino)methyl-5-(biphen-4-yl)-4-pentenoic acid as a glass. $^1$H NMR spectrum at room temperature in CDCl$_3$ showed broad peaks of amide rotamers.

Example 52

Formula (P-6) Where $R^2$ in Biphenyl, $R^3$ is t-Butyl, $R^7$ is 4-Pyridinyl and p is Zero To a solution of 99.6 mg (0.24 mmol) of N-((N"-formyl-N"-benzyloxyamino)methyl-5-(biphen-4-yl)pentanoic acid, 125 mg (0.288 mmol) of L-t-leucine-N'-(pyridin-4-yl) carboxamide bis(trifluroacetate), and 0.125 mL (0.90 mmol) of triethylamine in 4 mL of DMF was added 133 mg (0.30 mmol) of benzotriazol-1-yl-tris-(dimethylamino) phosphonium hexafluorophosphate. After 16 h at room temperature, the reaction was partitioned between ethyl acetate and ca. 0.5 M aq. sodium bicarbonate. The organic layer was washed with 1 M pH 7 phosphate buffer and with brine, dried over sodium sulfate, and concentrated. Purification of the residue by chromatography, eluting with 40% to 75% ethyl acetate in hexane, followed by recrystallization from ethyl acetate/isooctane gave 97.4 mg (67%) of N-((N"-formyl-N"-benzyloxyamino)methyl-5-(biphen-4-yl)-4-pentenoyl)-L-t-leucine-N'-(pyridin-4-yl)carboxamide: mp: 215–216° C.

Example 53

53A. Formula (Ih) Where $R^2$ is Biphenyl, $R^3$ is t-Butyl, $R^7$ is 4-Pyridinyl and p is Zero A solution of 87.1 mg (0.143 mmol) of N-((N"-formyl-N"-benzyloxyamino)methyl-5-(biphen-4-yl)pentanoyl)-L-t-leucine-N'-(pyridin-4-yl)carboxamide in 5 mL of 3:2 ethyl acetate:ethanol was hydrogenated over 25 mg of 10% palladium on carbon at 1 atm of hydrogen pressure for 6 h. The catalyst was removed by filtration through Celite, and the filtrate was concentrated. Recrystallation of the residue from ethyl acetate gave 59.0 mg (80%) of N-((N"-formyl-N"-hydroxyamino)methyl-5-(biphen-4-yl)pentanoyl)-L-t-leucine-N'-(pyridin-4-yl)carboxamide as a white powder: mp 190–191° C.; $^1$H NMR (300 MHz, DMSO-d$_6$) δ 10.52 (br s, 1H), 9.97 (br s, 1H, 9.53 (br s, 1H), 8.38 (d, 2H, J=7 Hz), 7.20 (br s, 1H), 7.14 (br d, 1H, J=8 Hz), 7.23–7.60 (m, 9H), 7.12 (d, 2H, J=7 Hz), 4.41 (d, 1H, J=9 Hz), 3.40–3.62 (m, 2H), 2.90–3.10 (m, 1H), 2.4–2.6 (m, 2H, partially obscured by DMSO-d5 resonance), 1.28–1.52 (m, 4H), 0.94 (s, 9H).

El. Anal. Calc.: for $C_{30}H_{36}N_4O_4 \cdot 0.5H_2O$: C, 68.55; H, 7.10, N, 10.66. Found: C, 68.48; H, 7.04; N, 10.63.

53B. Formula (Ih) Varying $R^2$, $R^3$, and $R^7$

By following procedures analogous to Examples 50–52 there are obtained the following compounds of formula (P-6):

N-(2R-(N"-formyl-N"-benzyloxyamino)methyl-5-(4-(2RS-hydroxy-3,3,3-trifluoropropyl)phenyl)-4-pentenoyl)-L-t-leucine-N'-(pyridin-4-yl)carboxamide;

N-(2R-(N"-formyl-N"-benzyloxyamino)methyl-5-(4-(imidaz-4-yl)phenyl)-4-pentenoyl)-L-threonine-N'-((4S-methylsulfinyl)phenyl)carboxamide;

N-(2R-(N"-formyl-N"-benzyloxyamino)methyl-5-(4-(2RS-hydroxy-3,3,3-trifluoropropyl)phenyl)-4-pentenoyl)-L-t-leucine-N'-(pyridin-4-yl)carboxamide;

N-(2R-(N"-formyl-N"-benzyloxyamino)methyl-5-(4-(imidaz-4-yl)phenyl)-4-pentenoyl)-L-threonine-N'-((4S-methylsulfinyl)phenyl)carboxamide;

N-(2R-(N"-formyl-N"-benzyloxyamino)methyl-5-(4-(pyridin-4-yl)phenyl)-4-pentenoyl)-L-t-leucine-N'-(4-((2-hydroxyethyl)aminosulfonyl)phenyl)carboxamide;

N-(2R-(N"-formyl-N"-benzyloxyamino)methyl-5-(4-(pyridin-4-yl)phenyl)-4-pentenoyl)-L-(β-hydroxy) valine-N'-(4S-methylsulfinyl)phenyl)carboxamide;

N-(2R,S-(N"-formyl-N"-benzyloxyamino)methyl-(4-(methyl)-4-pentenoyl)-L-leucine-N'-(4-(methoxycarbonyl)phenyl)carboxamide; and N-(2R-(N"-formyl-N"-benzyloxyamino)methyl-5-(biphen-4-yl)pentanoyl)-L-cyclohexylglycine-N'-(4-((2-(dimethylamino)ethyl)aminosulfonyl)phenyl) carboxamide, which, when substituted for N-((N"-formyl-N"-benzyloxyamino)methyl-5-(biphen-4-yl)pentanoyl)-L-t-leucine-N'-(pyridin-4-yl)carboxamide in the procedure of Example 53A, give the following respective compounds:

N-(2R-(N"-formyl-N"-hydroxyamino)methyl-5-(4-(2RS-hydroxy-3,3,3-trifluoropropyl)phenyl) pentanoyl)-L-t-leucine-N'-(pyridin-4-yl) carboxamide;

N-(2R-(N"-formyl-N"-hydroxyamino)methyl-5-(4-(imidaz-4-yl)phenyl)pentanoyl)-L-threonine-N'-(((4S-methylsulfinyl)phenyl)carboxamide;

N-(2R-(N"-formyl-N"-hydroxyamino)methyl-5-(4-(pyridin-4-yl)phenyl)pentanoyl)-L-t-leucine-N'-(4-

((2-hydroxyethyl)aminosulfonyl)phenyl)
carboxamide;
N-(2R-(N"-formyl-N"-hydroxyamino)methyl-5-(4-(pyridin-4-yl)phenyl)pentanoyl)-L-(β-hydroxy)valine-N'-(4S-methylsulfinyl)phenyl)carboxamide;
N-(2R,S-(N"-formyl-N"-hydroxyamino)methyl-(4-(methyl)pentanoyl)-L-leucine-N'-(4-(methoxycarbonyl)phenyl)carboxamide: MS (M−H)⁻: 434.2 (M−CO, H₂O): 388; and
N-(2R-(N"-formyl-N"-hydroxyamino)methyl-5-(biphen-4-yl)pentanoyl)-L-cyclohexylglycine-N'-(4-((2-(dimethylamino)ethyl)aminosulfonyl)phenyl)carboxamide.

Examples 54–59

These examples illustrate the preparation of a representative pharmaceutical formulation containing an active compound of formula (I), e.g., N-(2R-carboxymethyl-5-(biphen-4-yl)pentanoyl)-L-β-hydroxyvaline-N'-(phenyl)carboxamide, or a pharmaceutically acceptable salt thereof. Other compounds of formula (I) can be used as the active compound in, preparation of the formulations of these examples.

Example 54

This example illustrates the preparation of representative pharmaceutical formulations for oral administration.

| A. | Ingredients | % wt./wt. |
|---|---|---|
| | Compound of formula (I) | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of formula (I) | 20.0% |
| | Magnesium stearate | 0.9% |
| | Starch | 8.6% |
| | Lactose | 79.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of formula (I) | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of formula (I) is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of formula (I) | 20.0% |
| | Peanut Oil | 78.0% |
| | Span 60 | 2.0% |

The above ingredients are melted, mixed and filled into soft elastic capsules.

Example 55

This example illustrates the preparation of a representative pharmaceutical formulation for parenteral administration.

| Ingredients | |
|---|---|
| Compound of formula (I) | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of formula (I) is dissolved in propylene glycol, polyethylene glycol 400 and polysorbate 80. A sufficient quantity of 0.9% saline solution is then added with stirring to provide 100 mL of the I.V. solution which is filtered through a 0.2μ membrane filter and packaged under sterile conditions.

Example 56

This example illustrates the preparation of a representative pharmaceutical composition in suppository form.

| Ingredients | % wt./wt. |
|---|---|
| Compound of formula (I) | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 57

This example illustrates the preparation of a representative pharmaceutical formulation for insufflation.

| Ingredients | % wt./wt. |
|---|---|
| Micronized compound of formula (I) | 1.0% |
| Micronized lactose | 99.0% |

The ingredients are milled, mixed, and packaged in an insufflator equipped with a dosing pump.

Example 58

This example illustrates the preparation of a representative pharmaceutical formulation in nebulized form.

| Ingredients | % wt./wt. |
| --- | --- |
| Compound of formula (I) | 0.005% |
| Water | 89.995% |
| Ethanol | 10.000% |

The compound of formula (I) is dissolved in ethanol and blended with water. The formulation is then packaged in a nebulizer equipped with a dosing pump.

Example 59

This example illustrates the preparation of a representative pharmaceutical formulation in aerosol form.

| Ingredients | % wt./wt. |
| --- | --- |
| Compound of formula (I) | 0.10% |
| Propellant 11/12 | 98.9% |
| Oleic acid | 1.00% |

The compound of formula (I) is dispersed in oleic acid and the propellants. The resulting mixture is then poured into an aerosol container fitted with a metering valve.

Example 60

In Vitro Matrilysin Assay

Matrilysin was purified from cloned mammalian cell culture by Blue-Sepharose and zinc-chelating sepharose column followed by fast protein liquid chromatography over a MONO S column. The enzyme was activated by incubation with 1 mmol APMA for 1 hr at 35–37° C.

Compounds of formula (I) were dissolved in DMSO and added to a cuvette containing 0.4 $\mu$g matrilysin in 1 ml TC buffer (20 mM Tris, 5 mM $CaCl_2$, pH 7.5) (2% DMSO final concentration). The concentrations of the compounds of formula (I) were chosen such that there was at least one data point for every 20% change in activity. Enzyme and compounds were permitted to preincubate 3 min at 37° C. To initiate the reaction, N-(7-dimethylamino-4-methyl-3-coumarinyl)maleimide ("DACM") (Sigma) and thiopeptide (AC-Pro-Leu-Gly-S-"Leu"-Leu-Gly-OEt, Bachem Bioscience Inc.) were added to 20 $\mu$M each. The fluorescence increase was recorded with excitation and emission wavelengths of 395 and 485 nm, respectively. Each data point is the average of duplicate experiments. At least six data points, expressed as change in fluorescence per minute versus compound concentration were analyzed using the $IC_{50}$ fit in the program, Enzfitter.

Compounds of formula (I) exhibited the ability to inhibit matrilysin when tested in this assay.

Example 61

In Vitro Assay

This assay determines if the compounds of formula (I) inhibit the release of $^{35}$S-labelled glycosaminoglycans (GAG's) from cartilage explants.

Small cartilage explants (3 mm diameter) were prepared from freshly sacrificed bovine knee joints and labeled with $^{35}SO_4$. $^{35}$S-labelled glycosaminoglycans (GAG's) are released into the culture medium in response to the addition of rhIL-1-alpha, which induces the expression of chondrocyte matrix metalloproteases (MMP's), including stromelysin and collagenase. The percent inhibition of labeled GAG's was corrected for spontaneous release in the absence of rhIL-1-alpha. Results for each group represent the mean±the S.E.M. for five explants.

Compounds of formula (I), when tested in this assay, displayed the ability to inhibit the release of $^{35}$S-labelled GAG's from cartilage explants.

Example 62

In Vitro Assay

An in vitro fetal rat long bone model was used to study the anti-bone resorptive effect of the compounds of formula (I). Bovine PTH was used to induce bone resorption in vitro. The bone resorptive effects were expressed by the amounts of $^{45}$Ca released from the $^{45}$Ca pre-labelled fetal rat long bones into the culture medium. The inhibitory effect of the compounds of formula (I) against bovine PTH induced bone resorption was expressed as mean percent inhibition±sem.

$^{45}$Ca-prelabelled fetal rat long bones (from forearms) were dissected and cultured in Linbro dishes at 37° C. overnight BGJb medium, supplemented with 1 mg/ml BSA. There were five pairs of bones in each group. The compounds of formula (I) were dissolved in ethanol first, then diluted to various concentrations and added simultaneously with Bovine PTH (1–34) at $1\times10^{-8}$M on Day 1. The ethanol concentrations in the compound solutions were less than 0.05% which did not interfere with the assay. The assay was terminated on Day 6 with one media change on Day 3.

At the end of each medium change, the $^{45}$Ca present in the culture medium was counted. The remaining bones were digested with 0.1N HCl and the $^{45}$Ca presented in the bone digest was also counted. The results are expressed as e of the total $^{45}$Ca released from each pair of bones. Bovine PTH at $\times10^{-8}$M induces bone resorption to the maximum level which is set as 100% and this concentration was used as standard. The level of base line bone resorption in the presence of medium only was set as 0%. All compound-treated groups were compared with bovine PTH (1–34) at $1\times10^{-8}$M. The concentration at which a compound inhibited bone resorption by 50% was defined as $IC_{50}$.

Compounds of formula (I) exhibited the ability to inhibit bovine PTH-induced bone resorption in this assay.

Example 63

In Vitro Stromelysin Assay

63A. Stromelysin enzymatic activity was measured by a resonance energy transfer fluorogenic assay using the MCA peptide substrate: 7-methoxycoumarin-4-yl-acetyl-pro-leu-gly-leu-3-(2,4-dinitrophenyl)-L-2,3-diaminoproprionyl-ala-arg-$NH_2$. Cleavage of the substrate at the gly-leu bond results in the loss of resonance energy transfer to the 2,4-dinitrophenyl group and an increase in fluorescence of the MCA (7-methoxycoumarin-4-yl-acetyl) group.

The assay was performed at 37° C. in buffer containing 50 mM Tricine, pH 7.5, 10 mM $CaCl_2$, 200 mM NaCl, 1% DMSO and 1.4 nM stromelysin. The concentration of MCA substrate was 10 or 20 $\mu$M in a final volume of 1.6 ml. In the absence of compounds to be tested for inhibitory activity, or in the presence of non-slowbinding inhibitors, fluorescence was measured with Perkin-Elmer LS-5B and LS-50B spectrofluorimeters with $\lambda_{excitation}$=328 nm and $\lambda_{emission}$=393 nm over a 3 to 5 minute time period and data were fitted to a straight line. For slow-binding inhibitors, inhibition data were collected for 45 minutes to 1 hour. Steady-state rates of fluorescence change were calculated by fitting the curve to an equation for a single exponential decay containing a linear phase, and taking the fitted value of the linear phase as the steady-state rate.

Compounds of formula (I) were tested and found to be active as inhibitors of MMP activity in this assay.

63B. The MCA assay can also be used with other matrix metalloproteinases, such as matrilysin or gelatinase A, by substituting 0.063 nM matrilysin or 0.030 nM gelatinase A for stromelysin.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

What is claimed is:

1. A compound of the formula:

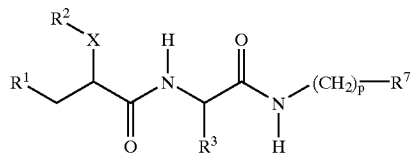

wherein:

$R^1$ is mercapto, carboxy, or a group of the formula:

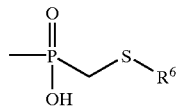

where $R^6$ is optionally substituted aryl or heteroaryl;

$R^2$ is alkyl, optionally substituted phenyl, or a group of the formula:

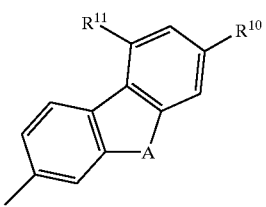

wherein:

A is $CH_2$, O, NH, S, $CH_2$—$CH_2$, or NH—$CH_2$;

$R^{10}$ is H, alkyl, alkoxy, alkylamino or acylamide; and $R^{11}$ is H or halo;

$R^7$ is 4-pyridyl and p is 0;

$R^3$ is alkyl, cycloalkyl, aralkyl, or heteroaralkyl, where the aralkyl and heteroaryl groups may be optionally substituted and where the alkyl is optionally substituted by cycloalkyl, hydroxy, mercapto, alkylthio, aralkoxy, amino, mono- and diallkylamino, guanidino, N,N-dialkylguanidino, carbamoyl, aryl or heteroaryl;

X is a group of the formula —$(CH_2)_m$—Y—$(CH_2)_n$—, where:

Y is O, S, or a single bond, m is an integer from 0 to 4, n is an integer from 0 to 4, and m+n is an integer from 0 to 4;

p is an integer from 0 to 4, provided that $R^2$—X is biphenylalkyl when p is not 0;

or a pharmaceutically acceptable salt thereof.

2. The compound or salt of claim 1, wherein: $R^3$ is t-butyl, 4-aminobutyl, dimethylaminobutyl, 4-(N,N'diethylguanido) butyl, propyl, 2-methylpropyl, 1-hydroxyisopropyl, 1-hydroxyethyl, or cyclohexyl; and X is a single bond, —$CH_2CH_2$— or —$CH_2CH_2CH_2$—.

3. The compound or salt of claim 1 wherein $R^2$ is biphenyl.

4. The compound or salt of claim 3 wherein: $R^1$ is carboxy, or mercapto; $R^3$ is alkyl; and $R^7$ is 4-pyridyl.

5. The compound or salt of claim 4 wherein $R^3$ is t-butyl and X is —$CH_2CH_2CH_2$—.

6. The compound or salt of claim 5 wherein $R^1$ is carboxy.

7. A pharmaceutical composition comprising a compound or salt of claim 1 and a pharmaceutically acceptable excipient.

* * * * *